(12) United States Patent
Han et al.

(10) Patent No.: US 6,525,025 B2
(45) Date of Patent: Feb. 25, 2003

(54) GAMMA-KETOACID DIPEPTIDES AS INHIBITORS OF CASPASE-3

(75) Inventors: Yongxin Han, Kirkland (CA); Andre Giroux, Ste-Anne-de-Bellevue (CA); Erich L. Grimm, Baie d'Urfe (CA); Renee Aspiotis, Westmount (CA); Cameron Black, Baie d'Urfe (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/948,244

(22) Filed: Sep. 7, 2001

(65) Prior Publication Data

US 2002/0165230 A1 Nov. 7, 2002

Related U.S. Application Data

(60) Provisional application No. 60/230,019, filed on Sep. 8, 2000.

(51) Int. Cl.[7] .................. A61K 38/00; A61K 31/195; A01N 37/12; A01N 37/44; C07C 205/00
(52) U.S. Cl. .................. 514/19; 514/564; 544/315; 546/152; 546/168; 548/131; 562/437
(58) Field of Search .................. 562/426, 427, 562/437, 438, 442, 444, 448, 455, 456, 457; 514/564, 19; 544/315; 546/152, 168; 548/131

(56) References Cited

U.S. PATENT DOCUMENTS

| | | |
|---|---|---|
| 5,585,357 A | 12/1996 | Dolle e tal. |
| 5,639,783 A | 6/1997 | Ando et al. |
| 5,656,627 A | 8/1997 | Bemis et al. |
| 5,677,283 A | 10/1997 | Dolle et al. |
| 5,834,508 A | 11/1998 | Ando et al. |
| 5,843,904 A | 12/1998 | Bemis et al. |
| 5,866,545 A | 2/1999 | Hagmann et al. |

FOREIGN PATENT DOCUMENTS

| | | |
|---|---|---|
| EP | 0 525 420 | 7/1992 |
| EP | 0 623 592 | 4/1994 |
| EP | 0 623 606 A2 | 4/1994 |
| GB | 2 292 149 A | 2/1996 |
| WO | WO 93/16710 | 9/1993 |
| WO | WO 95/05192 | 2/1995 |
| WO | WO 97/22618 | 6/1997 |
| WO | WO 98/10778 | 3/1998 |
| WO | WO98/16502 | 4/1998 |
| WO | WO 98/22098 | 5/1998 |
| WO | WO 00/23421 | 4/2000 |

OTHER PUBLICATIONS

"Caspases: Killer Proteaes" Nicholson and Thornberry. Trends in Biochemical Science vol. 22, pp. 299–306 (1997).*

Nicholson, D. W., et al.; Nature, vol. 376, No. 6535, pp. 37–43, 1995.

* cited by examiner

*Primary Examiner*—Richard L. Raymond
*Assistant Examiner*—Zachary C. Tucker
(74) *Attorney, Agent, or Firm*—Raymond Yuro; David L. Rose

(57) ABSTRACT

This invention encompasses the novel compounds of Formula I, which are useful in the treatment of caspase-3 mediated diseases.

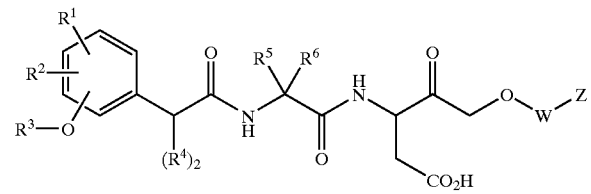

The invention also encompasses certain pharmaceutical compositions comprising compounds of Formula I as well as methods for treatment of caspase-3 mediated diseases.

22 Claims, No Drawings

GAMMA-KETOACID DIPEPTIDES AS INHIBITORS OF CASPASE-3

CROSS-REFERENCE TO RELATED APPLICATIONS

This application claims the benefit of U.S. Provisional Application No. 60/231,019, filed on Sep. 8, 2000.

BACKGROUND OF THE INVENTION

Apoptotic cell suicide is a fundamentally important biological process that is required to maintain the integrity and homeostasis of multicellular organisms. Inappropriate apoptosis, however, underlies the etiology of many of the most intractable of human diseases. In only the last few years, many of the molecules that participate in a conserved biochemical pathway that mediates the highly ordered process of apoptotic cell suicide have been identified. At the heart of this pathway are a family of cysteine proteases, the 'caspases', that are related to mammalian interleukin-1β converting enzyme (ICE/caspase-1) and to CED-3, the product of a gene that is necessary for apoptotic suicide in the nematode *C. elegans* (Nicholson et al., 1997, Trends Biochem Sci 22:299–306). The role of these proteases in cell suicide is to disable critical homeostatic and repair processes as well as to cleave key structural components, resulting in the systematic and orderly disassembly of the dying cell.

The central importance of caspases in these processes has been demonstrated with both macromolecular and peptide-based inhibitors (which prevent apoptosis from occurring in vitro and in vivo) as well as by genetic approaches. Inhibition of apoptosis via attenuation of caspase activity should therefore be useful in the treatment of human diseases where inappropriate apoptosis is prominent or contributes to disease pathogenesis. Caspase inhibitors would thus be useful for the treatment of human diseases including, but not limited to, acute disorders such as cardiac and cerebral ischemia/reperfusion injury (e.g. stroke), spinal cord injury and organ damage during transplantation, as well as chronic disorders such as neurodegenerative diseases (e.g. Alzheimer's, polyglutamine-repeat disorders, Down's, spinal muscular atrophy, multiple sclerosis), immunodeficiency (e.g. HIV), diabetes, alopecia and aging.

Ten caspases have so far been identified in human cells. Each is synthesized as a catalytically dormant proenzyme containing an amino-terminal rodomain followed by the large and small subunits of the heterodimeric active enzyme. The subunits are excised from the proenzyme by cleavage at Asp-X unctions (Nicholson et al., 1997, Trends Biochem Sci 22:299–306). The strict requirement by caspases for Asp in the P1 position of substrates is consistent with a mechanism whereby proenzyme maturation can be either autocatalytic or performed by other caspases. The three dimensional crystal structures of mature caspase-1 and -3 show that the large subunit contains the principle components of the catalytic machinery, including the active site Cys residue which is harbored within the conserved pentapeptide motif, QACxG,1 and residues that stabilize the oxyanion of the tetrahedral transition state (Wilson et al., 1994, Nature 370:270–75; Walker et al., 1994, Cell 78:342–52; Rotonda et al., 1996, Nat Struct Biol 3:619–25). Both subunits contribute residues which stabilize the P1 Asp of substrates while the small subunit appears to contain most of the determinants that dictate substrate specificity and, in particular, those which form the specificity-determining S4 subsite. One distinctive feature of these proteases is the absolute requirement for an aspartic acid residue in the substrate P1 position. The carboxylate side chain of the substrate P1 Asp is tethered by four residues in caspase-1 (Arg179, Gln238 from p20 and Arg341, Ser347 from p10) that are absolutely conserved in all caspase family members. Catalysis involves a typical cysteine protease mechanism involving a catalytic dyad, composed of His237 and Cys285 (contained within an absolutely conserved QACxG pentapeptide) and an 'oxyanion hole' involving Gly238 and Cys285. Inhibitors bind, however, in an unexpected non-transition state configuration (which raises important considerations for inhibitor design) with the oxyanion of the thiohemiacetal being stabilized by the active site His237.

Members of the caspase family can be divided into three functional subgroups based on their substrate specificities which have been defined by a positional-scanning combinatorial substrate approach. The principle effectors of apoptosis (group II caspases, which include caspases-2, -3 and -7 as well as *C. elegans* CED-3) have specificity for [P4]DExD[P1], a motif found at the cleavage site of most proteins known to be cleaved during apoptosis. On the other hand, the specificity of group mH caspases (caspases-6, -8, -9 and -10, as well as CTL-derived granzyme B) is [P4](I,V,L)ExD[P1] which corresponds to the activation site at the junction between the large and small subunits of other caspase proenzymes including group II (effector) family members. This and other evidence indicates that group III caspases function as upstream activators of group II caspases in a proteolytic cascade that amplifies the death signal. The role of group I caspases (caspases-1, -4 and -5) appears to be to mediate cytokine maturation and their role in apoptosis, if any, has not been substantiated.

A tetrapeptide corresponding to the substrate P4–P1 residues is sufficient for specific recognition by caspases and as a consequence has formed the basis for inhibitor design. In addition to the requirement for a P1 Asp, the P4 residue in particular appears to be most important for substrate recognition and specificity. Caspase-1, for example, prefers a hydrophobic residue such as Tyr in P4 (which corresponds to its YVHD cleavage site within proIL-1β) whereas caspase-3 (and other group II enzymes) has a preference for an anionic Asp residue (which corresponds to the DXXD cleavage sites within most polypeptides that are cleaved by these enzymes during apoptosis). Peptide aldehydes, nitriles and ketones are potent reversible inhibitors of these proteases while compounds that form thiomethylketone adducts with the active site cysteine (e.g. peptide (acyloxy)methylketones) are potent irreversible inhibitors. For example, the tetrapeptide aldehyde Ac-YVAD-CHO (which was designed to mimic the YVHD caspase-1 recognition sequence within proIL-1) is a potent inhibitor of caspase-1 ($K_i<1$ nM) but a poor inhibitor of caspase-3 ($K_i=12$ μM) (Thornberry et al., 1992, Nature 356:768–74). In contrast, the Ac-DEVD-CHO tetrapeptide aldehyde (which was designed to mimic the caspase-3 recognition site) is a very potent inhibitor of caspase-3 ($K_i<1$ nM) although it is also a weaker but reasonable inhibitor of caspase-1, presumably owing to promiscuity in the S4 subsite of this enzyme (Nicholson et al., 1995, Nature 376:37–43).

Several features plague these peptide-derived inhibitors as a platform for drug design. In addition to their metabolic instability and membrane impermeability, the slow-binding time-dependent inhibition of activity (e.g. kon caspase-1:Ac-YVAD-CHO=$3.8 \times 10^5$ $M^{-1}s^{-1}$; kon caspase-3:Ac-DEVD-CHO=$1.3 \times 10^5$ $M^{-1}s^{-1}$) precludes them from the rapid inhibition characteristics that may be necessary to abolish enzymatic activity in vivo. The present patent application describes the resolution of this issue with the discovery of several novel gamma-ketoacids that make highly suitable caspase inhibitors.

SUMMARY OF THE INVENTION

This invention encompasses the novel compounds of Formula I:

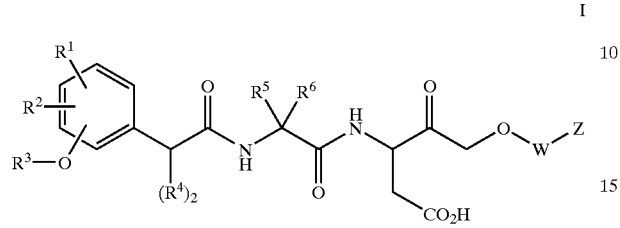

or a pharmaceutically acceptable salt, ester or hydrate thereof, wherein:

W is a bond, —$CH_2$—, —C(O)— or —C(O)$CH_2$—;

Z is selected from the group consisting of:
(1) H,
(2) $C_{1-11}$alkyl,
(3) $C_{3-11}$cycloalkyl or a benzofused analog thereof,
(4) phenyl or naphthyl, and
(5) $HET^1$, wherein $HET^1$ represents a 5- to 10-membered mono- or bicyclic, aromatic or non-aromatic ring, or a benzofused analog thereof, containing 1–3 heteroatoms selected from O, S and N, groups (2), (3) and (5) above are optionally substituted with 1–2 oxo groups, groups (2)–(5) above are further optionally substituted with 1–3 substituents independently selected from the group consisting of:
(a) halo
(b) nitro,
(c) hydroxy,
(d) $C_{1-4}$alkyl,
(e) $C_{1-4}$alkoxy,
(f) $C_{1-4}$alkylthio,
(g) $C_{3-6}$cycloalkyl,
(h) phenyl or naphthyl,
(i) phenoxy,
(j) benzyl,
(k) benzyloxy, and
(l) a 5 or 6-membered aromatic or non-aromatic ring containing from 1–3 heteroatoms selected from O, S and N, groups (d)–(g) above are optionally substituted with oxo and 1–3 substituents independently selected from halo and $C_{1-4}$alkoxy, groups (h)–(l) above are optionally substituted with 1–3 substituents independently selected from halo and $C_{1-4}$alkyl, and group (4) is further optionally substituted up to its maximum with halo groups;

$R^1$ and $R^2$ are independently selected from the group consisting of:
(1) H,
(2) halo,
(3) hydroxy,
(4) nitro,
(5) cyano,
(6) $C_{1-10}$alkyl, $C_{3-10}$cycloalkyl, $C_{1-10}$alkoxy, —S(O)$_{0-2}$$C_{1-10}$alkyl or —NH$C_{1-10}$alkyl, each optionally substituted with 1–2 oxo or carboxy groups and further optionally substituted with 1–3 substituents independently selected from the group consisting of:
(a) halo,
(b) hydroxy
(c) cyano,
(d) $C_{1-4}$alkoxy,
(e) —$NHR^7$, wherein $R^7$ is H or $C_{1-5}$alkyl, said $C_{1-5}$alkyl optionally substituted with —$NHR^8$, wherein $R^8$ is $C_{1-5}$alkyl optionally substituted with oxo and further optionally substituted with a 5- to 10-membered mono- or bicyclic, aromatic or non-aromatic ring, or a benzofused analog thereof, containing 1–3 heteroatoms selected from O, S and N, and optionally substituted with oxo,
(f) —S(O)$_{0-2}$$C_{1-4}$alkyl, and
(g) $HET^2$, wherein $HET^2$ represents a 5- to 7-membered aromatic or non-aromatic ring containing 1–4 heteroatoms selected from O, S and $NR^7$, wherein $R^7$ is H or $C_{1-5}$alkyl, said $HET^2$ being optionally substituted with oxo and further optionally substituted with 1–2 substituents independently selected from halo and $C_{1-4}$alkyl, said $C_{1-4}$alkyl being optionally substituted with 1–3 halo groups,
(7) phenoxy or —S(O)$_{0-2}$phenyl,
(8) benzyloxy or —S(O)$_{0-2}$benzyl,
(9) benzoyl,
(10) phenyl or naphthyl,
(11) —O-$HET^2$ or —S-$HET^2$, said $HET^2$ being optionally substituted with oxo and further optionally substituted as defined below, and
(12) $HET^3$, wherein $HET^3$ is a 5- or 6-membered aromatic or non-aromatic ring, or a benzofused analog thereof, containing from 1 to 4 heteroatoms selected from O, S and N, said $HET^3$ being optionally substituted with oxo and further optionally substituted as defined below, groups (7)–(12) above are each optionally substituted with 1–2 substituents independently selected from the group consisting of: halo, cyano, $C_{1-4}$alkyl and $C_{1-4}$alkoxy, said $C_{1-4}$alkyl and $C_{1-4}$alkoxy being optionally substituted with 1–3 halo groups;

or $R^1$ and $R^2$ may be taken in combination and represent a fused ring as shown below:

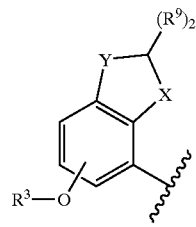

wherein Y and X are independently selected from the group consisting of —$C(R^{10})_2$—, —$C(R^{10})_2C(R^{10})_2$—, $NR^{11}$—, —O— and —S—, $R^3$ is as defined below, each $R^9$ is independently selected from H and $C_{1-4}$alkyl, each $R^{10}$ is independently selected from H and $C_{1-4}$alkyl, and $R^{11}$ is H or $C_{1-4}$alkyl, or one $R^9$ may be joined with either one $R^{10}$ or $R^{11}$ on an adjacent atom to form a double bond;

$R^3$ is $C_{1-10}$alkyl, optionally substituted with 1–2 oxo or carboxy groups and further optionally substituted with 1–3 substituents independently selected from the group consisting of:

(a) halo,
(b) hydroxy
(c) cyano,
(d) $C_{1-4}$alkoxy,
(e) —NHR$^7$, wherein R$^7$ is H or $C_{1-5}$alkyl, said $C_{1-5}$alkyl optionally substituted with —NHR$^8$, wherein R$^8$ is $C_{1-5}$alkyl optionally substituted with oxo and further optionally substituted with a 5- to 10-membered mono- or bicyclic, aromatic or non-aromatic ring, or a benzofused analog thereof, containing 1–3 heteroatoms selected from O, S and N, and optionally substituted with oxo,
(f) —S(O)$_{0-2}$C$_{1-4}$alkyl, and
(g) HET$^2$, wherein HET$^2$ represents a 5- to 7-membered aromatic or non-aromatic ring containing 1–4 heteroatoms selected from O, S and NR$^7$, wherein R$^7$ is H or $C_{1-5}$alkyl, said HET$^2$ being optionally substituted with oxo and further optionally substituted with 1–2 substituents independently selected from halo or $C_{1-4}$alkyl, said $C_{1-4}$alkyl being optionally substituted with 1–3 halo groups, each R$^4$ is independently selected from the group consisting of: H, halo, hydroxy, $C_{1-6}$alkyl and $C_{1-4}$alkoxy, said $C_{1-6}$alkyl and $C_{1-4}$alkoxy being optionally substituted with oxo and further optionally substituted with 1–3 halo groups; and R$^5$ is selected from the group consisting of: H, phenyl, naphthyl, $C_{1-6}$alkyl optionally substituted with OR$^{12}$ and 1–3 halo groups, and $C_{5-7}$cycloalkyl optionally containing one heteroatom selected from O, S and NR$^{13}$, wherein R$^{12}$ is selected from the group consisting of: H, $C_{1-5}$alkyl optionally substituted with 1–3 halo groups, and benzyl optionally substituted with 1–3 substituents independently selected from halo, $C_{1-4}$alkyl and $C_{1-4}$alkoxy, and R$^{13}$ is H or $C_{1-4}$alkyl optionally substituted with 1–3 halo groups; and R$^6$ represents H;

or in the alternative, R$^5$ and R$^6$ are taken in combination and represent a ring of 4–7 members, said ring optionally containing one heteroatom selected from O, S and NR$^{13}$.

The invention also encompasses pharmaceutical compositions containing a compound of Formula I as well as methods for treating caspase-3 mediated diseases.

DETAILED DESCRIPTION OF THE INVENTION

The present invention encompasses compounds of Formula I:

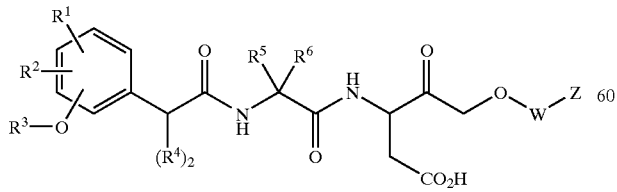

I or a pharmaceutically acceptable salt, ester or hydrate thereof, wherein:

W is a bond, —CH$_2$—, —C(O)— or C(O)CH$_2$—;
Z is selected from the group consisting of:
(1) H,
(2) $C_{1-11}$alkyl,
(3) $C_{3-11}$cycloalkyl or a benzofused analog thereof,
(4) phenyl or naphthyl, and
(5) HET$^1$, wherein HET$^1$ represents a 5- to 10-membered mono- or bicyclic, aromatic or non-aromatic ring, or a benzofused analog thereof, containing 1–3 heteroatoms selected from O, S and N, groups (2), (3) and (5) above are optionally substituted with 1–2 oxo groups, groups (2)–(5) above are further optionally substituted with 1–3 substituents independently selected from the group consisting of:
(a) halo
(b) nitro,
(c) hydroxy,
(d) $C_{1-4}$alkyl,
(e) $C_{1-4}$alkoxy,
(f) $C_{1-4}$alkylthio,
(g) $C_{3-6}$cycloalkyl,
(h) phenyl or naphthyl,
(i) phenoxy,
(j) benzyl,
(k) benzyloxy, and
(l) a 5 or 6-membered aromatic or non-aromatic ring containing from 1–3 heteroatoms selected from O, S and N, groups (d)–(g) above are optionally substituted with oxo and 1–3 substituents independently selected from halo and $C_{1-4}$alkoxy, groups (h)–(l) above are optionally substituted with 1–3 substituents independently selected from halo and $C_{1-4}$alkyl, and group (4) is further optionally substituted up to its maximum with halo groups; R$^1$ and R$^2$ are independently selected from the group consisting of:
(1) H,
(2) halo,
(3) hydroxy,
(4) nitro,
(5) cyano,
(6) $C_{1-10}$alkyl, $C_{3-10}$cycloalkyl, $C_{1-10}$alkoxy, —S(O)$_{0-2}$C$_{1-10}$alkyl or —NHC$_{1-10}$alkyl, each optionally substituted with 1–2 oxo or carboxy groups and further optionally substituted with 1–3 substituents independently selected from the group consisting of:
(a) halo,
(b) hydroxy
(c) cyano,
(d) $C_{1-4}$alkoxy,
(e) —NHR$^7$, wherein R$^7$ is H or $C_{1-5}$alkyl, said $C_{1-5}$alkyl optionally substituted with —NHR$^8$, wherein R$^8$ is $C_{1-5}$alkyl optionally substituted with oxo and further optionally substituted with a 5- to 10-membered mono- or bicyclic, aromatic or non-aromatic ring, or a benzofused analog thereof, containing 1–3 heteroatoms selected from O, S and N, and optionally substituted with oxo,
(f) —S(O)$_{0-2}$C$_{1-4}$alkyl, and
(g) HET$^2$, wherein HET$^2$ represents a 5- to 7-membered aromatic or non-aromatic ring containing 1–4 heteroatoms selected from O, S and NR$^7$, wherein R$^7$ is H or C s5alkyl, said HET$^2$ being optionally substituted with oxo and further optionally substituted with 1–2 substituents independently selected from halo and $C_{1-4}$alkyl, said $C_{1-4}$alkyl being optionally substituted with 1–3 halo groups, (7) phenoxy or —S(O)$_{0-2}$phenyl, (8) benzyloxy or —S(O)$_{0-2}$benzyl, (9) benzoyl,

(10) phenyl or naphthyl,

(11) —O-HET$^2$ or —S-HET$^2$, said HET$^2$ being optionally substituted with oxo and further optionally substituted as defined below, and

(12) HET$^3$, wherein HET$^3$ is a 5- or 6-membered aromatic or non-aromatic ring, or a benzofused analog thereof, containing from 1 to 4 heteroatoms selected from O, S and N, said HET$^3$ being optionally substituted with oxo and further optionally substituted as defined below, groups (7)–(12) above are each optionally substituted with 1–2 substituents independently selected from the group consisting of: halo, cyano, $C_{1-4}$alkyl and $C_{1-4}$alkoxy, said $C_{1-4}$alkyl and $C_{1-4}$alkoxy being optionally substituted with 1–3 halo groups;

or R$^1$ and R$^2$ may be taken in combination and represent a fused ring as shown below:

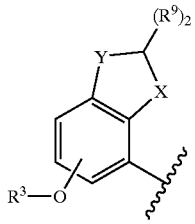

wherein Y and X are independently selected from the group consisting of —C(R$^{10}$)$_2$, —C(R$^{10}$)$_2$C(R$^{10}$)$_2$—, —NR$^{11}$—, —O— and —S—, R$^3$ is as defined below, each R$^9$ is independently selected from H and $C_{1-4}$alkyl, each R$^{10}$ is independently selected from H and $C_{1-4}$alkyl, and R$^{11}$ is H or $C_{1-4}$alkyl, or one R$^9$ may be joined with either one R$^{10}$ or R$^{11}$ on an adjacent atom to form a double bond;

R$^3$ is $C_{1-10}$alkyl, optionally substituted with 1–2 oxo or carboxy groups and further optionally substituted with 1–3 substituents independently selected from the group consisting of:

(a) halo, (b) hydroxy (c) cyano, (d) $C_{1-4}$alkoxy, (e) —NHR$^7$, wherein R$^7$ is H or $C_{1-5}$alkyl, said $C_{1-5}$alkyl optionally substituted with —NHR$^8$, wherein R$^8$ is $C_{1-5}$alkyl optionally substituted with oxo and further optionally substituted with a 5- to 10-membered mono- or bicyclic, aromatic or non-aromatic ring, or a benzofused analog thereof, containing 1–3 heteroatoms selected from O, S and N, and optionally substituted with oxo, (f) —S(O)$_{0-2}$C$_{1-4}$alkyl, and (g) HET$^2$, wherein HET$^2$ represents a 5- to 7-membered aromatic or non-aromatic ring containing 1–4 heteroatoms selected from O, S and NR$^7$, wherein R$^7$ is H or $C_{1-5}$alkyl, said HET$^2$ being optionally substituted with oxo and further optionally substituted with 1–2 substituents independently selected from halo or $C_{1-4}$alkyl, said $C_{1-4}$alkyl being optionally substituted with 1–3 halo groups, each R$^4$ is independently selected from the group consisting of: H, halo, hydroxy, $C_{1-6}$alkyl and $C_{1-4}$alkoxy, said $C_{1-6}$alkyl and $C_{1-4}$alkoxy being optionally substituted with oxo and further optionally substituted with 1–3 halo groups; and R$^5$ is selected from the group consisting of: H, phenyl, naphthyl, $C_{1-6}$alkyl optionally substituted with OR$^{12}$ and 1–3 halo groups, and $C_{5-7}$cycloalkyl optionally containing one heteroatom selected from O, S and NR$^{13}$, wherein R$^{12}$ is selected from the group consisting of: H, $C_{1-5}$alkyl optionally substituted with 1–3 halo groups, and benzyl optionally substituted with 1–3 substituents independently selected from halo, $C_{1-4}$alkyl and $C_{1-4}$alkoxy, and R$^{13}$ is H or $C_{1-4}$alkyl optionally substituted with 1–3 halo groups; and R$^6$ represents H;

or in the alternative, R$^5$ and R$^6$ are taken in combination and represent a ring of 4–7 members, said ring optionally containing one heteroatom selected from O, S and NR$^{13}$.

An embodiment of the invention encompasses compounds of Formula I wherein R$^1$ is selected from the group consisting of:

(1) halo, (2) hydroxy, (3) nitro, (4) cyano, (5) $C_{1-10}$alkyl, $C_{3-10}$cycloalkyl, $C_{1-10}$alkoxy, —S(O)$_{0-2}$ $C_{1-10}$alkyl or —NHC$_{1-10}$alkyl, each optionally substituted with 1–2 oxo or carboxy groups and further optionally substituted with 1–3 substituents independently selected from the group consisting of:

(a) halo, (b) hydroxy (c) cyano, (d) $C_{1-4}$alkoxy, (e) —NHR$^7$, wherein R$^7$ is H or $C_{1-5}$alkyl, said $C_{1-5}$alkyl optionally substituted with —NHR$^8$, wherein R$^8$ is $C_{1-5}$alkyl optionally substituted with oxo and further optionally substituted with a 5- to 10-membered mono- or bicyclic, aromatic or non-aromatic ring, or a benzofused analog thereof, containing 1–3 heteroatoms selected from O, S and N, and optionally substituted with oxo, (f) —S(O)$_{0-2}$C$_{1-4}$alkyl, and (g) HET$^2$, wherein HET$^2$ represents a 5- to 7-membered aromatic or non-aromatic ring containing 1–4 heteroatoms selected from O, S and NR$^7$, wherein R$^7$ is H or $C_{1-5}$alkyl, said HET$^2$ being optionally substituted with oxo and further optionally substituted with 1–2 substituents independently selected from halo and $C_{1-4}$alkyl, said $C_{1-4}$alkyl being optionally substituted with 1–3 halo groups, (6) phenoxy or —S(O)$_{0-2}$phenyl, (7) benzyloxy or —S(O)$_{0-2}$benzyl, (8) benzoyl, (9) phenyl or naphthyl,

(10) —O-HET$^2$ or —S-HET$^2$, said HET$^2$ being optionally substituted with oxo and further optionally substituted as defined below, and

(11) HET$^3$, wherein HET$^3$ is a 5- or 6-membered aromatic or non-aromatic ring, or a benzofused analog thereof, containing from 1 to 4 heteroatoms selected from O, S and N, said $HET^3$ being optionally substituted with oxo and further optionally substituted as defined below, and groups (6)–(11) above are each optionally substituted with 1–2 substituents independently selected from the group consisting of: halo, cyano, $C_{1-4}$alkyl and $C_{1-4}$alkoxy, said $C_{1-4}$alkyl and $C_{1-4}$alkoxy being optionally substituted with 1–3 halo groups.

An embodiment of the invention encompasses compounds of Formula I wherein $R^3$ is methyl, optionally substituted with 1–3 halo groups.

Another embodiment of the invention encompasses compounds of Formula I wherein one $R^4$ is hydroxy and the other $R^4$ is H.

Another embodiment of the invention encompasses compounds of Formula I wherein $R^5$ is isopropyl and $R^6$ is H.

Another embodiment of the invention encompasses compounds of Formula I wherein W is a bond. Another embodiment of the invention encompasses compounds of Formula I wherein W is —$CH_2$—. Another embodiment of the invention encompasses compounds of Formula I wherein W is —C(O)—. Another embodiment of the invention encompasses compounds of Formula I wherein W is $C(O)CH_2$—.

Another embodiment of the invention encompasses compounds of Formula I wherein Z is phenyl or naphthyl, wherein: said phenyl or naphthyl is optionally substituted with 1–3 substituents independently selected from the group consisting of:

(a) nitro,
(b) hydroxy,
(c) $C_{1-4}$alkyl,
(d) $C_{1-4}$alkoxy,
(e) $C_{1-4}$alkylthio,
(f) $C_{3-6}$cycloalkyl,
(g) phenyl or naphthyl,
(h) phenoxy,
(i) benzyl,
(l) benzyloxy, and
(k) a 5 or 6-membered aromatic or non-aromatic ring containing from 1–3 heteroatoms selected from O, S and N, groups (c)–(f) above are optionally substituted with oxo and 1–3 substituents independently selected from halo and $C_{1-4}$alkoxy, groups (g)–(k) above are optionally substituted with 1–3 substituents independently selected from halo and $C_{1-4}$alkyl, and said phenyl or naphthyl is further optionally substituted up to its maximum with halo groups.

Another embodiment of the invention encompasses compounds of Formula I wherein Z is $C_{1-11}$alkyl, optionally substituted with 1–2 oxo groups and further optionally substituted with 1–3 substituents independently selected from the group consisting of:

(a) halo
(b) nitro,
(c) hydroxy,
(d) $C_{1-4}$alkyl,
(e) $C_{1-4}$alkoxy,
(f) $C_{1-4}$alkylthio,
(g) $C_{3-6}$cycloalkyl,
(h) phenyl or naphthyl,
(i) phenoxy,
(j) benzyl,
(k) benzyloxy, and
(l) a 5 or 6-membered aromatic or non-aromatic ring containing from 1–3 heteroatoms selected from O, S and N, groups (d)–(g) above are optionally substituted with oxo and 1–3 substituents independently selected from halo and $C_{1-4}$alkoxy and groups (h)–(l) above are optionally substituted with 1–3 substituents independently selected from halo and $C_{1-4}$alkyl.

Another embodiment of the invention encompasses compounds of Formula I wherein Z is $C_{3-11}$cycloalkyl or a benzofused analog thereof, optionally substituted with 1–2 oxo groups and further optionally substituted with 1–3 substituents independently selected from the group consisting of:

(a) halo
(b) nitro,
(c) hydroxy,
(d) $C_{1-4}$alkyl,
(e) $C_{1-4}$alkoxy,
(f) $C_{1-4}$alkylthio,
(g) $C_{3-6}$cycloalkyl,
(h) phenyl or naphthyl,
(i) phenoxy,
(j) benzyl,
(k) benzyloxy, and
(l) a 5 or 6-membered aromatic or non-aromatic ring containing from 1–3 heteroatoms selected from O, S and N, groups (d)–(g) above are optionally substituted with oxo and 1–3 substituents independently selected from halo and $C_{1-4}$alkoxy, and groups (h)–(l) above are optionally substituted with 1–3 substituents independently selected from halo and $C_{1-4}$alkyl.

Another embodiment of the invention encompasses compounds of Formula I wherein Z is $HET^1$, optionally substituted with 1–2 oxo groups and further optionally substituted with 1–3 substituents independently selected from the group consisting of:

(a) halo
(b) nitro,
(c) hydroxy,
(d) $C_{1-4}$alkyl,
(e) $C_{1-4}$alkoxy,
(f) $C_{1-4}$alkylthio,
(g) $C_{3-6}$cycloalkyl,
(h) phenyl or naphthyl,
(i) phenoxy,
(j) benzyl,
(k) benzyloxy, and
(l) a 5 or 6-membered aromatic or non-aromatic ring containing from 1–3 heteroatoms selected from O, S and N, groups (d)–(g) above are optionally substituted with oxo and 1–3 substituents independently selected from halo and $C_{1-4}$alkoxy, and groups (h)–(k) above are optionally substituted with 1–3 substituents independently selected from halo and $C_{1-4}$alkyl.

Another embodiment of the invention encompasses compounds of Formula I wherein $HET^1$ represents a member selected from the group consisting of: pyridine, pyrimidine, pyridazine, pyrazine, furan, thiophene, thiazole and oxazole, or a benzofused analog thereof, each optionally substituted with 1–3 substituents independently selected from the group consisting of:
  (a) halo,
  (b) nitro,
  (c) $C_{1-4}$alkyl,
  (d) $C_{1-4}$alkoxy,
  (e) $C_{1-4}$alkylthio,
  (f) $C_{3-6}$cycloalkyl,
  (g) phenoxy,
  (h) benzyl,
  (i) benzyloxy, and
  (j) a 5 or 6-membered aromatic or non-aromatic ring containing from 1–3 heteroatoms selected from O, S and N,
  groups (c)–(f) above are optionally substituted with oxo and 1–3 substituents independently selected from halo and $C_{1-4}$alkoxy, and groups (g)–(j) above are optionally substituted with 1–3 substituents independently selected from halo and $C_{1-4}$alkyl.

Another embodiment of the invention encompasses compounds of Formula I wherein $HET^2$ is selected from the group consisting of: butyrolactone, tetrahydrofuran, tetrahydropyran, 2-pyrrolidinone, pyridine and pyrimidine, each optionally substituted with 1–2 substituents independently selected from halo or $C_{1-4}$alkyl, said $C_{1-4}$alkyl being optionally substituted with 1–3 halo groups.

Another embodiment of the invention encompasses compounds of Formula I wherein $HET^3$ is selected from the group consisting of: 1,2,3-oxadiazole, 1,2,4-oxadiazole, 1,3,4-oxadiazole, 1,2,3-thiadiazole, 1,2,4-thiadiazole, 1,3,4-thiadiazole, thiophene, pyrrole, pyridine, tetrazole, oxazole, thiazole, 1,2,3-triazole, 1,2,4-triazole and 1,3,4-triazole, each optionally substituted with 1–2 substituents independently selected from halo or $C_{1-4}$alkyl, said $C_{1-4}$alkyl being optionally substituted with 1–3 halo groups.

Another embodiment of the invention encompasses compounds of formula I wherein:
  W is a bond, —$CH_2$—, (O)— or —$C(O)CH_2$—;
  Z is selected from the group consisting of:
    (1) $C_{5-6}$cycloalkyl or a benzofused analog thereof,
    (2) phenyl or naphthyl, and
    (3) $HET^1$, wherein $HET^1$ represents a 5- to 10-membered mono-bicyclic, aromatic or non-aromatic ring, or a benzofused analog thereof, containing 3 heteroatoms selected from O, S and N, wherein:
      groups (1) and (3) above are optionally substituted with 1–2 oxo groups;
      groups (1), (2) and (3) above are further optionally substituted with 1–3 substituents independently selected from the group consisting of:
        (a) halo,
        (b) nitro,
        (c) $C_{1-4}$alkyl,
        (d) $C_{1-4}$alkoxy,
        (e) $C_{1-4}$alkylthio,
        (f) $C_{3-6}$cycloalkyl,
        (g) phenoxy,
        (h) benzyl,
        (i) benzyloxy, and
        (j) a 5 or 6-membered aromatic or non-aromatic ring containing from 1–3 heteroatoms selected from O, S and N,
      groups (c)–(f) above are optionally substituted with oxo and 1–3 substituents independently selected from halo and $C_{1-4}$alkoxy,
      groups (g)–(j) above are optionally substituted with 1–3 substituents independently selected from halo and $C_{1-4}$alkyl, and
      group (2) is further optionally substituted up to its maximum with halo groups;

$R^1$ is selected from the group consisting of:
  (1) halo,
  (2) $C_{1-4}$alkyl or $C_{1-4}$alkoxy, each optionally substituted with oxo and 1–3 halo groups, and
  (3) $HET^3$, wherein $HET^3$ is a 5- or 6-membered aromatic or non-aromatic ring, or a benzofused analog thereof, containing from 1 to 4 heteroatoms selected from O, S and N, and optionally substituted with 1–2 substituents independently selected from halo and $C_{1-4}$alkyl, said $C_{1-4}$alkyl being optionally substituted with 1–3 halo groups, $R^2$ is H, $R^3$ is $C_{1-4}$alkyl, optionally substituted with 1–3 halo groups and further optionally substituted with oxo or —$NHR^7$ or both, wherein $R^7$ is H or $C_{1-5}$alkyl, said $C_{1-5}$alkyl optionally substituted with —$NHR^8$, wherein $R^8$ is $C_{1-5}$alkyl optionally substituted with oxo and further optionally substituted with

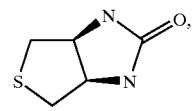

and each $R^4$ is independently selected from the group consisting of: H and hydroxy.

Within this embodiment there is a class of compounds of Formula I wherein $R^5$ is isopropyl and $R^6$ is H.

Within this class, there is a subclass of compounds of Formula I wherein: $HET^1$ is selected from the group consisting of:
  (1) pyridine, pyridazine, pyrimidine or pyrazine, or a benzofused analog thereof, each optionally substituted with 1–3 substituents independently selected from the group consisting of:
    (a) halo,
    (b) nitro,
    (c) $C_{1-4}$alkyl,
    (d) $C_{1-4}$alkoxy,
    (e) $C_{1-4}$alkylthio,
    (f) $C_{3-6}$cycloalkyl,
    (g) phenoxy,
    (h) benzyl,
    (i) benzyloxy, and
    (j) a 5 or 6-membered aromatic or non-aromatic ring containing from 1–3 heteroatoms selected from O, S and N,
  groups (c)–(f) above are optionally substituted with oxo and 1–3 substituents independently selected from halo and $C_{1-4}$alkoxy,
  groups (g)–(j) above are optionally substituted with 1–3 substituents independently selected from halo and $C_{1-4}$alkyl,

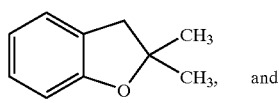
(2)

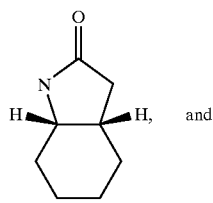
and
(3)

HET³ is 1,2,4-oxadiazole, optionally substituted with C₁₋₄alkyl.

For purposes of this specification alkyl means linear or branched structures and combinations thereof, containing one to twenty carbon atoms unless otherwise specified. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, and the like.

Cycloalkyl means cyclic structures, optionally combined with linear or branched structures, containing one to twenty carbon atoms unless otherwise specified. Examples of cycloalkyl groups include cyclopropyl, cyclopentyl, cycloheptyl, adamantyl, cyclododecylmethyl, 2-ethyl-1-bicyclo[4.4.0]decyl and the like.

Alkoxy means alkoxy groups of one to ten carbon atoms, unless otherwise specified, of a straight, branched or cyclic configuration. Examples of alkoxy groups include methoxy, ethoxy, propoxy, isopropoxy, and the like.

Alkylthio means alkylthio groups of one to ten carbon atoms, unless otherwise specified, of a straight, branched or cyclic configuration. Examples of alkylthio groups include methylthio, propylthio, isopropylthio, etc. By way of illustration, the propylthio group signifies —SCH₂CH₂CH₃.

Halo includes F, Cl, Br and I.

Examples of HET¹ include pyridine, pyrimidine, pyridazine, furan, thiophene, thiazole and oxazole.

Examples of HET² include butyrolactone, tetrahydrofuran, tetrahydropyran, 2-pyrrolidinone, pyridine and pyrimidine.

Examples of HET³ include 1,2,3-oxadiazole, 1,2,4-oxadiazole, 1,3,4-oxadiazole, 1,2,3-thiadiazole, 1,2,4-thiadiazole, 1,3,4-thiadiazole, thiophene, pyrrole, pyridine, tetrazole, oxazole, thiazole, 1,2,3-triazole, 1,2,4-triazole and 1,3,4-triazole.

For purposes of this specification, the following abbreviations have the indicated meanings:

| | |
|---|---|
| AcOH = | acetic acid |
| Alloc = | allyloxycarbonyl |
| APCI = | atmospheric pressure chemical ionization |
| BOC = | t-butyloxycarbonyl |
| CBZ = | carbobenzoxy |
| DCC = | 1,3-dicyclohexylcarbodiimide |
| DIBAL = | diisobutyl aluminum hydride |
| DIEA = | N,N-diisoproylethylamine |
| DMAP = | 4-(dimethylamino)pyridine |
| EDCI = | 1-(3-dimethylaminopropyl)-3-ethylcarbodiimide hydrochloride |

-continued

| | |
|---|---|
| EDTA = | ethylenediaminetetraacetic acid, tetrasodium salt hydrate |
| ESI = | electrospray ionization |
| FAB = | fast atom bombardment |
| FMOC = | 9-fluorenylmethoxycarbonyl |
| HMPA = | hexamethylphosphoramide |
| HATU = | O-(7-Azabenzotriazol-1-yl)N,N,N',N'-tetramethyluronium hexafluorophosphate |
| HOBt = | 1-hydroxybenzotriazole |
| HRMS = | high resolution mass spectrometry |
| ICl = | iodine monochloride |
| IBCF = | isobutyl chloroformate |
| KHMDS = | potassium hexamethyldisilazane |
| LDA = | lithium diisopropylamide |
| MCPBA = | metachloroperbenzoic acid |
| Ms = | methanesulfonyl = mesyl |
| MsO = | methanesulfonate = mesylate |
| NBS = | N-bromosuccinimide |
| NMM = | 4-methylmorpholine |
| PCC = | pyridinium chlorochromate |
| PDC = | pyridinium dichromate |
| Ph = | phenyl |
| PPTS = | pyridinium p-toluene sulfonate |
| pTSA = | p-toluene sulfonic acid |
| r.t. = | room temperature |
| rac. = | racemic |
| TFA = | trifluoroacetate |
| TfO = | trifluoromethanesulfonate = triflate |
| TLC = | thin layer chromatography |

Alkyl group abbreviations:

| | |
|---|---|
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |

L-amino acids and abbreviations:

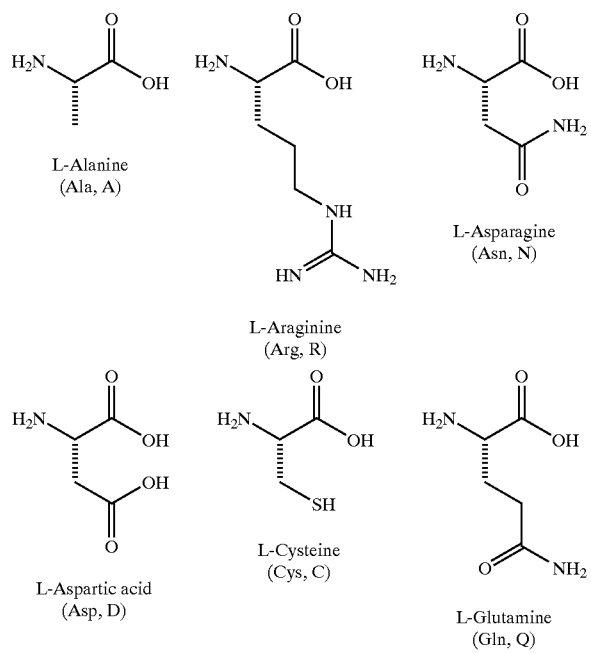

-continued
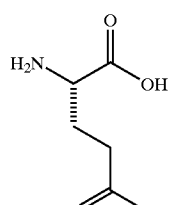
L-Glutamic acid
(Glu, E)
Glycine
(Gly, G)
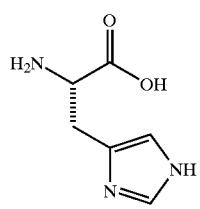
L-Histidine
(His, H)
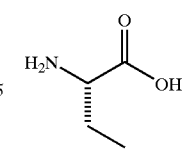
L-Serine
(Ser, S)
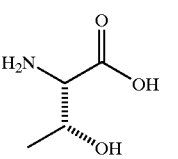
L-Threonine
(Thr, T)
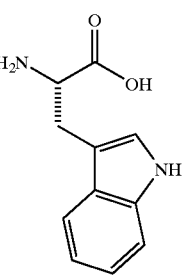
L-Tryptophane
(Trp, W)
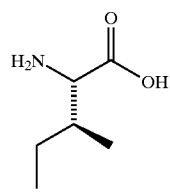
L-Isoleucine
(Ile, I)
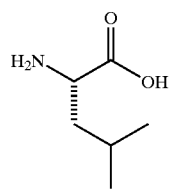
L-Leucine
(Leu, L)
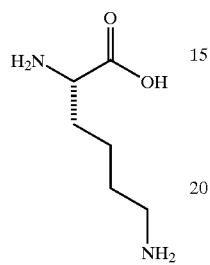
L-Lysine
(Lys, K)
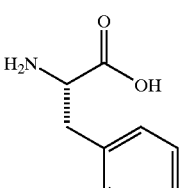
L-Tyrosine
(Tyr, Y)
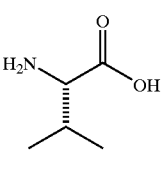
L-Valine
(Val, V)
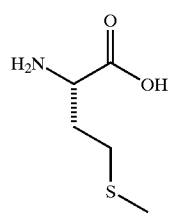
L-Methionine
(Met, M)
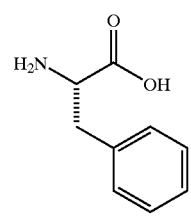
L-Phenylalanine
(Phe, F)
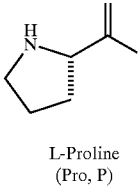
L-Proline
(Pro, P)
Representative examples of compounds of Formula I are found in Table I below.
| Example # | Structure | m/z |
|---|---|---|
| 1 | 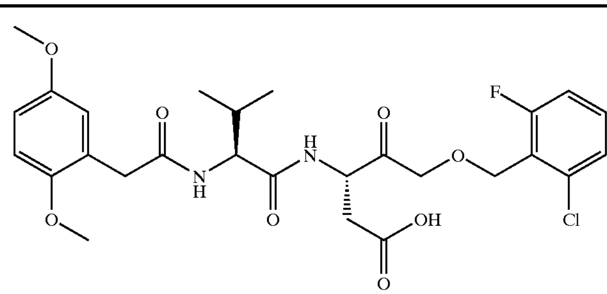 | −APCI: 564.9 (M − 1)⁻ |
| 2 | 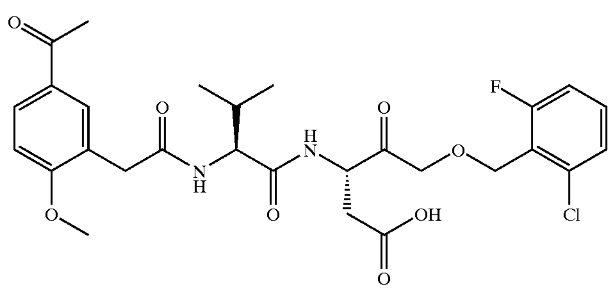 | −APCI: 577.5 (M − 1)⁻ |

-continued
| Example # | Structure | m/z |
|---|---|---|
| 3 | 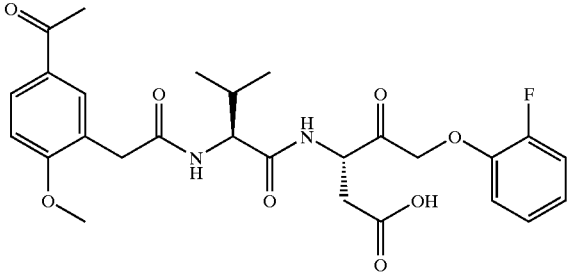 | +APCI: 531.3 (M + 1)+ |
| 4 | 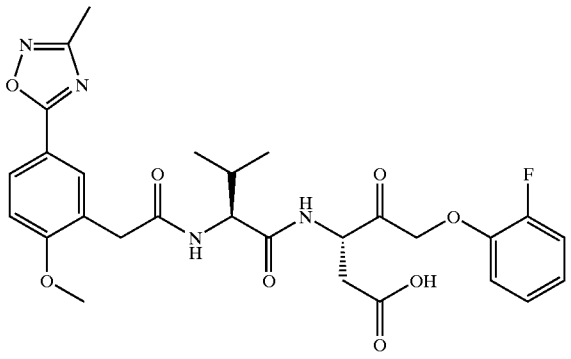 | −APCI: 569.5 (M − 1)− |
| 5 | 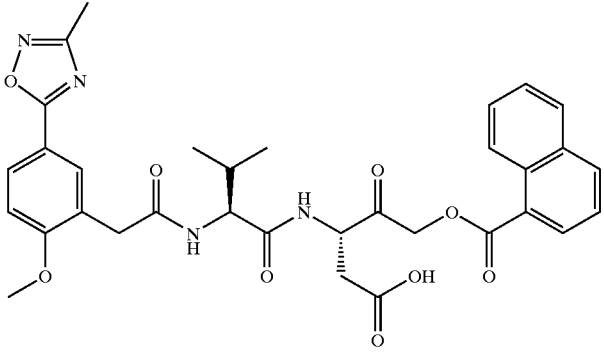 | +ESI: 631.0 (M + 1)+ |
| 6 | 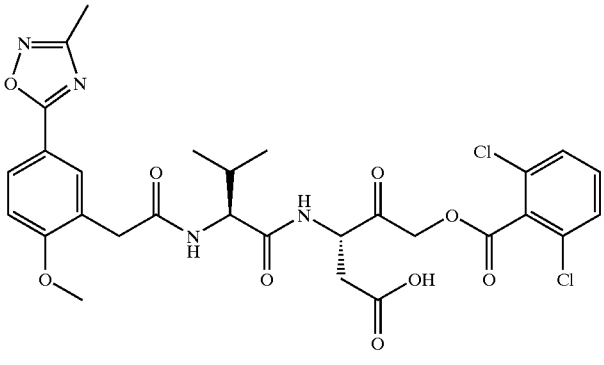 | +ESI: 649.3 (M + 1)+ |

-continued

| Example # | Structure | m/z |
|---|---|---|
| 7 | 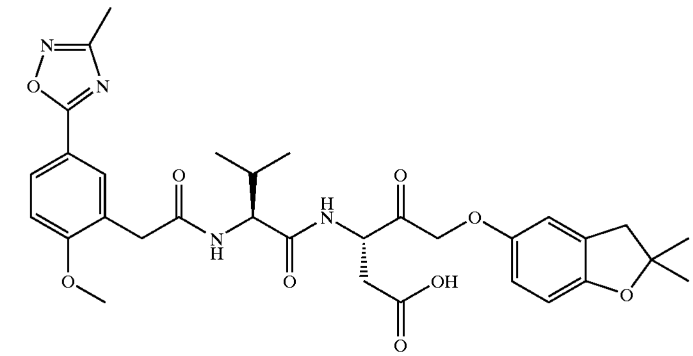 | −APCI: 621.9 (M − 1)− |
| 8 | 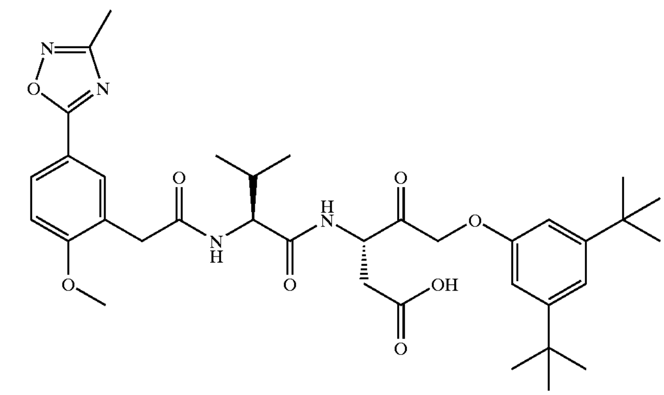 | −APCI: 663.5 (M − 1)− |
| 9 | 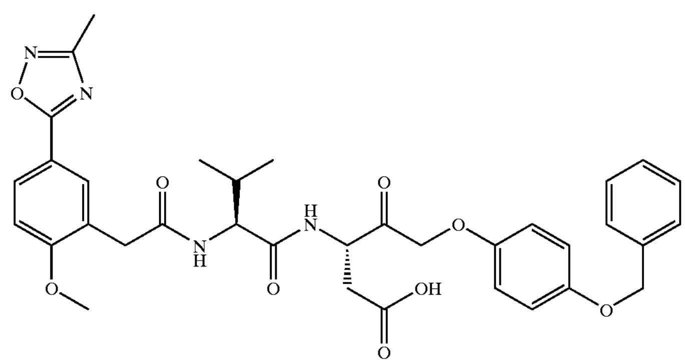 | +ESI: 659.4 (M + 1)+ |
| 10 | 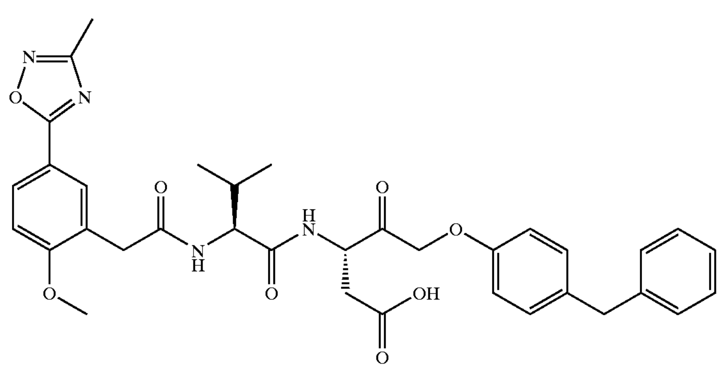 | −APCI: 641.4 (M − 1)− |

-continued
| Example # | Structure | m/z |
|---|---|---|
| 11 | 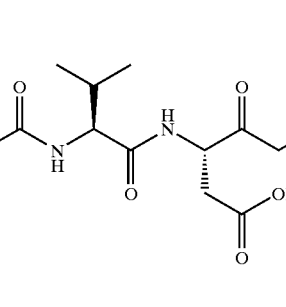 | -APCI: 597.5 (M − 1)⁻ |
| 12 | 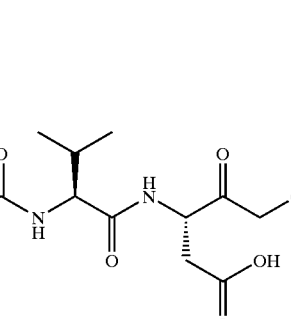 | -APCI: 601.3 (M − 1)⁻ |
| 13 | 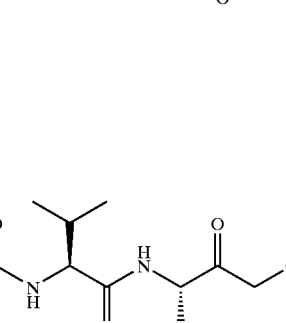 | -APCI: 649.4 (M − 1)⁻ |
| 14 | 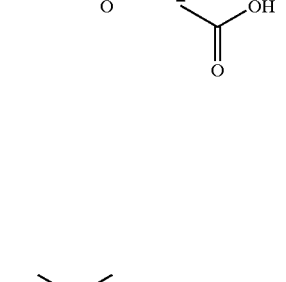 | -APCI: 609.5 (M − 1)⁻ |

-continued

| Example # | Structure | m/z |
|---|---|---|
| 15 | 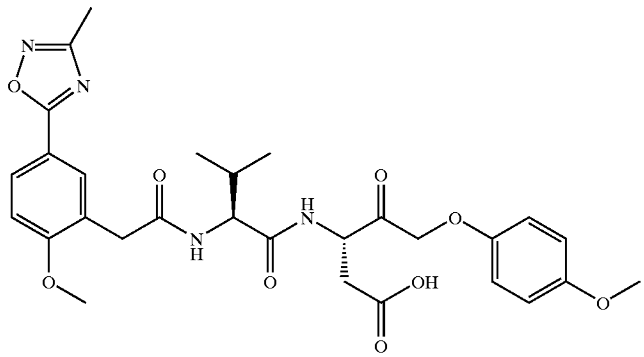 | −APCI: 581.7 (M − 1)⁻ |
| 16 | 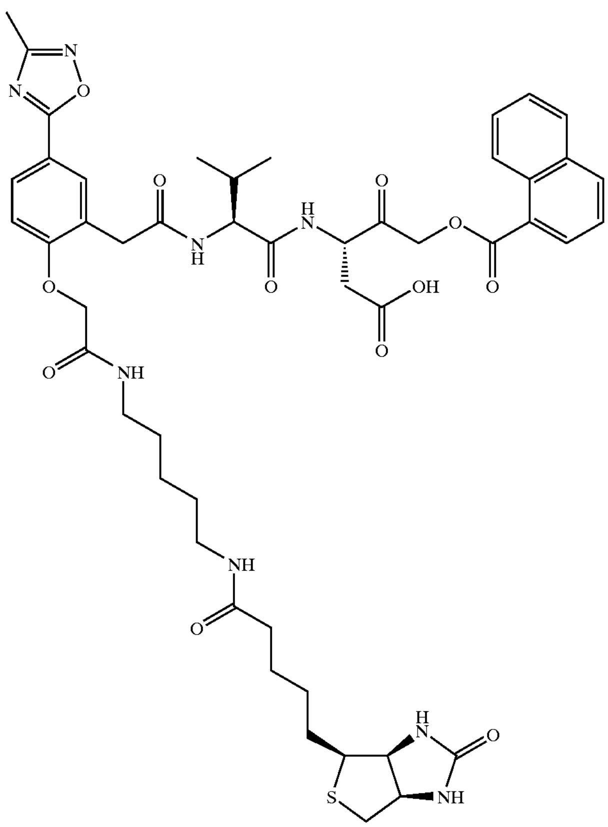 | −APCI: 983.7 (M − 1)⁻ |
| 17 | 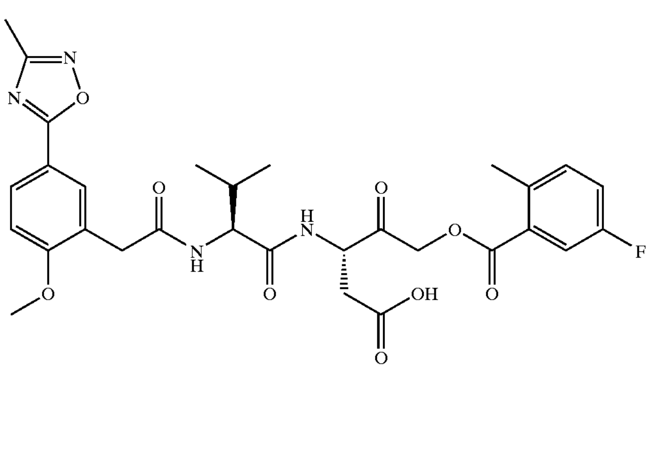 | +APCI: 613.2 (M + 1)⁺ |

-continued

| Example # | Structure | m/z |
|---|---|---|
| 18 | 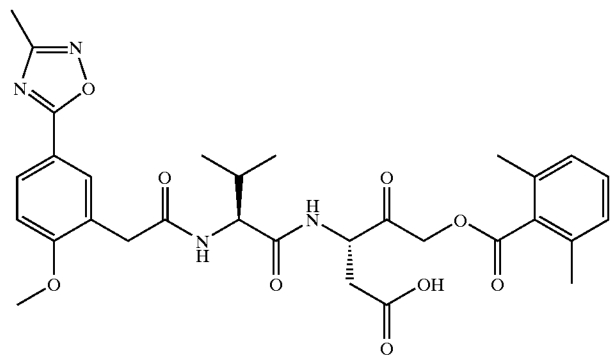 | −APCI: 607.9 (M − 1)⁻ |
| 19 | 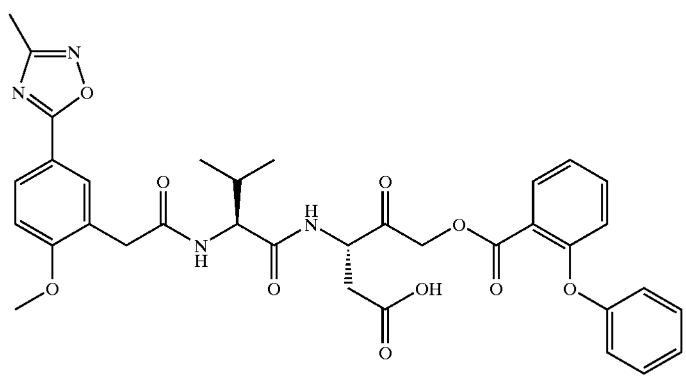 | −APCI: 671.6 (M − 1)⁻ |
| 20 | 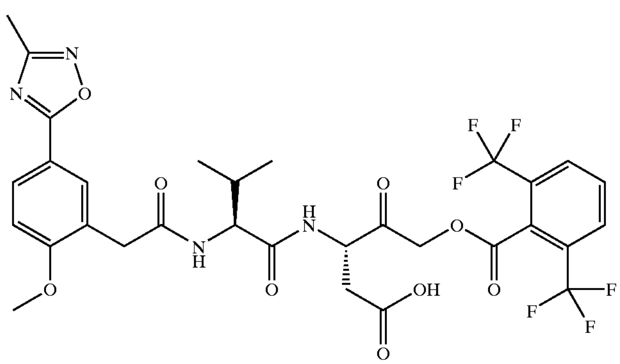 | −APCI: 715.5 (M − 1)⁻ |
| 21 | 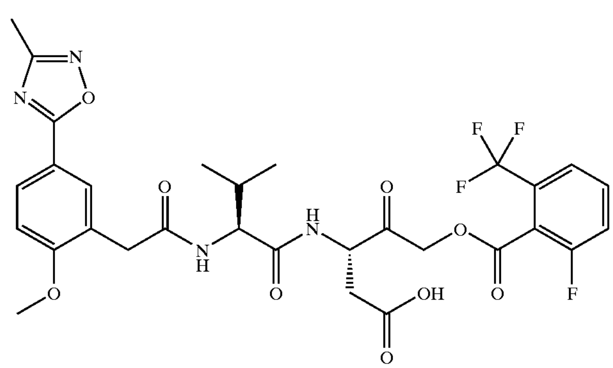 | −APCI: 665.3 (M − 1)⁻ |

-continued

| Example # | Structure | m/z |
|---|---|---|
| 22 | 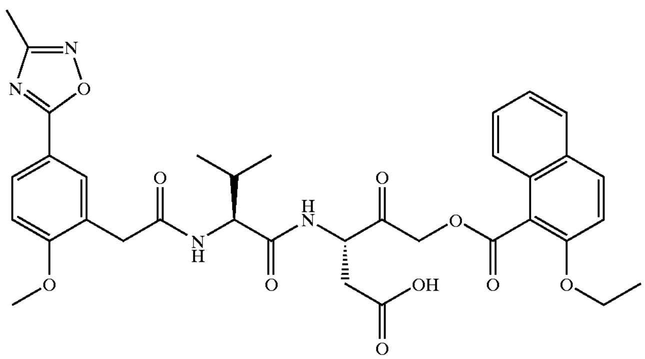 | −APCI: 673.3 (M − 1)− |
| 23 | 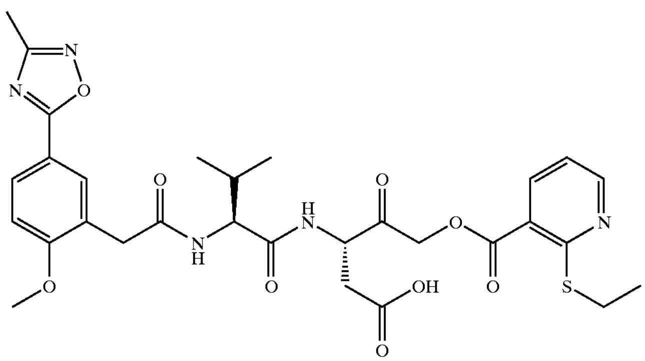 | −APCI: 640.2 (M − 1)− |
| 24 | 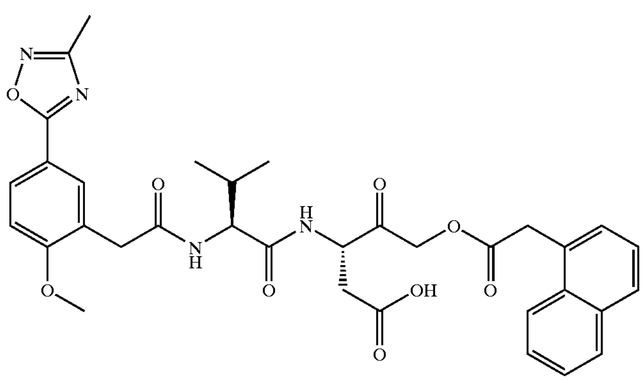 | −APCI: 643.2 (M − 1)− |
| 25 | 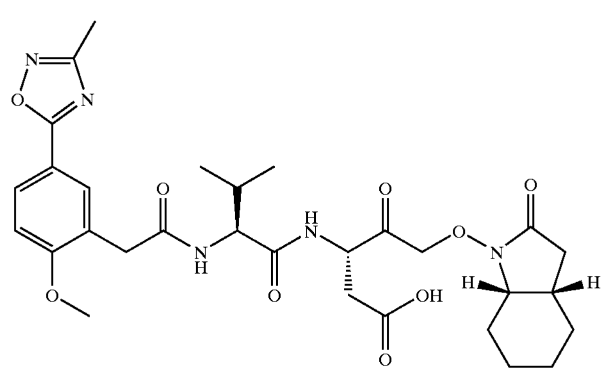 | +APCI: 614.3 (M + 1)+ |

-continued
| Example # | Structure | m/z |
|---|---|---|
| 26 | 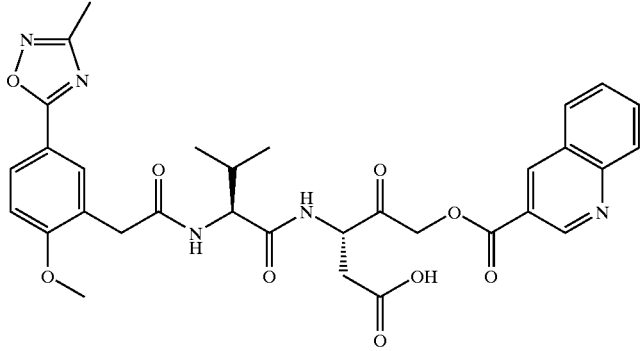 | +APCI: 632.5 (M + 1)+ |
| 27 | 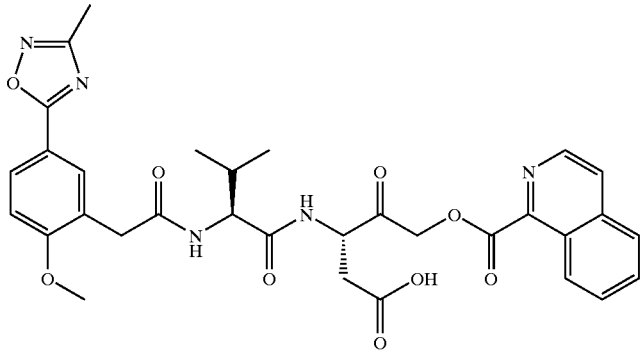 | +ESI: 632.1 (M + 1)+ |
| 28 | 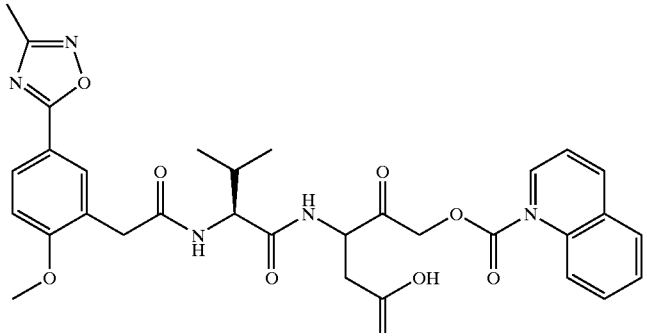 | +ESI: 632.2 (M + 1)+ |
| 29 | 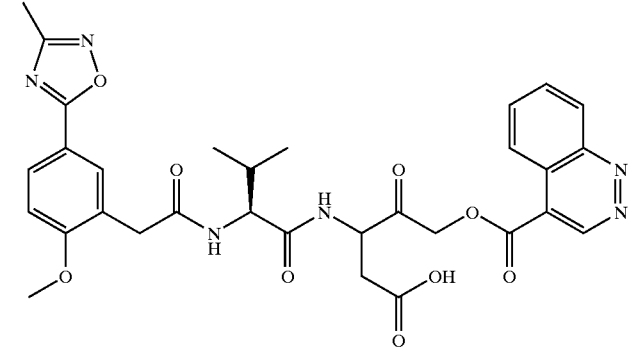 | +ESI: 633.1 (M + 1)+ |

-continued

| Example # | Structure | m/z |
|---|---|---|
| 30 | 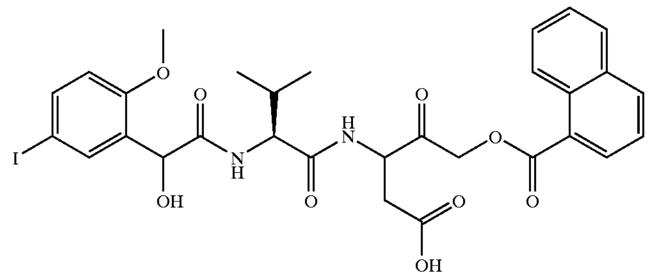 | +APCI: 691 (M + 1)+ |
| 31 | 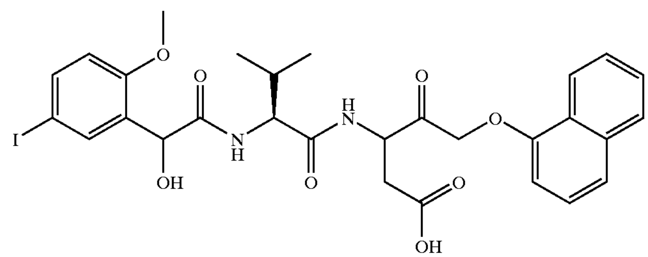 | +APCI: 663 (M + 1)+ |
| 32 | 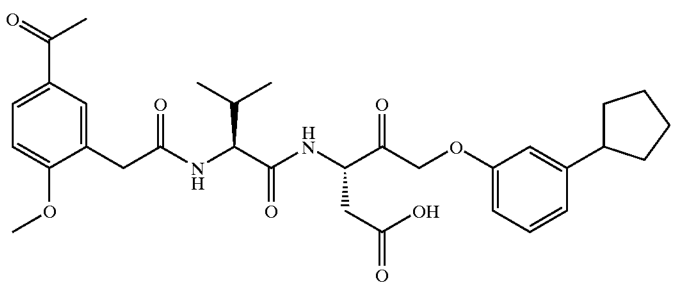 | −APCI: 579.5 (M − 1)− |
| 33 | 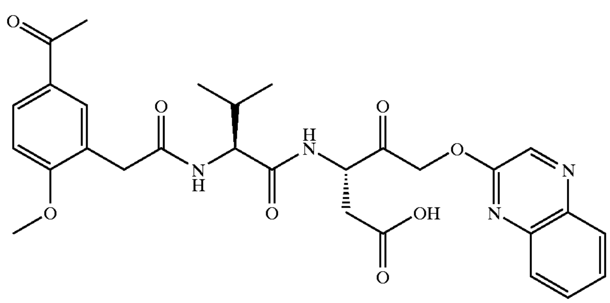 | −APCI: 563 (M − 1)− |
| 34 | 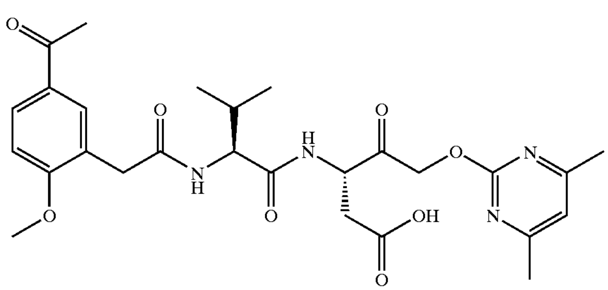 | −APCI: 541.2 (M − 1)− |

-continued

| Example # | Structure | m/z |
|---|---|---|
| 35 | 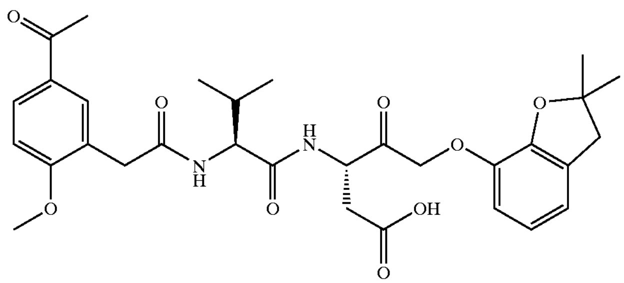 | −APCI: 581.5 (M − 1)⁻ |
| 36 | 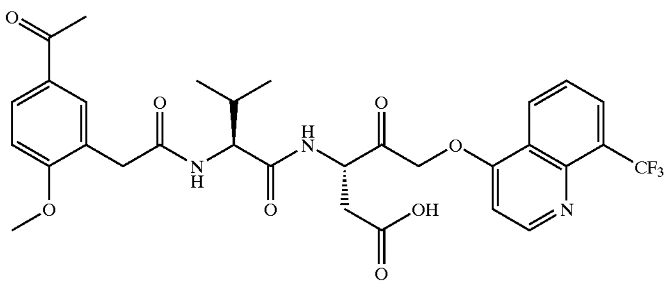 | −APCI: 630.6 (M − 1)⁻ |
| 37 | 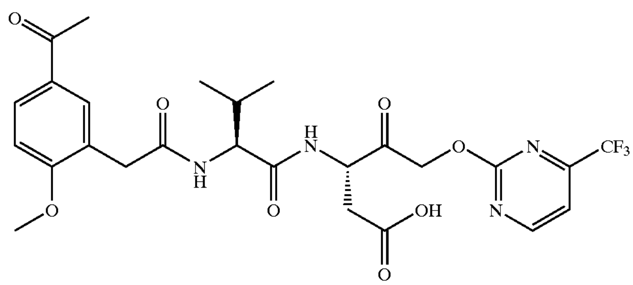 | −APCI: 581.0 (M − 1)⁻ |
| 38 | 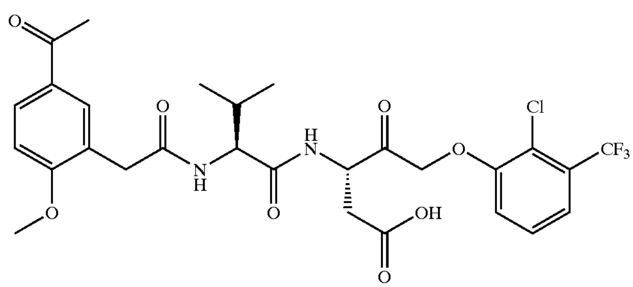 | −APCI: 613.2 (M − 1)⁻ |
| 39 | 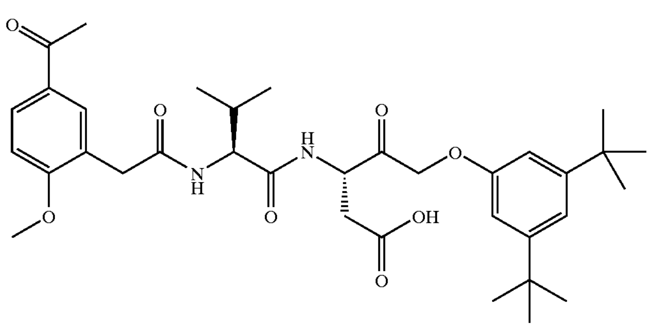 | −APCI: 623.9 (M − 1)⁻ |

| Example # | Structure | m/z |
|---|---|---|
| 40 | 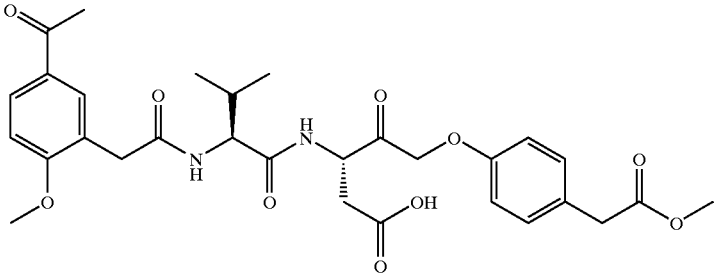 | −APCI: 583.4 (M − 1)⁻ |
| 41 | 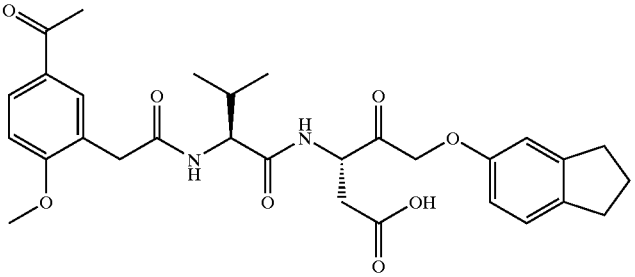 | −APCI: 551.4 (M − 1)⁻ |
| 42 | 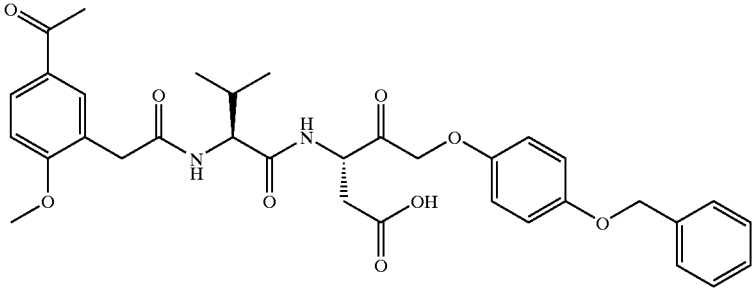 | −APCI: 617.0 (M − 1)⁻ |
| 43 | 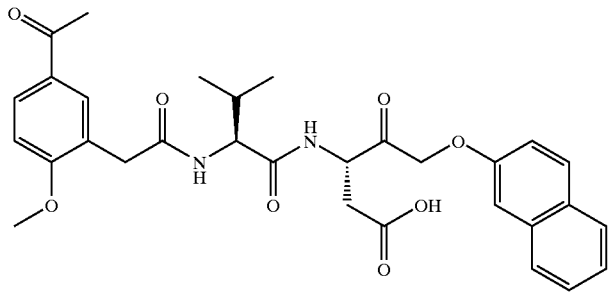 | −APCI: 561 (M − 1)⁻ |
| 44 | 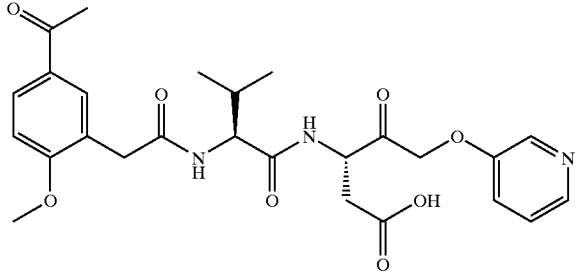 | −APCI: 512.1 (M − 1)⁻ |

-continued

| Example # | Structure | m/z |
|---|---|---|
| 45 | 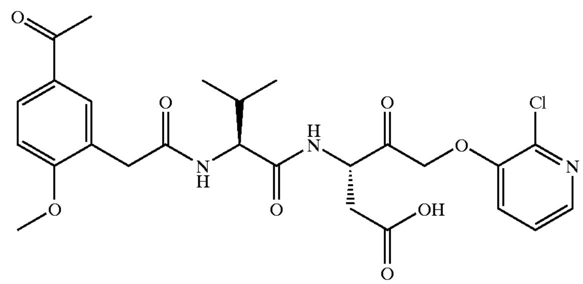 | −APCI: 546.5 (M − 1)− |
| 46 | 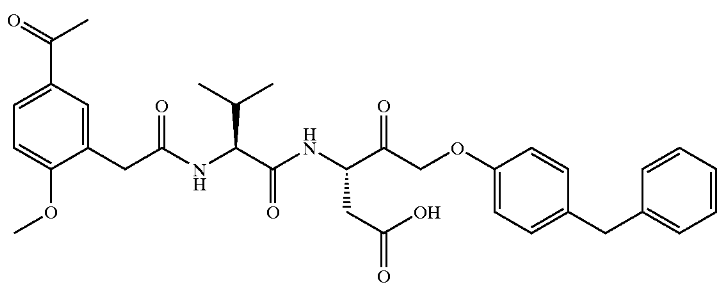 | −APCI: 601.6 (M − 1)− |
| 47 | 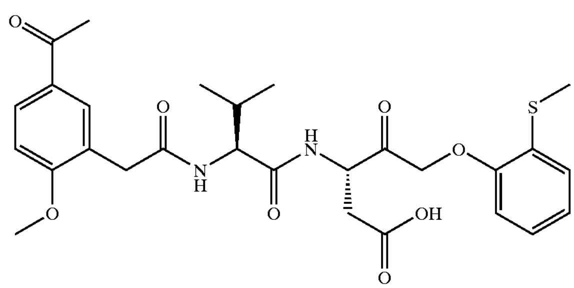 | −APCI: 557 (M − 1)− |
| 48 | 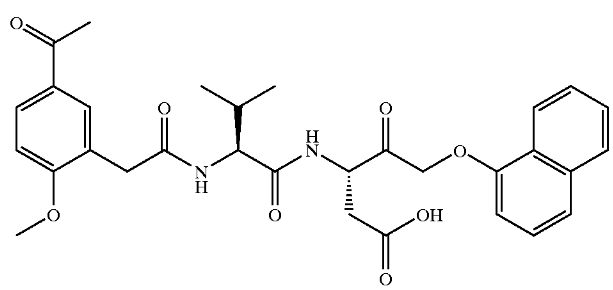 | −APCI: 561.3 (M − 1)− |
| 49 | 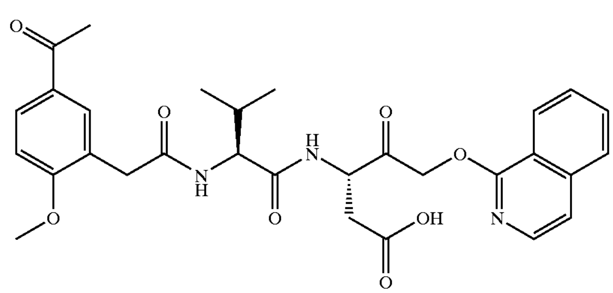 | −APCI: 562.3 (M − 1)− |

-continued
| Example # | Structure | m/z |
|---|---|---|
| 50 | 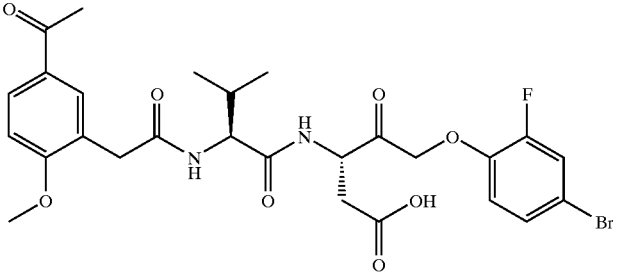 | −APCI: 607.3 (M − 1)⁻ |
| 51 | 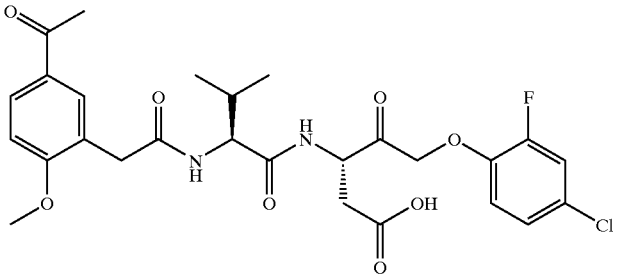 | −APCI: 563.3 (M − 1)⁻ |
| 52 | 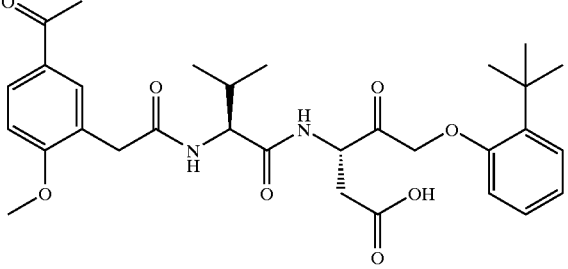 | −APCI: 567.3 (M − 1)⁻ |
| 53 | 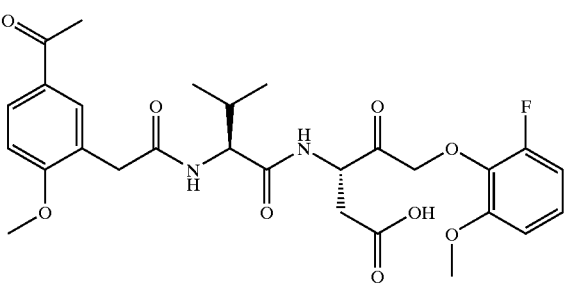 | −APCI: 559.2 (M − 1)⁻ |
| 54 | 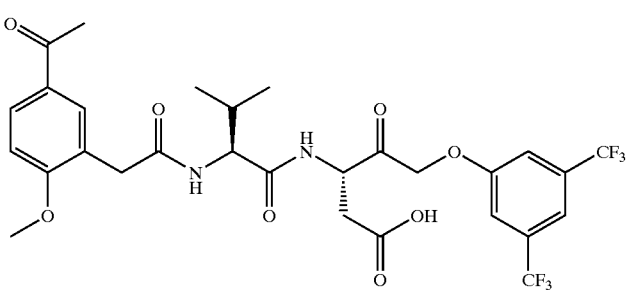 | −APCI: 647.6 (M − 1)⁻ |

-continued
| Example # | Structure | m/z |
|---|---|---|
| 55 | 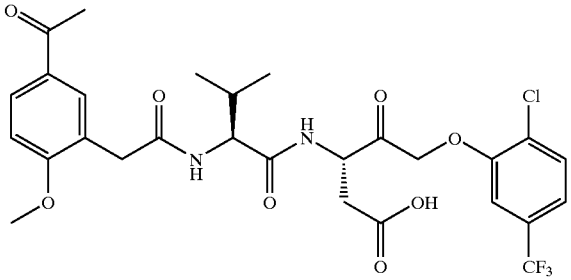 | −APCI: 613.2 (M − 1)⁻ |
| 56 | 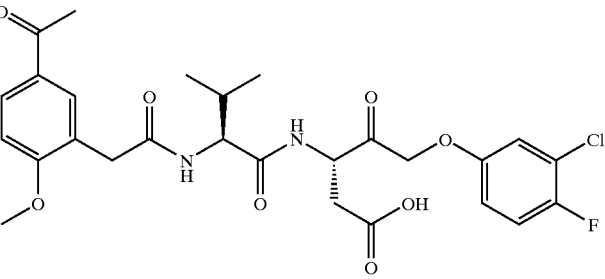 | −APCI: 563.0 (M − 1)⁻ |
| 57 | 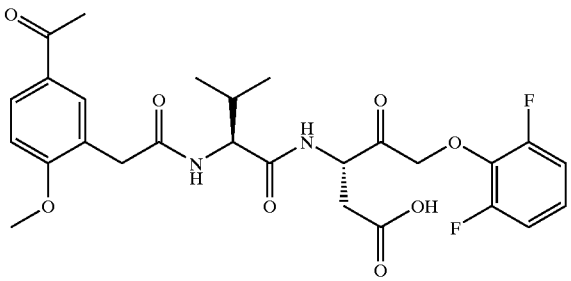 | +ESI: 549.1 (M + 1)⁺ |
| 58 | 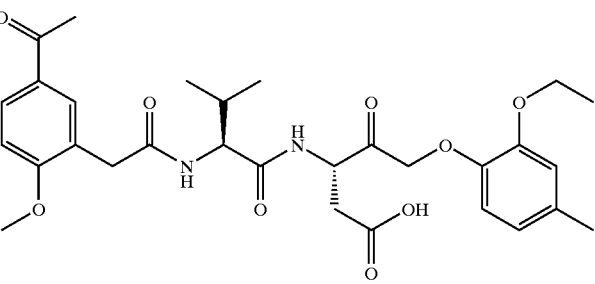 | −APCI: 569.6 (M − 1)⁻ |
| 59 | 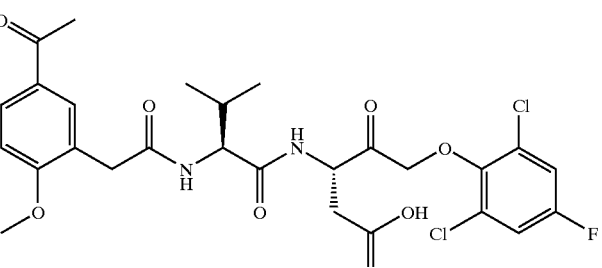 | −APCI: 597.1 (M − 1)⁻ |

-continued
| Example # | Structure | m/z |
|---|---|---|
| 60 | 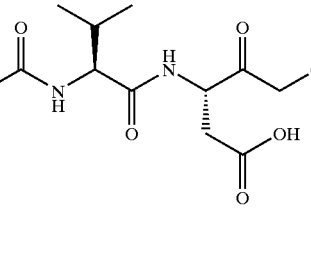 | −APCI: 597.2 (M − 1)⁻ |
| 61 | 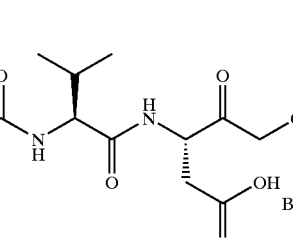 | +ESI: 689.0 (M + 1)⁺ |
| 62 | 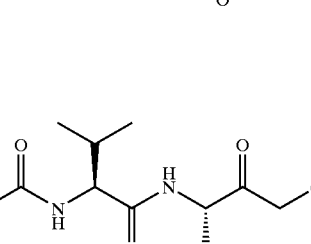 | |
| 63 | 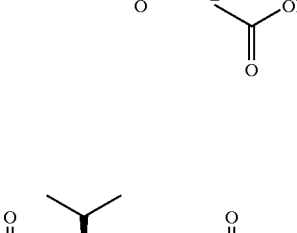 | +ESI: 603.1 (M + 1)⁺ |
| 64 | 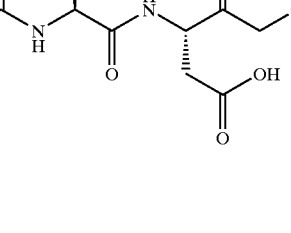 | −APCI: 571.5 (M − 1)⁻ |

| Example # | Structure | m/z |
|---|---|---|
| 65 | 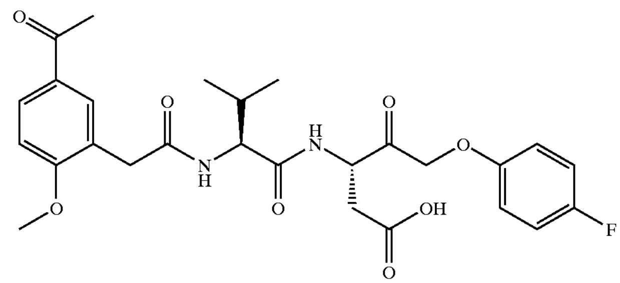 | -APCI: 529.3 (M − 1)⁻ |
| 66 | 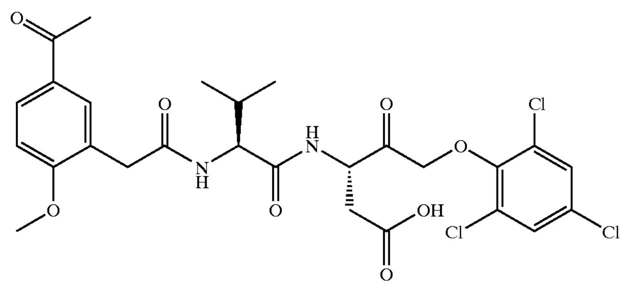 | +ESI: 615.7 (M + 1)⁺ |
| 67 | 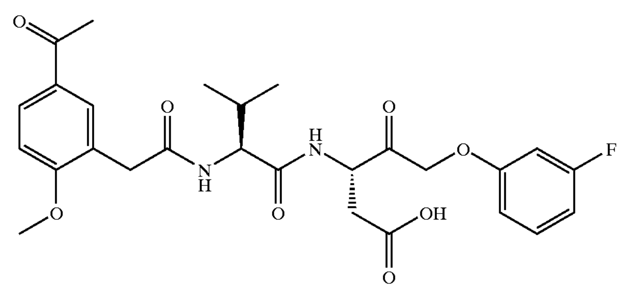 | -APCI: 529.3 (M − 1)⁻ |
| 68 | 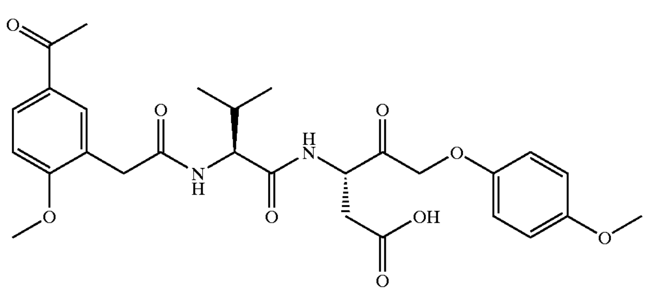 | -APCI: 541.5 (M − 1)⁻ |

The compounds described herein, and in particular, in Table I, are intended to include salts, enantiomers, esters and hydrates, in pure form and as a mixture thereof. Also, when a nitrogen atom appears, it is understood sufficient hydrogen atoms are present to satisfy the valency of the nitrogen atom.

While chiral structures are shown below, by substituting into the synthesis schemes an enantiomer other than the one shown, or by substituting into the schemes a mixture of enantiomers, a different isomer or a racemic mixture can be achieved. Thus, all such isomers and mixtures are included in the present invention.

The compounds described typically contain asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

This invention also encompasses a pharmaceutical composition comprised of a compound of Formula I in combination with a pharmaceutically acceptable carrier.

This invention also encompasses a method of treating or preventing a caspase-3 mediated disease or condition in a mammalian patient in need of such treatment, comprising administering to said patient a compound of Formula I in an amount effective to treat or prevent said caspase-3 mediated disease.

Another embodiment of the invention encompasses the method of treating or preventing a caspase-3 mediated disease wherein the disease or condition is selected from the group consisting of:

cardiac or cerebral ischemia/reperfusion injury, type I diabetes, immune deficiency syndrome, AIDS, cerebral and spinal cord trauma injury, organ damage during transplantation, alopecia, aging, Parkinson's disease, Alzheimer's disease, Down's syndrome, spinal muscular atrophy, multiple sclerosis and neurodegenerative disorders.

Another embodiment of the invention encompasses the method of treating or preventing a caspase-3 mediated disease wherein the disease or condition is selected from cardiac and cerebral ischemia/reperfusion injury, spinal cord injury and organ damage during transplantation.

Another embodiment of the invention encompasses the method of treating or preventing a caspase-3 mediated disease wherein the disease or condition is a chronic disorder selected from the group consisting of: a neurodegenerative disease selected from Alzheimer's, polyglutamine-repeat disorders, Down's syndrome, spinal muscular atrophy, multiple sclerosis, immunodeficiency, HIV, diabetes, alopecia and aging.

Another embodiment of the invention encompasses the method of treating or preventing a caspase-3 mediated disease wherein the disease or condition is selected from the group consisting of: cardiac or cerebral ischemia or reperfusion injury, type I diabetes, immune deficiency syndrome or AIDS, cerebral or spinal cord trauma injury, organ damage during transplantation, alopecia, aging, Parkinson's disease, Alzheimer's disease, Down's syndrome, spinal muscular atrophy, multiple sclerosis, neurodegenerative disorders, sepsis and bacterial meningitis.

The pharmaceutical compositions of the present invention comprise a compound of Formula I as an active ingredient or a pharmaceutically acceptable salt thereof in combination with a pharmaceutically acceptable carrier, and optionally other therapeutic ingredients. The term "pharmaceutically acceptable salts" refers to salts prepared from pharmaceutically acceptable bases including inorganic bases and organic bases. Representative salts derived from inorganic bases include aluminum, ammonium, calcium, copper, ferric, ferrous, lithium, magnesium, manganic salts, manganous, ammonium, potassium, sodium, zinc and the like. Particularly preferred are the calcium, magnesium, potassium, and sodium salts. Representative salts derived from pharmaceutically acceptable organic bases include salts of primary, secondary and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabarnine, isopropylamine, lysine, methylglucamine, morpholine, piperazine, piperidine, polyamine resins, procaine, purines, theobromine, triethylamine, trimethylamine, tripropylamine, trometharnine and the like.

When the compound of the present invention is basic, salts may be prepared from pharmaceutically acceptable non-toxic acids, including inorganic and organic acids. Examples of such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric and tartaric acids.

In the discussion of methods of treatment that follows, reference to the compounds of Formula I are meant to also include the pharmaceutically acceptable salts.

The ability of the compounds of Formula I to inhibit caspase-3 make them useful research tools in the field of apoptosis.

The magnitude of therapeutic dose of a compound of Formula I will, of course, vary with the nature of the severity of the condition to be treated and with the particular compound of Formula I and its route of administration and vary upon the clinician's judgement. It will also vary according to the age, weight and response of the individual patient. An effective dosage amount of the active component can thus be determined by the clinician after a consideration of all the criteria and using is best judgement on the patient's behalf. A representative dose will range from 0.001 mpk/d to about 100 mpk/d.

An ophthalmic preparations for ocular administration comprising 0.001–1% by weight solutions or suspensions of the compounds of Formula I in an acceptable ophthalmic formulation may be used.

Any suitable route of administration may be employed for providing an effective dosage of a compound of the present invention. For example, oral, parenteral and topical may be employed. Dosage forms include tablets, troches, dispersions, suspensions, solutions, capsules, creams, ointments, aerosols, and the like.

The compositions include compositions suitable for oral, parenteral and ocular (ophthalmic). They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration. In preparing the compositions for oral dosage form, any of the usual pharmaceutical media may be employed, such as, for example, water, alcohols, oils, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case or oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil emulsion. Such compositions may be prepared by any of the methods of pharmacy but all methods include the step of bringing into active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. For example, each dosage unit may contain from about 0.01 mg to about 1.0 g of the active ingredient.

Methods of Synthesis

The compounds of the present invention are prepared using the general procedures described below:

Bromomethyl ketone 1 is prepared as illustrated in Scheme 1. Reaction of N-fluorenylmethyloxycarbonyl-L-aspartic acid β-tert-butyl ester (Fmoc-L-Asp (OtBu)—OH) (2) (Novabiochem) with iso-butyl chloroformate (IBCF) followed by treating the reaction mixture with an excess of diazomethane yields the diazomethyl ketone intermediate 3. This intermediate is subjected in situ to a 1:1 mixture of AcOH and 45% aqueous hydrobromic acid (HBr) to give compound 1 as a white powder.

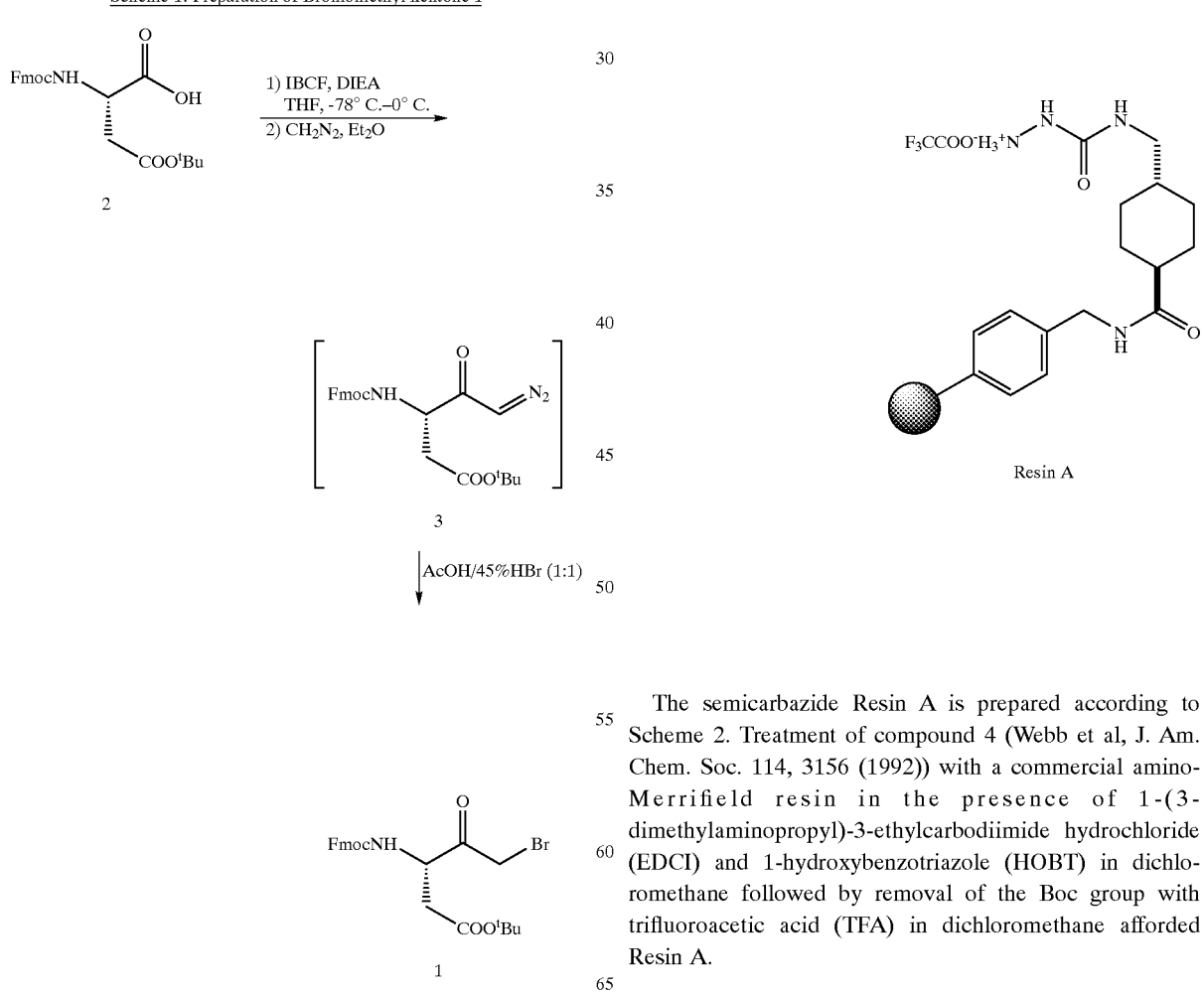

The semicarbazide Resin A is prepared according to Scheme 2. Treatment of compound 4 (Webb et al, J. Am. Chem. Soc. 114, 3156 (1992)) with a commercial amino-Merrifield resin in the presence of 1-(3-dimethylaminopropyl)-3-ethylcarbodiimide hydrochloride (EDCI) and 1-hydroxybenzotriazole (HOBT) in dichloromethane followed by removal of the Boc group with trifluoroacetic acid (TFA) in dichloromethane afforded Resin A.

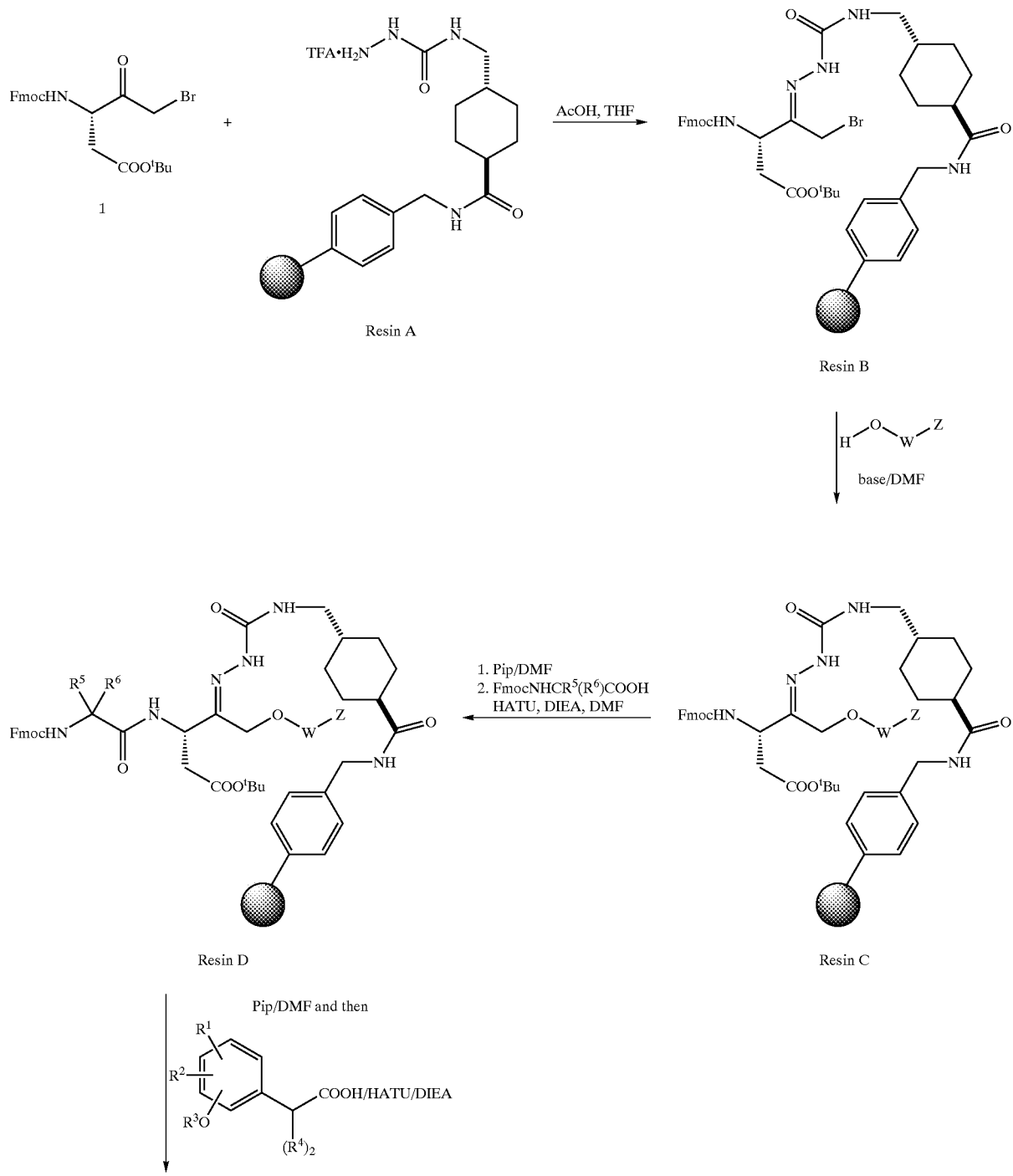
Scheme 3: General scheme for solid phase synthesis of dipeptide I

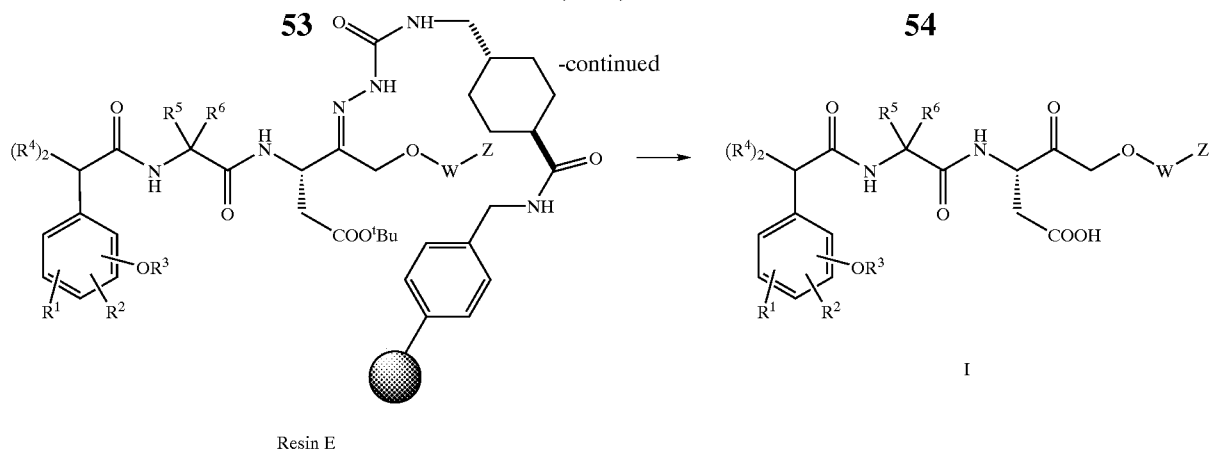

Resin E

The general procedure for solid phase synthesis of dipeptide I incorporating either a phenoxide P1' side chain or a P1' carboxylate side chain is illustrated in Scheme 3. Bromomethyl ketone 1 is reacted with Resin A in THF in the presence of acetic acid to afford Resin B, which is reacted with a phenol or a carboxylic acid in the presence of suitable bases such as potassium fluoride (KF) or $Cs_2CO_3$ in DMF to give Resin C. The Fmoc group in Resin C is removed with 20% (v) piperidine (Pip) in DMF and the resultant resin reacted with $FmocHNCR^5(R^6)COOH$ using O-(7-Azabenzotriazol-1-yl)N,N,N',N'-tetramethyluronium hexafluorophosphate (HATU) as the activating agent and diisopropylethylamine (DIEA) as the base, affording Resin D. The Fmoc group in Resin D is cleaved similarly and then the amino group released is reacted with acid 5 as shown to yield Resin E. The final dipeptide I is released from the solid support by treating Resin D with trifluoroacetic acid (TFA) in water (9/1, v/v). This scheme does not enable the preparation of certain P1' carboxylate analogs.

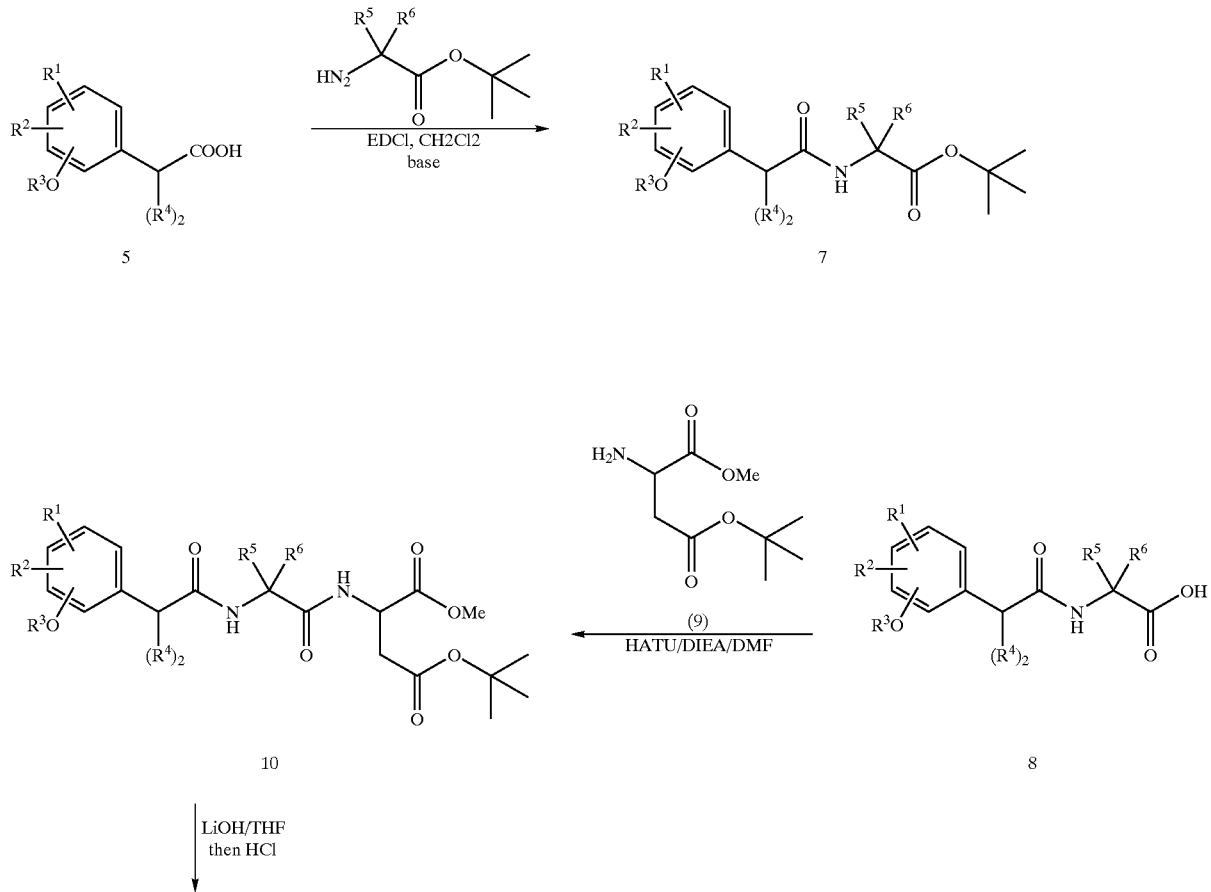

Scheme 4: General scheme for solution phase synthesis of compound I

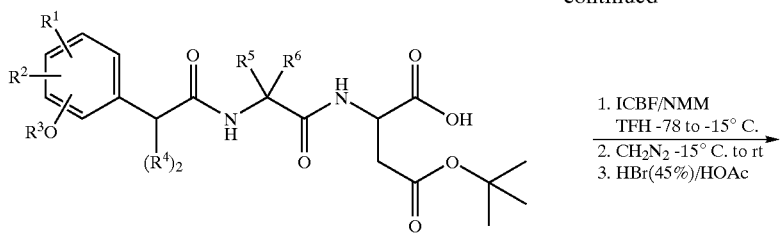

11

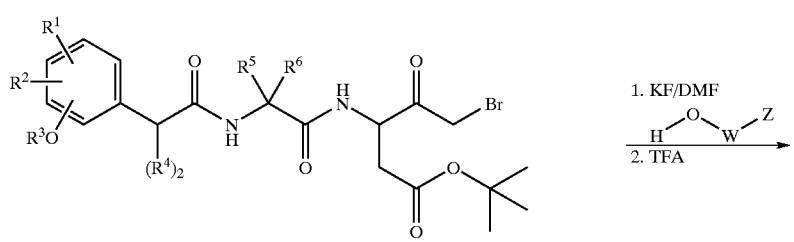

12

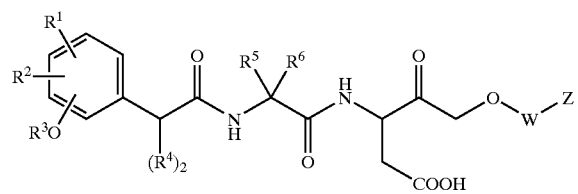

I

The solution phase synthesis of compound I is outlined in Scheme 4. Acid 5 is first reacted with an appropriate amine 6 using EDCI as the coupling reagent to give amide 7. The t-butyl ester in 7 is cleaved with trifluoroacetic acid to yield carboxylic acid 8, which is further reacted with β-t-butyl aspartic acid methyl ester (9) in the presence of HATU and diisopropylethylamine, giving product 10. The methyl ester in is hydrolyzed using LiOH in ThF and acid 11 thus obtained is reacted with iso-butyl chloroformate in the presence of N-methylmorpholine. The mixed anhydride thus generated is reacted with diazomethane in situ. The mixture is then treated with a solution of 45% HBr in glacial acetic acid (1:1, v/v) to afford bromomethyl ketone 12. Reaction of 12 with a suitable phenol or carboxylic acid in the presence of bases such as KF or $Cs_2CO_3$ followed by cleavage of the t-butyl ester with TFA furnish the final product I.

The invention is further illustrated using the following non-limiting examples.

EXAMPLE 1

(3S)-5-[(2-Chloro-6-fluorobenzyl)oxy]-3-{[(2S)-2-{ [(2,5-dimethoxyphenyl)acetyl]amino}-3- methylbutanoyl]amino}-4-oxo-pentanoic Acid

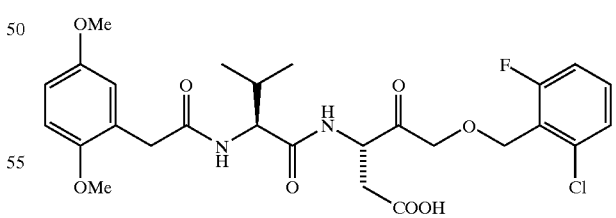

Step 1: Preparation of Resin A

A suspension of amino-Merrified resin (Novabiochem, 30 grams, 31.2 mmol), acid 4 (14.7 g, 46.8 mmol), EDCI (10.77 g, 56.12 mmol) and HOBT (8.6 g, 56.16 mmol) in DMF (240 mL) was shaken on a orbital shaker at 190 rpm overnight. The mixture was filtered and the residual resin washed sequentially with DMF, methanol, dichloromethane and methanol and dried under vacuum. The resin was suspended in a solution of TFA/dichloromethane (1:2, 300 mL) and shaken for 2 hours on an orbital shaker. The suspension was filtered, washed with dichloromethane (5×) and methanol (5×) and then dried under vacuum overnight to yield Resin A (40.5 g, 0.81 mmol/g).

Step 2: the Title Compound

A suspension of Resin A (0.9 g) and t-butyl N-(allyloxycarbonyl)-3-amino-5-(2-chloro-6-fluorophenylmethoxy)4-oxo-pentanoate (prepared in a similar manner as described in a prior art, see: Bemis, G. W. et al, U.S. Pat. No. 5,656,627) (0.35 g) in THF in the presence of AcOH (0.015 mL) was mixed in a fritted reservoir overnight. The mixture was filtered and the residual resin was washed with THF and dichloromethane, and then dried under vacuum. The de-protection of the alloc group was carried out according to a literature procedure by Thieriet, N. et al (Tetrahedron Lett. 38, 7275 (1997)). Thus, a portion (0.3 g) of the resin obtained above was suspended in dichloromethane (6 mL) under nitrogen in a fritted reservoir. To the suspension was added phenylsilane (0.41 mL) and a solution of Pd(PPh$_3$)$_4$ (0.019 g) in dichloromethane (2 mL). The reservoir was rotated for 10 mninute and the solvent was removed by vacuum filtration. The residual resin was washed with dichloromethane and re-subjected to the above condition. This resin was reacted with Fmoc-Valine-OH (0.28 g) and HATU (0.32 g) and DIEA (0.14 mL) in DMF (4 mL) for 2 hours and washed with DMF. The resulting resin was then treated with a solution of 20% (v) piperidine in DMF and washed again with DMF, methanol, dichloromethane and methanol and dried under vacuum. The resin thus obtained was treated with 2,5-dimethoxyphenylacetic acid (0.27 g), HATU (0.32 g) and DIEA (0.14 mL) in DMF (4 mL) for 2 hours and washed sequentially with DMF, methanol, dichloromethane, ethyl acetate and ether. A cocktail consisting of TFA and water (9:1, 10 mL) was then added and the mixture rotated for 1 h and filtered. The filtrate was collected and residual resin washed with dichloromethane and acetonitrile. The filtrate and washing solutions were combined, concentrated in vacuo and triturated with ether to afford the title compound. $^1$H NMR (400 MHz, acetone-d$_6$): δ 7.70 (bs, 1H, NH), 7.40 (m, 1H), 7.30 (d, 1H), 7.13 (t, 1H), 7.04 (bs, 1H, NH), 6.90–6.83 (m, 2H), 6.77 (m, 1H), 4.80 (m, 1H), 4.74 (m, 2H), 4.35–4.23 (m, 1H), 3.80 (s, 3H), 3.68 (s, 3H), 3.53 (d, 1H), 3.49 (d, 1H), 2.88–2.68 (m, 2H), 0.90–0.80 (m, 6H); MS (−APCI): 546.9 (M−1)$^−$.

EXAMPLE 2

(3S)-3-{[(2S)-2-{[(5-Acetyl-2-methoxyphenyl)acetyl]amino}-3-methylbutanoyl]amino}-5-[(2-chloro-6-fluorobenzyl)oxy]-4-oxo-pentanoic Acid

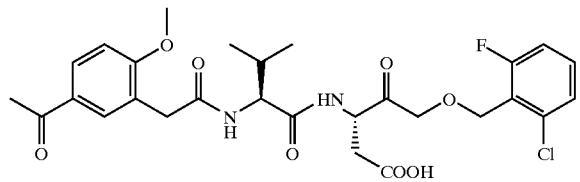

Step 1: Preparation of (5-Acetyl-2-methoxyphenyl)acetic Acid (13)

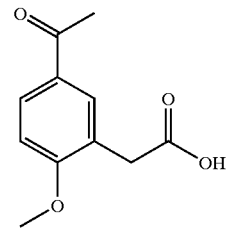

13

A mixture of 5-acetyl-2-methoxybenzyl nitrile in acetic acid (40 mL), concentrated H$_2$SO$_4$ (40 mL) and H$_2$O (40 mL) was heated to 120° C. for 4 hours an cooled to room temperature. The mixture was diluted with water and extracted with ethyl acetate (3×). The organic extracts were combined, washed with water, brine, dried over MgSO$_4$ and concentrated. The crude product was recrystallized from ethyl acetate/hexanes to give the desired product 13 as a white powder. $^1$H NMR (400 MHz, acetone-d$_6$) δ 7.95 (dd, 1H), 7.90 (d, 1H), 7.10 (d, 1H), 3.91 (s, 3H), 3.68 (s, 2H), 2.53 (s, 3H). This acid was processed to the title compound as described in Example 1.

EXAMPLE 4

(3S)-5-(2-Fluorophenoxy)-3-{[(2S)-2-({[2-methoxy-5-(3-methyl-1,2,4-oxadiazol-5-yl)-phenyl]acetyl}amino)-3-methylbutanoyl]amino}-4-oxopentanoic Acid

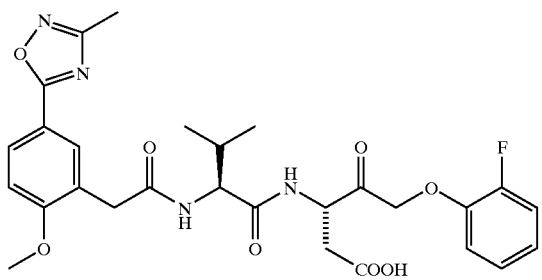

Step 1: Methyl (5-Iodo-2-methoxyphenyl)acetate (14)

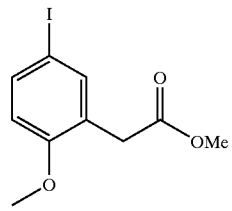

14

To a solution of 2-methoxyphenylacetic acid (14 g, 84 mmol) in dioxane (100 mL) at 0° C. was added ICl (14 g, 86 mmol) in dioxane (50 mL) over a period of 15 min. The mixture was stirred at 0° C. for an additional 15 min and poured to a mixture of water (2 L) and 5% Na$_2$S$_2$O$_3$ (50 mL). After the solution became clear, the solid was collected by vacuum filtration and washed with water. Drying under vacuum afforded 10 g of 5-iodo-2-methoxyphenylaceitc acid. $^1$H NMR (400 MHz, acetone-d$_6$): δ 7.55 (d, 1H), 7.54 (s, 1H), 6.80 (d, 1H), 3.80 (s, 3H), 3.58 (s, 2H). The acid obtained above was added to a solution of acetyl chloride (50 mL) in methanol (500 mL) and the mixture was stirred overnight and then heated to reflux for 2 h. After cooling to room temperature, the mixture was concentrated and the crude product was purified by flash column chromatography. Eluting with EtOAc/Hexanes (1/9) furnished desired product 14 (9 g). $^1$H NMR (400 MHz, acetone-d$_6$): δ 7.58 (d, 1H), 7.55 (s, 1H), 6.82 (d, 1H), 3.80 (s, 3H), 3.60 (s, 3H), 3.58 (s, 2H).

Step 2: Preparation of [2-Methoxy-5-(3-methyl-1,2,4-oxadiazol-5-yl)phenyl]acetic Acid (15)

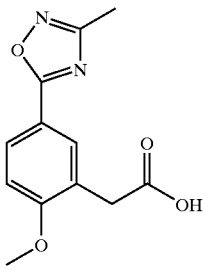

The following reaction was carried out according to the literature procedure (see: Young, J. R. and DeVita R. J., Tetrahedron Lett. 39, 3931 (1998)).

A mixture containing iodide 14 (700 mg, 2.3 mmol), (PPh$_3$)$_2$PdCl$_2$ (322 mg, 0.46 mmol), methylamidoxime (518 mg, 6.9 mmol) and triethylamine (644 mL, 4.6 mmol) in toluene (10 mL) was carefully purged with CO and then heated to 90° C. for 10 h and cooled to room temperature. Concentration of the volatiles gave the crude product which was purified by column chromatography. Eluting with EtOAc/hexanes (1:4) give the desired product as a white solid. $^1$H NMR (400 MHz, acetone-$_6$): δ 8.05 (d, 1H), 8.01 (s, 1H), 7.20 (d, 1H), 3.92 (s, 3H), 3.75 (s, 2H), 3.65 (s, 3), 2.37 (s, 3H). The ester (900 mg) was dissolved in a solution of THF (10 mL), methanol (10 mL) and water (10 mL). To the solution was added LiOH (5 mL, 1M in water) and the mixture was stirred at room temperature for 4 hours, acidified with 1N HCl and extracted with ethyl acetate (3×). The extracts were combined, washed with water and brine, dried over MgSO$_4$ and concentrated to afford the desired acid as a white powder. $^1$H NMR (300 MHz, acetone-d$_6$): δ 8.05 (d, 1H), 8.01 (s, 1H), 7.18 (d, 1H), 3.94 (s, 3H), 3.71 (s, 2H), 2.37 (s, 3H). Step 3: t-Butyl (3S)-5-Bromo-3-[(9H-9-fluorenylmethoxy)carbonyl]amino-4-oxo-pentanoate (1)

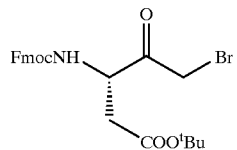

To a solution of N-Fmoc-L-aspartic acid β-t-butyl ester (21.0 g, 51.0 mmol) in 300 mL of tetrahydrofuran (THF) at −78° C. was added N-methylmorpholine (NMM, 7.9 mL, 71.4 mmol) followed by iso-butyl chloroformate (IBCF, 8.6 mL, 66.3 mmol). After stirring for 30 minutes at −78° C., this mixture was warmed to −15° C. for 15 minutes. To the mixture was then added excess amount of diazomethane in ether (1 M) with stirring until a yellow color persisted at room temperature. The solution was then stirred at room temperature for 30 minutes, recooled back to 0° C. and treated with a solution of HBr (45% aqueous)/AcOH (1/1, v/v, 100 mL) for 5 minutes, and diluted with ethyl acetate and water. The organic phase was separated, washed with water and brine, dried over magnesium sulfate, filtered and concentrated. The crude product was purified by flash chromatography. Eluting with hexanes/ethyl acetate (3:1) afforded the desired product as a white powder (20 g, 81% yield). $^1$H NMR (400 MHz, acetone-d$_6$): δ 7.85 (d, 2H), 7.69 (d, 2H), 7.41 (t, 2H), 7.32 (t, 2H), 7.02 (bd, 1H, NH), 4.70 (dd, 1H), 4.51–4.41 (m, 2H), 4.38–4.30 (2×d, 2H), 4.25 (t, 1H), 2.85 (dd, 1H), 2.70 (dd, 1H), 1.41 (s, 9H).

Step 4: Loading of Ketone 1 to Resin A and the Title Compound

A suspension of ketone 1 (4.5 g, 9.22 mmol) and Resin A (8.8 g, 7.13 mmol) in TBF (70 mL) in the presence of AcOH (0.2 mL, 3.4 mmol) was shaken on an orbital shaker at 200 rpm overnight. The suspension was filtered and residual resin was washed sequentially with THF, dichloromethane, ethyl acetate and diethyl ether. Drying under high vacuum afforded Resin B (11.7 g).

To a suspension of Resin B (0.33 g) in DMF (3 mL) was added 2-fluorophenol (73 μL) and Cs$_2$CO$_3$ (268 mg), and the mixture was agitated for 2.5 h. After filtration, the resin was washed thoroughly with DMF/H$_2$O, H$_2$O, DMF, THF and MeOH and dried under vacuum. This resin was then subjected to a solution of 20% piperidine in DMF for 20 minutes and then washed sequentially with DMF, methanol, dichloromethane and methanol and dried under high vacuum. To the resin in DMF was added Fmoc-Valine-OH (0.22 g) and HATU (0.25 g) and DIEA (0.12 mL) and the mixture was mixed for 2 hours at room temperature and filtered. The resin was washed with DMF and then treated with a solution of 20% (v) piperidine in DMF and washed again with DMF, methanol, dichloromethane and methanol and dried under vacuum. The resultant resin was suspended in DMF again, and to the suspension was added acid 15 (0.16 g), HATU (0.25 g) and DIEA (0.12 mL) the suspension was agitated for 2 hours and filtered, and washed sequentially with DMF, methanol, dichloromethane, ethyl acetate and ether. A solution consisting of TFA and water (9:1, v/v) was then added and the mixture rotated for 1 hour and filtered. The filtrate was collected and residual resin washed with dichloromethane and acetonitrile. The filtrate and washing solutions were combined, concentrated in vacuo and triturated with ether to afford the title compound as a white solid (136 mg). MS for the title compound (−APCI): m/z 569.5 (M−1)$^−$.

Examples 3, 7–15, 32–68 can either be prepared similarly or according to the solution phase protocol described for Example 5.

EXAMPLE 5

(3S)-3-{[(2S)-2-({[2-Methoxy-5-(3-methyl-1,2,4-oxadiazol-5-yl)-phenyl]acetyl}amino}-3-methylbutanoyl]amino}-5-(1-naphthoyloxy)-4-oxopentanoic Acid

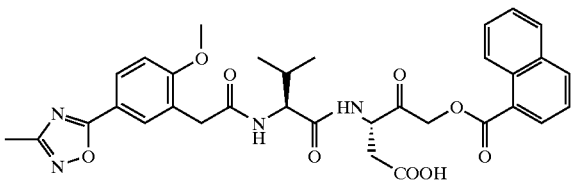

Method 1: Solid Phase Synthesis.
  Step 1: Preparation of Compound 16

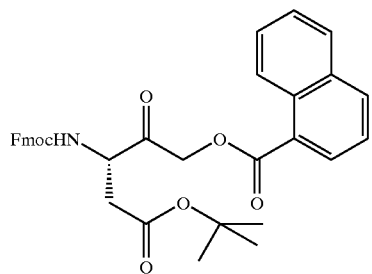

16

A mixture of bromide 1 (470 mg), 2-naphthoic acid (200 mg) and potassium fluoride (116 mg) in DMF (5 mL) was stirred at room temperature for 2 hours and diluted with ether and water. The organic layer was separated, washed with water, aqueous sodium bicarbonate and brine, dried over MgSO$_4$ and filtered. Evaporation of solvents afforded compound 16 as a white powder (540 mg). $^1$H NMR (400 MHz, acetone-d$_6$): δ 8.89 (d, 1H), 8.38 (d, 1H), 8.20 (d, 1H), 8.01 (d, 1H), 7.85 (d, 2H), 7.71 (d, 1H), 7.65–7.55 (m, 3H), 7.40–7.30 (m, 4H), 7.10 (br d, 1H), 5.22 (AB dd, 2H), 4.73 (dd, 1H), 4.53 (dd, 1H), 4.43 (dd, 1H), 4.26 (dd, 1H), 2.89 (dd, 1H), 2.72 (dd, 1H), 1.40 (s, 9H).

Step 2: Loading of 16 to Resin A and the Title Compound

To a suspension of Resin A (0,5 g, 0.6 mmol/g) in THF (5 mL) in a fritted reservoir was added compound 16 (260 mg) and acetic acid (9 µL) and the suspension was rotated overnight. The mixture was filtered and the residual resin washed with THF, ethyl acetate, dichloromethane and ether. This resin was then treated with a solution of 20% (v) piperidine in DMF (5 mL) for 10 min and filtered. This resin was then processed to the title compound as described in Example 4. $^1$H NMR (400 MHz, DMSO-d$_6$): δ 8.70 (d, 1H), 8.20 (d, 1H), 8.15 (d, 1H), 8.05 (d, 1H), 8.00–7.95 (m, 2H), 7.65–7.60 (3H), 7.15 (d, 1H), 5.23–5.12 (AB dd, 2H), 4.68 (dd, 1H), 4.21 (dd, 1H), 3.81 (s, 3H), 3.67–3.52 (AB dd, 2H), 2.82 (dd, 1H), 2.63 (dd, 1H), 2.32 (s, 3H), 2.02 (m, 1H), 0.89 (d, 6H). MS (+EI): 631.0 (M+1)$^+$.

Method 2. Solution Phase Synthesis

The solution phase synthesis of this compound is illustrated in the scheme below.

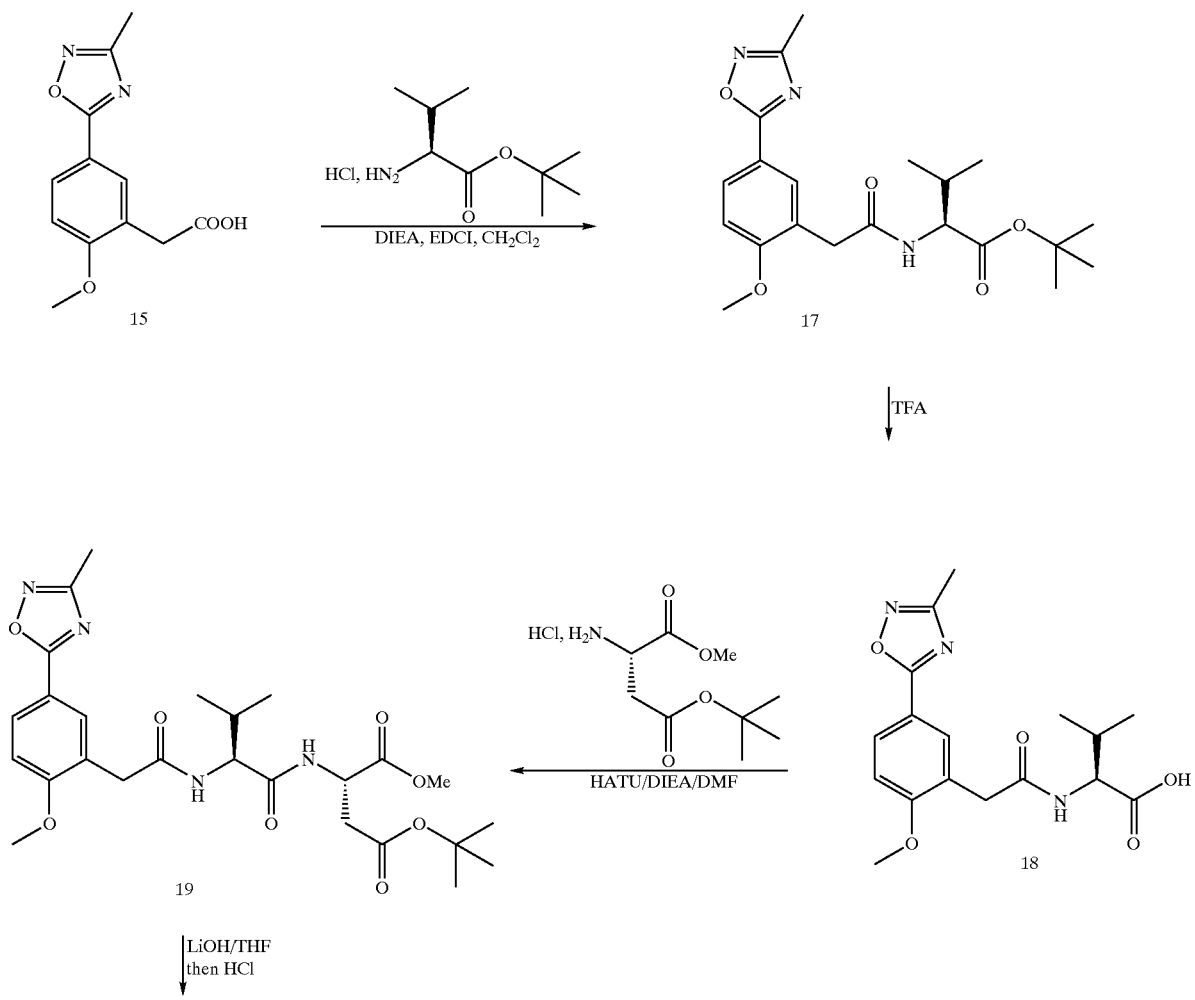

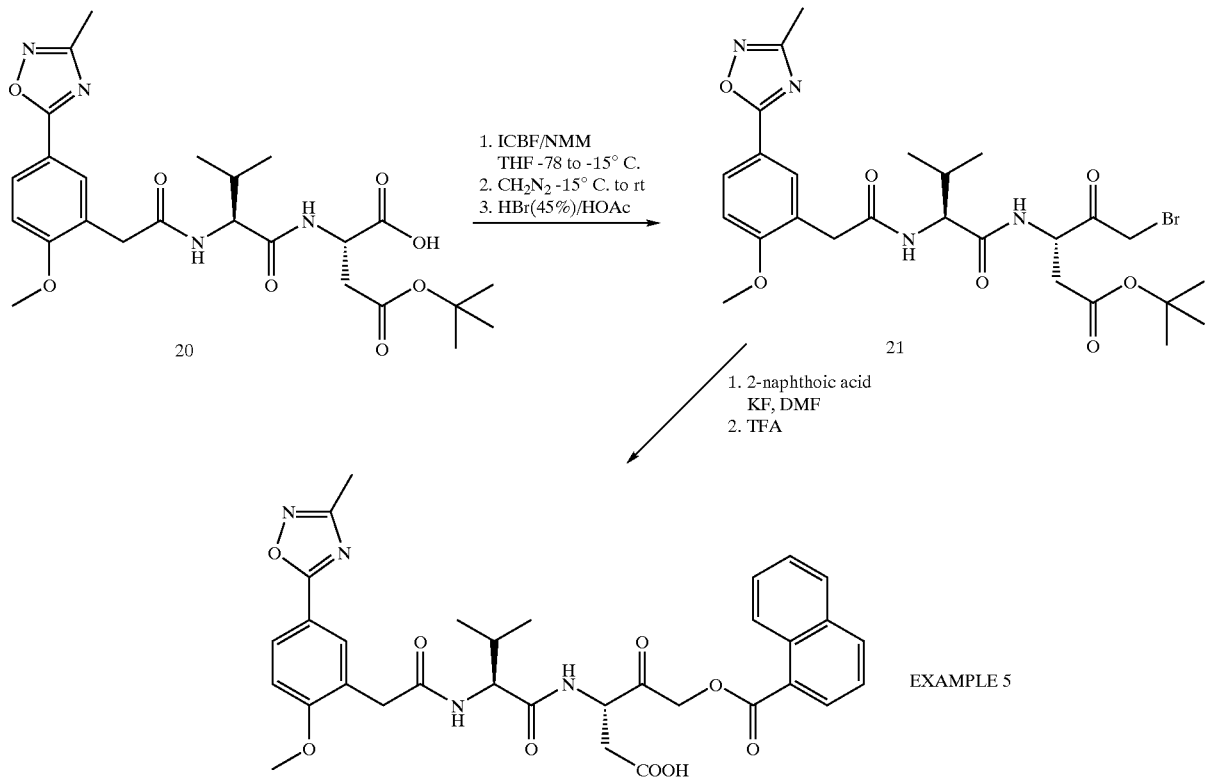

EXAMPLE 5

A mixture of acid 15 (2.48 g, 10 mmol), (S)-valine t-butyl ester hydrochloride (2.3 g), EDCI (2.3 g) and diisopropylethylamine (5.3 mL) in dichloromethane (100 mL) was stirred at room temperature for 2 hours. Most of solvents were removed in vacuo and the residue was diluted with 1 N HCl and ether. The layers were separated and the aqueous layer was extracted twice with ether. The organic layers were combined, washed with 1 N HCl, water and aqueous sodium bicarbonate. After drying over $MgSO_4$ and vacuum filtration, the solution was concentrated in vacuo to afford the desired product 17 as a white powder (3.7 g). $^1$H NMR (300 MHz, acetone-$d_6$): δ 8.01 (m, 2H), 7.20 (d, 1H), 7.10 (br d, 1H), 4.30 (dd, 1H), 3.96 (s, 3H), 3.65 (AB dd, 2H), 2.36 (s, 3H), 2.12 (m, 1H), 1.41 (s, 9H) and 0.90 (2×d, 6H).

Product 17 from above was treated with a solution of 20% TFA (v) in dichloromethane for 1 hour at room temperature. Concentration in vacuo yielded the desired acid 18 as a white powder. $^1$H NMR (400 MHz, acetone-$d_6$): δ 8.00 (m, 2H), 7.22 (br d, 1H), 7.19 (d, 1H), 4.44 (dd, 1H), 3.94 (s, 3H), 3.70 (AB dd, 2H), 2.37 (s, 3H), 2.15 (m, 1H), 0.92 (2×d, 6H).

To a solution of Acid 18 (2.1 g, 6.05 mmol) in DMF (30 mL) was added (S)-β-t-butyl aspartic acid methyl ester hydrochloride (1.6 g, 6.66 mmol), HATU (2.53 g, 6.66 mmol) and diisopropylethylamine (2.41 mL) and the solution was stirred at room temperature for 2 hours and diluted with water and ether. The layers were separated and aqueous layer extracted twice with ether. The organic layers were combined, washed with 1 N HCl, water and brine and dried over $Na_2SO_4$. Evaporation of solvents in vacuo gave a white solid which was recrystallized from ethyl acetate and hexanes. The product 19 (3 g) thus obtained was a white powdery solid. $^1$H NMR (400 MHz, acetone-$d_6$): δ 8.02–7.98 (m, 2H), 7.61 (br d, 1H), 7.20 (d, 1H), 7.12 (br d, 1H), 4.74 (m, 1H), 4.33 (dd, 1H), 3.96 (s, 3H), 3.73–3.60 (m, 5H), 2.80–2.68 (m, 2H), 2.36 (s, 3H), 2.10 (m, 1H), 1.38 (s, 9H) and 0.91–0.87 (m, 6H).

The methyl ester in 19 was hydrolyzed as follow: To a solution of 19 (2.7 g) in THF (56 mL) was added LiOH (5.6 mL, 1 M) at room temperature and the mixture was stirred for 1 hour and acidified with 1 N HCl. The mixture was then extracted with ethyl acetate (3×) and the extracts washed with water and brine, dried over $Na_2SO_4$ and concentrated to give acid 20 as a white powder (2.5 g). $^1$H NMR (500 MHz, acetone-$d_6$): δ 8.03–7.99 (m, 2H) 7.95 (br d, 1H), 7.50 (br d, 1H), 7.20 (d, 1H), 4.69 (dd, 1H), 4.34 (dd, 1H), 3.95 (s, 3H), 3.70 (d, 1H), 3.61 (d, 1H), 2.76 (dd, 1H), 2.67 (dd, 1H), 2.38 (s, 3H), 2.10 (m, 1H), 1.40 (s, 9H), 0.90 (m, 6H).

To a solution of acid 20 (2.5 g, 4.83 mmol) in THF (250 mL) at −78° C. under a nitrogen atmosphere was added N-methylmorpholine (0.69 mL) and iso-butyl chloroformate (0.75 mL). The mixture was stirred at the temperature for 30 min and allowed to warm to −15° C. for 30 min. Excess amounts of diazomethane in ether was added (until the solution remained yellow at room temperature) and the resultant mixture was stirred at room temperature for 30 min and cooled to 0° C. To it was added a solution of 1:1 (v/v) 45% HBr and glacial acetic acid (40 mL) and the mixture was diluted with water and extracted with ethyl acetate (3×). The extracts were combined, washed with water and brine, dried over $MgSO_4$ and filtered. The filtrate was concentrated in vacuo and co-evaporated with toluene (2×) to give a white solid. The solid was recrystallized from ethyl acetate and hexanes to give bromomethyl ketone 21 as a white solid (2.8 g from two crops). $^1$H NMR (500 MHz, acetone-$d_6$): δ 8.03–7.97 (m, 3H), 7.28 (br d, 1H), 7.20 (d, 1H), 4.80 (dd, 1H), 4.40 (d, 1H), 4.28–4.12 (m, 2H), 3.96 (s, 3H), 3.72–3.62 (dd, 2H), 2.87 (dd, 1H), 2.70 (dd, 1H), 2.37 (s, 3H), 2.13 (m, 1H), 1.40 (s, 9H), 0.92 (m, 6H).

The title compound: To a solution of bromomethyl ketone 21 (1.05 g) in DMF (30 mL) was added 2-naphthoic acid (0.334 g) and potassium fluoride (0.205 g). The resulting mixture was stirred at room temperature for 3 hours and diluted with water and aqueous sodium bicarbonate. The mixture was then extracted with ethyl acetate (3×) and the extracts washed with NaHCO$_3$ (aq), water and brine. After drying over MgSO$_4$, the solution was filtered and the filtrate was concentrated in vacuo to furnish the desired product as a white solid (1.05 g). $^1$H NMR (500 MHz, acetone-$d_6$): δ 8.87 (d, 1H), 8.26 (d, 1H), 8.20 (d, 1H), 8.05–7.95 (m, 4H), 7.67–7.57 (m, 3H), 7.30 (br d, 1H), 7.18 (d, 1H), 5.30–5.27 (AB dd, 2H), 4.87 (dd, 1H), 4.33 (dd, 1H), 3.96 (s, 3H), 3.70 (AB dd, 2H), 2.90 (dd, 1H), 2.75 (dd, 1H), 2.32 (s, 3H), 2.17 (m, 1H), 1.41 (s, 9H) and 0.98 (m, 6H). This compound was then treated with TFA (5 mL) in dichloromethane (20 mL) at room temperature for 1 hour and then concentrated to give the title compound as a white solid.

Examples 6, 17–24, 26–30 were prepared accordingly.

EXAMPLE 7

(3S)-5-[(2,2-Dimethyl-2,3-dihydrobenzo[b]furan-5-yl)oxy-]3-{[(2S)-2-({2-methoxy-5-(3-methyl-1,2,4-oxadiazol-5-yl)-phenyl]acetyl}amino)-3-methylbutanoyl]amino}-4-oxopentanoic Acid

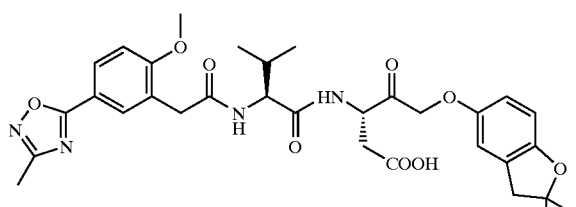

To a suspension of Resin A (0.3 g) in DMF (3 mL) was added 2,3-dihydro-2-dimethyl-7-benzofuranol (223 μL) and Cs$_2$CO$_3$ (244 mg), and the mixture was agitated for 2.5 h. After filtration, the resin was washed thoroughly with DMF/H$_2$O, H$_2$O, DMF, THF and MeOH and dried under vacuum. This resin was then processed to the title compound as described in Example 4 (e.g., a) 20% piperidine/DMF; b) Fmoc-valine-OH/HATU/DIEA/DMF; c) 20% piperidine/DMF; d) acid 15/HATU/DEA/DMF; e) TFA/H$_2$O). MS for the title compound (−APCI): m/z 621.9 (M−1)$^-$.

EXAMPLE 16

(3S)-3-{[(2S)-2-({[2-{[5-({5-[(3aS,4S,6aR)-2-Oxohexahydro-1-thieno[3,4-d]imidazol-4-yl]pentanoyl}amino)pentyl]amino}-2-oxoetyoxy)-5-(3-methyl-1,2,4-oxadiazol-5-yl)-phenyl]acetyl}amino}-3-methylbutanoyl]amino}-5-(1-naphthoyloxy)-4-oxopentanoic Acid

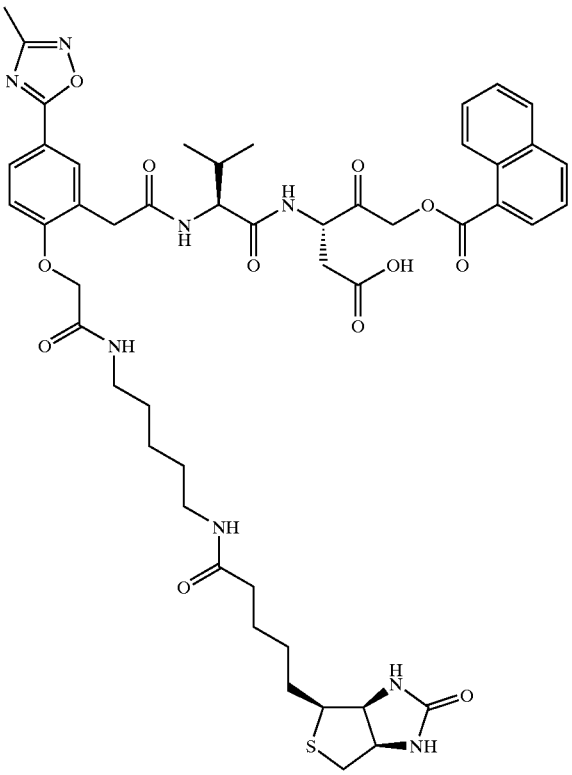

Step 1: Preparation of Compound 22

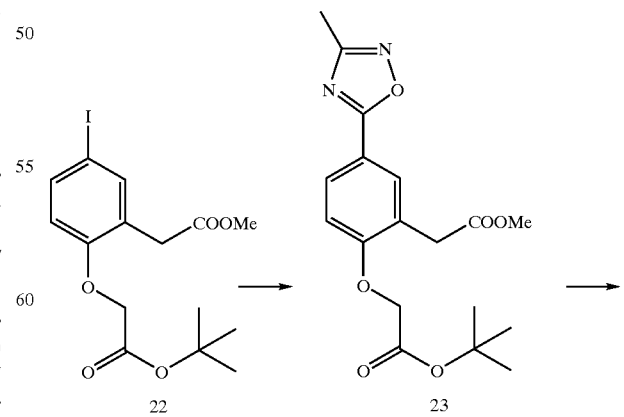

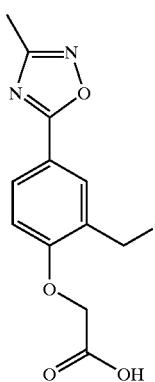

24

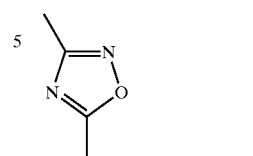

25

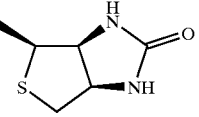

26

Step 3: Preparation of Compound 25 and 26 and the Title Compound

To a solution of methyl 2-hydroxy-5-iodophenylacetate (590 mg) in THF was added NaH (89 mg, 60% oil dispersion) at 0° C. and the mixture was stirred at the temperature for 1 hour. To the mixture was added t-butyl bromoacetate (0.33 mL) in one portion and the mixture was allowed to warm to room temperature and stirred for 5 hours. After quenching with NH$_4$Cl (aq), the mixture was extracted with ethyl acetate. The extract was washed with brine, dried, filtered and concentrated. The residue was purified by flash chromatography. Eluting with 15–30% ethyl acetate in hexanes afforded compound 22 (550 mg). $^1$H NMR (500 MHz, acetone-d$_6$): δ 7.59–7.55 (m, 2H), 6.75 (d, 1H), 4.61 (s, 2H), 3.67 (s, 2H), 3.63 (s, 3H), 1.44 (s, 9H).

Step 2: Preparation of Compound 23 and 24

A mixture of iodide 22 (550 mg), Pd(PPh$_3$)$_2$Cl$_2$ (47 mg) and methylamidoxime (304 mg) in toluene (6 mL) was purged with CO three times and then heated to 90–95° C. under a CO atmosphere for 6.5 hours. The mixture was cooled to room temperature and diluted with water and ethyl acetate. The organic layer was separated and the aqueous layer was extracted twice with ethyl acetate. The organic layers were combined, washed with water and brine, dried over MgSO$_4$ and filtered. The solution was concentrated and the residue purified by column chromatography. Eluting with 25–40% ethyl acetate in hexanes furnished compound 23 (214 mg). $^1$H NMR (400 MHz, acetone-d$_6$): δ 8.02–7.99 (m, 2H), 7.10 (d, 1H), 4.76 (s, 2H), 3.80 (s, 2H), 3.65 (s, 3H), 2.36 (s, 3H), 1.45 (s, 9H). The t-butyl ester in 23 was deprotected using 20% TFA in dichloromethane to afford the corresponding acid 24 as a white solid. $^1$H NMR (400 MHz, acetone-d$_6$): δ 7.99–7.95 (m, 2H), 7.11 (d, 1H), 4.81 (s, 2H), 3.80 (s, 2H), 3.59 (s, 3H), 2.37 (s, 3H).

A solution of acid 24 (57 mg), 5-(biotinamido) pentylamine (Pierce, 61 mg), EDCI (43 mg), DMAP (1 crystal) and DIEA (65 mL) in DMF (5 mL) was stirred at room temperature for 3 hours. The mixture was co-evaporated with toluene until most of the DMF was removed and then diluted with water to give a white solid. The solid was washed with water (2×), ether (2×) and ethyl acetate (2×) and dried under high vacuum to yield compound 25 (63 mg) as a white solid. MS (+APCI): m/z 617.4 (M+1)$^+$. The methyl ester in 25 was hydrolyzed with LiOH in methanol. Thus, a mixture of compound 25 (61 mg) and LiOH (0.5 mL, 1 N) in methanol (5 mL) and water (1 mL) was stirred at room temperature with occasional heating for 4 hours. The volatiles were evaporated, and the residue was washed with water and dried under high vacuum to give acid 26 (33 mg) as a white solid. MS (-ESI): m/z 601.3 (M-1)$^-$.

Acid 26 was processed to the title compound as described in Example 5. MS (-APCI): m/z 983.7 (M-1)$^-$.

Assays for Determining Biological Activity (a) Measurement of Caspase Activity by Cleavage of a Fluorogenic Substrate A fluorogenic derivative of the tetrapeptide recognized by caspase-3 and corresponding to the P1 to P4 amino acids of the PARP cleavage site, Ac-DEVD-AMC (AMC, amino-4-methylcoumarin) was prepared as follows: i) synthesis of N-Ac-Asp(OBn)-Glu(OBn)-Val-CO2H, ii) coupling with Asp(OBn)-7-amino-4-methylcoumarin, iii) removal of benzyl groups.

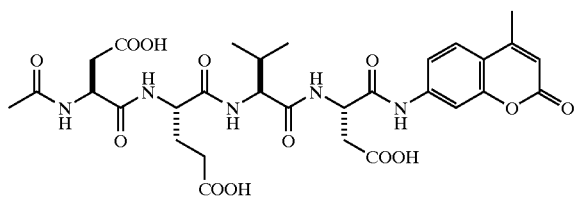

Standard reaction mixtures (300 μL final volume), contained Ac-DEVD-AMC and purified or crude caspase-3 enzyme in 50 mM Hepes/KOH (pH 7.0), 10% (v/v) glycerol, 0.1% (w/v) CHAPS, 2 mM EDTA, 5 mM dithiothreitol, and were incubated at 25° C. Reactions were monitored continuously in a spectrofluorometer at an excitation wavelength of 380 nm and an emission wavelength of 460 nm.

(b) Cell Death Detection ELISA (Whole Cell Assay)

Photometric immunoassay for the qualitative and quantitative in vitro determination of cytoplasmic histone-associated-DNA-fragments (mono- and oligonucleosomes) after induced cell death. This assay was performed using the commercially available kit from Boehringer Mannheim, cat. No. 1 920 685.

(c) In Vivo Myocardial Ischemia and Reperfusion Injury in Rats

Male Sprague-Dawley rats (300–400g) were fasted overnight, and then anesthetized with intraperitoneal administration of sodium pentobarbital (65 mg/kg). To monitor heart rate and aortic pressure the left carotid artery was isolated and a cannula placed in the vessel. The aortic cannula was interfaced with a pressure transducer which was connected to a physiologic recorder. The left jugular vein was isolated and cannulated for administration of a caspase inhibitor compound or vehicle (2% dimethylsulfoxide in 0.9% NaCl). A left thoracotomy was performed in the region overlying the heart and the pericardium opened, exposing the heart. The origin of the left coronary artery was visualized and a 4.0 suture passed under the artery approximately 2–3 mm from its origin. The ends of the suture were passed through a short length of 2 mm id tubing and coronary artery occlusion effected by placing tension on the suture such that the tube compressed the artery. After initial placement of the suture/occluder, the thoracotomy was closed with a small clamp and opened only to effect occlusion and reperfusion of the artery. A Lead II electrocardiograph (ECG) signal was obtained by placing subdermal platinum leads and continuously monitored. After a baseline period of 20–30 minutes the left coronary artery was occluded for 45 minutes. The period of reperfusion was 3 hours. The caspase inhibitor or vehicle was administered as a first bolus 5 minutes before the onset of ischemia and a second bolus was administered again at the onset of reperfusion. Additionally, an infusion was initiated immediately after the first bolus dose. Control animals received the vehicle alone in equal volumes to the caspase inhibitor treated animals. At the end of reperfusion the animals were euthanized and infarct size determined using a dual staining technique (1.5% w/v triphenyltetrazolium chloride to demarcate infarct tissue and 0.25% w/v Evan's blue to demarcate the area at risk of infarct. The heart was subsequently cut transversely into 4 slices of equal thickness, and infarct size and area at risk quantified using planimetry.

Using the above procedure, it is demonstrated that administration of a caspase inhibitor reduces infarct size in the rat subjected to 45 minutes of regional ischemia and 3 hours of reperfusion.

(d) In Vivo Rat Middle Cerebral Artery Occlusion (MCAO)

Male Wistar rats are anesthetized with isoflurane (1.5%–3%) using a face mask for surgical isolation of the right middle cerebral artery (MCA) and the right and left common carotid artery. Anesthetized animals are then placed on a water jacketed heating pad to maintain normal body temperature. To ensure adequate hydration throughout the experiment, rats are administered 10–15 ml/kg of sterile 0.9% NaCl subcutaneously after anesthesia. The rats are then placed on its right side and the heads immobilized. An incision is made directly in front of the ear, extending down from the base of the ear approximately 1.5 cm. The skin is held back and the salivary gland dissected from surrounding tissues. The gland is pulled forward and down away from surgical field. The temporalis muscle is dissected and retracted. Fascia overlying the skull is removed, leaving a clean section of the skull. The bone of the skull is "thinned" with surgical drill (2mm burr) and remaining skull dissected away from the dura with forceps. The dura is removed, revealing the MCA. The right MCA is occluded using a 1 mm microclip. The right common carotid artery is permanently occluded using a suture. The left common carotid artery is occluded for a period of time equal to the MCA. Rats are awake within 10 minutes after the end of anesthesia. Analgesis is provided to the rats with oxymorphone (0.01 ml/100 g body weight), once or twice according to veterinary advice.

After surgical isolation of the MCA, the MCA is occluded for a period of 30–120 minutes. The left common carotid artery is occluded for the same period of time as the MCA. In these experiments, compounds are administered by different route (icv, iv or ip), as a bolus and/or continuous infusion, before or after the occlusion. Both the MCA and the left common carotid artery are then reperfused. Animals are then administered prophylactic analgesia, and returned to individual cages. At the end of reperfusion, the animals are euthanized and the brains are cut into 2 mm slices and stained with 1.5% w/v triphenyltetrazolium chloride. The infarct size in the brain is determined using a commercially available imaging system.

Using the above procedure, it is demonstrated that administration of a caspase-3 inhibitor reduces infarct size in the cortex regions of the rat brains when the animals are subjected to a 30 to 90 minutes ischemia and 24 hours of reperfusion.

What is claimed is:

1. A compound represented by Formula I:

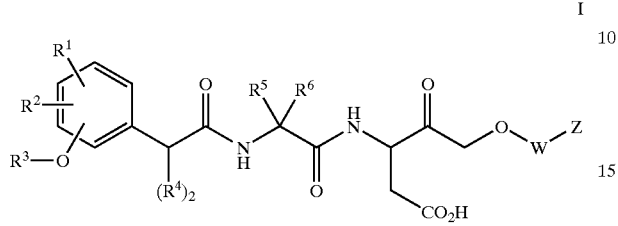

or a pharmaceutically acceptable salt, ester or hydrate thereof, wherein:

W is a bond, —$CH_2$—, —C(O)— or —C(O)$CH_2$—;

Z is selected from the group consisting of:
(1) H,
(2) $C_{1-11}$alkyl,
(3) $C_{3-11}$cycloalkyl or a benzofused analog thereof,
(4) phenyl or naphthyl, and
(5) $HET^1$, wherein $HET^1$ represents a 5- to 10-membered mono- or bicyclic, aromatic or non-aromatic ring, or a benzofused analog thereof, containing 1–3 heteroatoms selected from O, S and N, groups (2), (3) and (5) above are optionally substituted with 1–2 oxo groups, groups (2)–(5) above are further optionally substituted with 1–3 substituents independently selected from the group consisting of:
(a) halo
(b) nitro,
(c) hydroxy,
(d) $C_{1-4}$alkyl,
(e) $C_{1-4}$alkoxy,
(f) $C_{1-4}$alkylthio,
(g) $C_{3-6}$cycloalkyl,
(h) phenyl or naphthyl,
(i) phenoxy,
(j) benzyl,
(k) benzyloxy, and
(l) a 5 or 6-membered aromatic or non-aromatic ring containing from 1–3 heteroatoms selected from O, S and N, groups (d)–(g) above are optionally substituted with oxo and 1–3 substituents independently selected from halo and $C_{1-4}$alkoxy, groups (h)–(l) above are optionally substituted with 1–3 substituents independently selected from halo and $C_{1-4}$alkyl, and group (4) is further optionally substituted up to its maximum with halo groups;

$R^1$ and $R^2$ are independently selected from the group consisting of:
(1) H,
(2) halo,
(3) hydroxy,
(4) nitro,
(5) cyano,
(6) $C_{1-10}$alkyl, $C_{3-10}$cycloalkyl, $C_{1-10}$alkoxy, —S(O)$_{0-2}$$C_{1-10}$alkyl or —NH$C_{1-10}$alkyl, each optionally substituted with 1–2 oxo or carboxy groups and further optionally substituted with 1–3 substituents independently selected from the group consisting of:
(a) halo,
(b) hydroxy
(c) cyano,
(d) $C_{1-4}$alkoxy,
(e) —$NHR^7$, wherein $R^7$ is H or $C_{1-5}$alkyl, said $C_{1-5}$alkyl optionally substituted with —$NHR^8$, wherein $R^8$ is $C_{1-5}$alkyl optionally substituted with a oxo and further optionally substituted with a 5- to 10-membered mono- or bicyclic, aromatic or non-aromatic ring, or a benzofused analog thereof, containing 1–3 heteroatoms selected from O, S and N, and optionally substituted with oxo,
(f) —S(O)$_{0-2}$$C_{1-4}$alkyl, and
(g) $HET^2$, wherein $HET^2$ represents a 5- to 7-membered aromatic or non-aromatic ring containing 1–4 heteroatoms selected from O, S and $NR^7$, wherein $R^7$ is H or $C_{1-5}$alkyl, said $HET^2$ being optionally substituted with oxo and further optionally substituted with 1–2 substituents independently selected from halo and $C_{1-4}$alkyl, said $C_{1-4}$alkyl being optionally substituted with 1–3 halo groups,
(7) phenoxy or —S(O)$_{0-2}$phenyl,
(8) benzyloxy or —S(O)$_{0-2}$benzyl,
(9) benzoyl,
(10) phenyl or naphthyl,
(11) —O-$HET^2$ or —S-$HET^2$, said $HET^2$ being optionally substituted with oxo and further optionally substituted as defined below, and
(12) $HET^3$, wherein $HET^3$ is a 5- or 6-membered aromatic or non-aromatic ring, or a benzofused analog thereof, containing from 1 to 4 heteroatoms selected from O, S and N, said $HET^3$ being optionally substituted with oxo and further optionally substituted as defined below, groups (7)–(12) above are each optionally substituted with 1–2 substituents independently selected from the group consisting of: halo, cyano, $C_{1-4}$alkyl and $C_{1-4}$alkoxy, said $C_{1-4}$alkyl and $C_{1-4}$alkoxy being optionally substituted with 1–3 halo groups;

or $R^1$ and $R^2$ may be taken in combination and represent a fused ring as shown below:

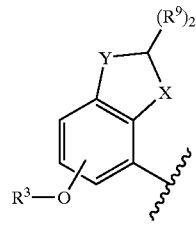

wherein Y and X are independently selected from the group consisting of —C($R^{10}$)$_2$—, —C($R^{10}$)$_2$C($R^{10}$)$_2$—, —$NR^{11}$—, —O— and —S—, $R^3$ is as defined below, each $R^9$ is independently selected from H and $C_{1-4}$alkyl, each $R^{10}$ is independently selected from H and $C_{1-4}$alkyl, and $R^{11}$ is H or $C_{1-4}$alkyl, or one $R^9$ may be joined with either one $R^{10}$ or $R^{11}$ on an adjacent atom to form a double bond;

$R^3$ is $C_{1-10}$alkyl, optionally substituted with 1–2 oxo or carboxy groups and further optionally substituted with 1–3 substituents independently selected from the group consisting of:

(a) halo,
(b) hydroxy
(c) cyano,
(d) $C_{1-4}$alkoxy,
(e) —NHR$^7$, wherein R$^7$ is H or $C_{1-5}$alkyl, said $C_{1-5}$alkyl optionally substituted with —NHR$^8$, wherein R$^8$ is $C_{1-5}$alkyl optionally substituted with oxo and further optionally substituted with a 5- to 10-membered mono- or bicyclic, aromatic or non-aromatic ring, or a benzofused analog thereof, containing 1–3 heteroatoms selected from O, S and N, and optionally substituted with oxo,
(f) —S(O)$_{0-2}$C$_{1-4}$alkyl, and
(g) HET$^2$, wherein HET$^2$ represents a 5- to 7-membered aromatic or non-aromatic ring containing 1–4 heteroatoms selected from O, S and NR$^7$, wherein R$^7$ is H or $C_{1-5}$alkyl, said HET$^2$ being optionally substituted with oxo and further optionally substituted with 1–2 substituents independently selected from halo or $C_{1-4}$alkyl, said $C_{1-4}$alkyl being optionally substituted with 1–3 halo groups, each R$^4$ is independently selected from the group consisting of: H, halo, hydroxy, $C_{1-6}$alkyl and $C_{1-4}$alkoxy, said $C_{1-6}$alkyl and $C_{1-4}$alkoxy being optionally substituted with oxo and further optionally substituted with 1–3 halo groups; and R$^5$ is selected from the group consisting of: H, phenyl, naphthyl, $C_{1-6}$alkyl optionally substituted with OR$^{12}$ and 1–3 halo groups, and $C_{5-7}$cycloalkyl optionally containing one heteroatom selected from O, S and NR$^{13}$, wherein R$^{12}$ is selected from the group consisting of: H, $C_{1-5}$alkyl optionally substituted with 1–3 halo groups, and benzyl optionally substituted with 1–3 substituents independently selected from halo, $C_{1-4}$alkyl and $C_{1-4}$alkoxy, and R$^{13}$ is H or $C_{1-4}$alkyl optionally substituted with 1–3 halo groups; and R$^6$ represents H;

or in the alternative, R$^5$ and R$^6$ are taken in combination and represent a ring of 4–7 members, said ring optionally containing one heteroatom selected from O, S and NR$^{13}$.

2. A compound according to claim 1 wherein R$^1$ is selected from the group consisting of:
(1) halo,
(2) hydroxy,
(3) nitro,
(4) cyano,
(5) $C_{1-10}$alkyl, $C_{3-10}$cycloalkyl, $C_{1-10}$alkoxy, —S(O)$_{0-2}$C$_{1-10}$alkyl or —NHC$_{1-10}$alkyl, each optionally substituted with 1–2 oxo or carboxy groups and further optionally substituted with 1–3 substituents independently selected from the group consisting of:
(a) halo,
(b) hydroxy
(c) cyano,
(d) $C_{1-4}$alkoxy,
(e) —NHR$^7$, wherein R$^7$ is H or $C_{1-5}$alkyl, said $C_{1-5}$alkyl optionally substituted with —NHR$^8$, wherein R$^8$ is $C_{1-5}$alkyl optionally substituted with oxo and further optionally substituted with a 5- to 10-membered mono- or bicyclic, aromatic or non-aromatic ring, or a benzofused analog thereof, containing 1–3 heteroatoms selected from O, S and N, and optionally substituted with oxo,
(f) —S(O)$_{0-2}$C$_{1-4}$alkyl, and
(g) HET$^2$, wherein HET$^2$ represents a 5- to 7-membered aromatic or non-aromatic ring containing 1–4 heteroatoms selected from O, S and NR$^7$, wherein R$^7$ is H or $C_{1-5}$alkyl, said HET$^2$ being optionally substituted with oxo and further optionally substituted with 1–2 substituents independently selected from halo and $C_{1-4}$alkyl, said $C_{1-4}$alkyl being optionally substituted with 1–3 halo groups,
(6) phenoxy or —S(O)$_{0-2}$phenyl,
(7) benzyloxy or —S(O)$_{0-2}$benzyl,
(8) benzoyl,
(9) phenyl or naphthyl,
(10) —O-HET$^2$ or —S-HET$^2$, said HET$^2$ being optionally substituted with oxo and further optionally substituted as defined below, and
(11) HET$^3$, wherein HET$^3$ is a 5- or 6-membered aromatic or non-aromatic ring, or a benzofused analog thereof, containing from 1 to 4 heteroatoms selected from O, S and N, said HET$^3$ being optionally substituted with oxo and further optionally substituted as defined below, and groups (6)–(11) above are each optionally substituted with 1–2 substituents independently selected from the group consisting of: halo, cyano, $C_{1-4}$alkyl and $C_{1-4}$alkoxy, said $C_{1-4}$alkyl and $C_{1-4}$alkoxy being optionally substituted with 1–3 halo groups.

3. A compound according to claim 1 wherein R$^3$ is methyl, optionally substituted with 1–3 halo groups.

4. A compound according to claim 1 wherein one R$^4$ is hydroxy and the other R$^4$ is H.

5. A compound according to claim 1 wherein R$^5$ is isopropyl and R$^6$ is H.

6. A compound according to claim 1 wherein W is a bond.

7. A compound according to claim 1 wherein W is —CH$_2$—.

8. A compound according to claim 1 wherein W is —C(O)—.

9. A compound according to claim 1 wherein W is —C(O)CH$_2$—.

10. A compound according to claim 1 wherein Z is phenyl or naphthyl, wherein:

said phenyl or naphthyl is optionally substituted with 1–3 substituents independently selected from the group consisting of:
(a) nitro,
(b) hydroxy,
(c) $C_{1-4}$alkyl,
(d) $C_{1-4}$alkoxy,
(e) $C_{1-4}$alkylthio,
(f) $C_{3-6}$cycloalkyl,
(g) phenyl or naphthyl,
(h) phenoxy,
(i) benzyl,
(j) benzyloxy, and
(k) a 5 or 6-membered aromatic or non-aromatic ring containing from 1–3 heteroatoms selected from O, S and N, groups (c)–(f) above are optionally substituted with oxo and 1–3 substituents independently selected from halo and $C_{1-4}$alkoxy, groups (g)–(k) above are optionally substituted with 1–3 substituents independently selected from halo and $C_{1-4}$alkyl, and said phenyl or naphthyl is further optionally substituted up to its maximum with halo groups.

11. A compound according to claim 1 wherein Z is $C_{1-11}$alkyl, optionally substituted with 1–2 oxo groups and further optionally substituted with 1–3 substituents independently selected from the group consisting of:
  (a) halo
  (b) nitro,
  (c) hydroxy,
  (d) $C_{1-4}$alkyl,
  (e) $C_{1-4}$alkoxy,
  (f) $C_{1-4}$alkylthio,
  (g) $C_{3-6}$cycloalkyl,
  (h) phenyl or naphthyl,
  (i) phenoxy,
  (j) benzyl,
  (k) benzyloxy, and
  (l) a 5 or 6-membered aromatic or non-aromatic ring containing from 1–3 heteroatoms selected from O, S and N,
  groups (d)–(g) above are optionally substituted with oxo and 1–3 substituents independently selected from halo and $C_{1-4}$alkoxy, and
  groups (h)–(l) above are optionally substituted with 1–3 substituents independently selected from halo and $C_{1-4}$alkyl.

12. A compound according to claim 1 wherein Z is $C_{3-11}$cycloalkyl or a benzofused analog thereof, optionally substituted with 1–2 oxo groups and further optionally substituted with 1–3 substituents independently selected from the group consisting of:
  (a) halo
  (b) nitro,
  (c) hydroxy,
  (d) $C_{1-4}$alkyl,
  (e) $C_{1-4}$alkoxy,
  (f) $C_{1-4}$alkylthio,
  (g) $C_{3-6}$cycloalkyl,
  (h) phenyl or naphthyl,
  (i) phenoxy,
  (j) benzyl,
  (k) benzyloxy, and
  (l) a 5 or 6-membered aromatic or non-aromatic ring containing from 1–3 heteroatoms selected from O, S and N,
  groups (d)–(g) above are optionally substituted with oxo and 1–3 substituents independently selected from halo and $C_{1-4}$alkoxy, and
  groups (h)–(l) above are optionally substituted with 1–3 substituents independently selected from halo and $C_{1-4}$alkyl.

13. A compound according to claim 1 wherein Z is $HET^1$, optionally substituted with 1–2 oxo groups and further optionally substituted with 1–3 substituents independently selected from the group consisting of:
  (a) halo
  (b) nitro,
  (c) hydroxy,
  (d) $C_{1-4}$alkyl,
  (e) $C_{1-4}$alkoxy,
  (f) $C_{1-4}$alkylthio,
  (g) $C_{3-6}$cycloalkyl,
  (h) phenyl or naphthyl,
  (j) phenoxy,
  (i) benzyl,
  (j) benzyloxy, and
  (k) a 5 or 6-membered aromatic or non-aromatic ring containing from 1–3 heteroatoms selected from O, S and N,
  groups (d)–(g) above are optionally substituted with oxo and 1–3 substituents independently selected from halo and $C_{1-4}$alkoxy, and
  groups (h)–(k) above are optionally substituted with 1–3 substituents independently selected from halo and $C_{1-4}$alkyl.

14. A compound according to claim 13 wherein $HET^1$ represents a member selected from the group consisting of: pyridine, pyrimidine, pyridazine, pyrazine, furan, thiophene, thiazole and oxazole, or a benzofused analog thereof, each optionally substituted with 1–3 substituents independently selected from the group consisting of:
  (a) halo,
  (b) nitro,
  (c) $C_{1-4}$alkyl,
  (d) $C_{1-4}$alkoxy,
  (e) $C_{1-4}$alkylthio,
  (f) $C_{3-6}$cycloalkyl,
  (g) phenoxy,
  (h) benzyl,
  (i) benzyloxy, and
  (j) a 5 or 6-membered aromatic or non-aromatic ring containing from 1–3 heteroatoms selected from O, S and N,
  groups (c)–(f) above are optionally substituted with oxo and 1–3 substituents independently selected from halo and $C_{1-4}$alkoxy, and
  groups (g)–(j) above are optionally substituted with 1–3 substituents independently selected from halo and $C_{1-4}$alkyl.

15. A compound according to claim 1 wherein $HET^2$ is selected from the group consisting of: butyrolactone, tetrahydrofuran, tetrahydropyran, 2-pyrrolidinone, pyridine and pyrimidine, each optionally substituted with 1–2 substituents independently selected from halo or $C_{1-4}$alkyl, said $C_{1-4}$alkyl being optionally substituted with 1–3 halo groups.

16. A compound according to claim 1 wherein $HET^3$ is selected from the group consisting of: 1,2,3-oxadiazole, 1,2,4-oxadiazole, 1,3,4-oxadiazole, 1,2,3-thiadiazole, 1,2,4-thiadiazole, 1,3,4-thiadiazole, thiophene, pyrrole, pyridine, tetrazole, oxazole, thiazole, 1,2,3-triazole, 1,2,4-triazole and 1,3,4-triazole, each optionally substituted with 1–2 substituents independently selected from halo or $C_{1-4}$alkyl, said $C_{1-4}$alkyl being optionally substituted with 1–3 halo groups.

17. A compound according to claim 1 wherein:
  W is a bond, —CH$_2$—, —C(O)— or —C(O)CH$_2$—;
  Z is selected from the group consisting of:
    (1) $C_{5-6}$cycloalkyl or a benzofused analog thereof,
    (2) phenyl or naphthyl, and
    (3) $HET^1$, wherein $HET^1$ represents a 5- to 10-membered mono- or bicyclic, aromatic or non-aromatic ring, or a benzofused analog thereof, containing 1–3 heteroatoms selected from O, S and N, wherein:
      groups (1) and (3) above are optionally substituted with 1–2 oxo groups;

groups (1), (2) and (3) above are further optionally substituted with 1–3 substituents independently selected from the group consisting of:
(a) halo,
(b) nitro,
(c) $C_{1-4}$alkyl,
(d) $C_{1-4}$alkoxy,
(e) $C_{1-4}$alkylthio,
(f) $C_{3-6}$cycloalkyl,
(g) phenoxy,
(h) benzyl,
(i) benzyloxy, and
(j) a 5 or 6-membered aromatic or non-aromatic ring containing from 1–3 heteroatoms selected from O, S and N,
groups (c)–(f) above are optionally substituted with oxo and 1–3 substituents independently selected from halo and $C_{1-4}$alkoxy,
groups (g)–(j) above are optionally substituted with 1–3 substituents independently selected from halo and $C_{1-4}$alkyl, and
group (2) is further optionally substituted up to its maximum with halo groups;

$R^1$ is selected from the group consisting of:
(1) halo,
(2) $C_{1-4}$alkyl or $C_{1-4}$alkoxy, each optionally substituted with oxo and 1–3 halo groups, and
(3) HET$^3$, wherein HET$^3$ is a 5- or 6-membered aromatic or non-aromatic ring, or a benzofused analog thereof, containing from 1 to 4 heteroatoms selected from O, S and N, and optionally substituted with 1–2 substituents independently selected from halo and $C_{1-4}$alkyl, said $C_{1-4}$alkyl being optionally substituted with 1–3 halo groups, $R^2$ is H, $R^3$ is $C_{1-4}$alkyl, optionally substituted with 1–3 halo groups and further optionally substituted with oxo or —NHR$^7$ or both, wherein $R^7$ is H or $C_{1-5}$alkyl, said $C_{1-5}$alkyl optionally substituted with —NHR$^8$, wherein $R^8$ is $C_{1-5}$alkyl optionally substituted with oxo and further optionally substituted with

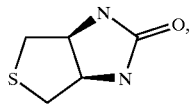

and
each $R^4$ is independently selected from the group consisting of: H and hydroxy.

18. A compound according to claim 17 wherein $R^5$ is isopropyl and $R^6$ is H.

19. A compound according to claim 18 wherein:
HET$^1$ is selected from the group consisting of:
(1) pyridine, pyridazine, pyrimidine or pyrazine, or a benzofused analog thereof, each optionally substituted with 1–3 substituents independently selected from the group consisting of:
(a) halo,
(b) nitro,
(c) $C_{1-4}$alkyl,
(d) $C_{1-4}$alkoxy,
(e) $C_{1-4}$alkylthio,
(f) $C_{3-6}$cycloalkyl,
(g) phenoxy,
(h) benzyl,
(i) benzyloxy, and
(j) a 5 or 6-membered aromatic or non-aromatic ring containing from 1–3 heteroatoms selected from O, S and N, groups (c)–(f) above are optionally substituted with oxo and 1–3 substituents independently selected from halo and $C_{1-4}$alkoxy, groups (g)–(j) above are optionally substituted with 1–3 substituents independently selected from halo and $C_{1-4}$alkyl,

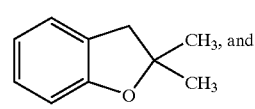

(2)

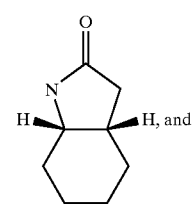

(3)

HET$^3$ is 1,2,4-oxadiazole, optionally substituted with $C_{1-4}$alkyl.

20. A compound selected from the group consisting of:

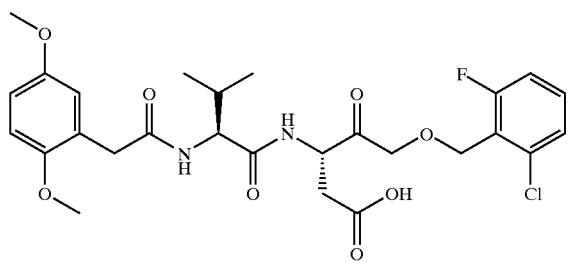

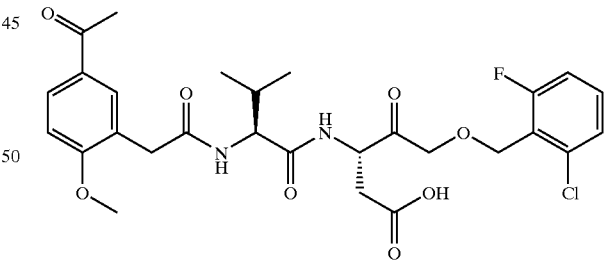

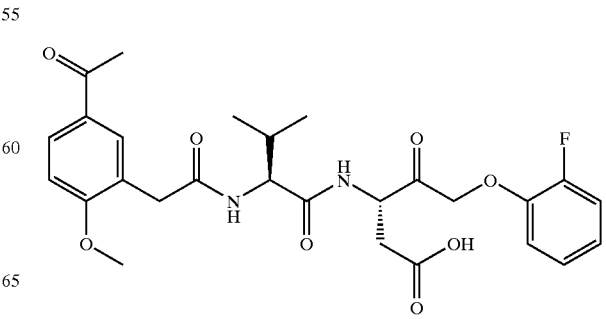

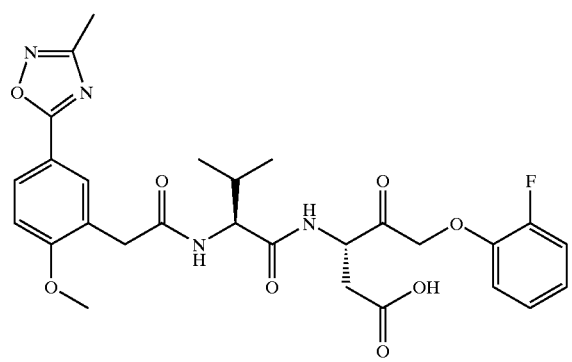
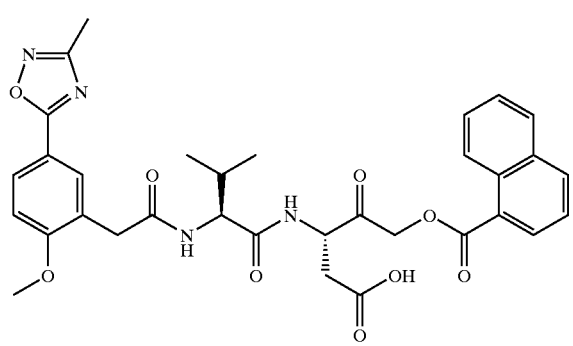
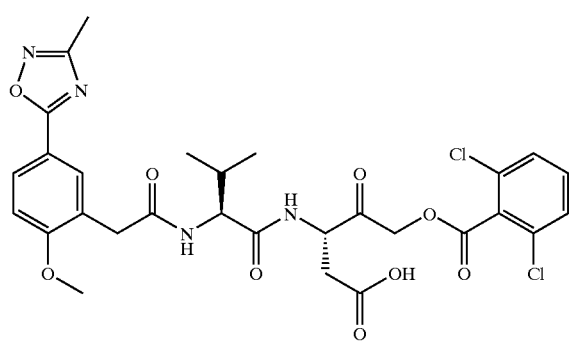
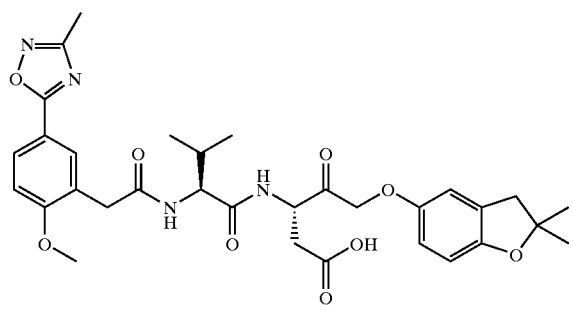
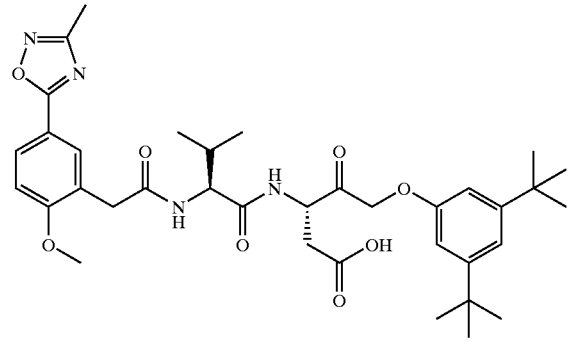
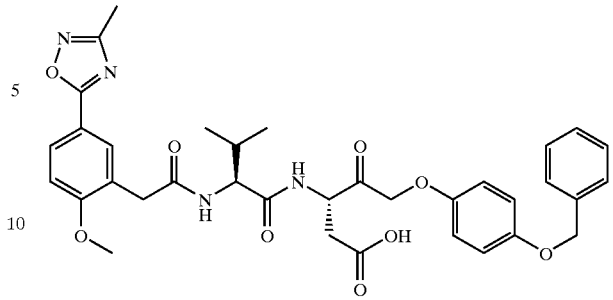
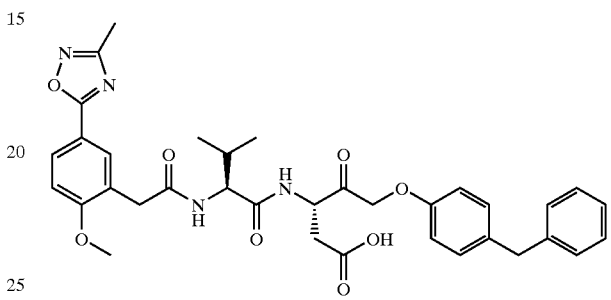
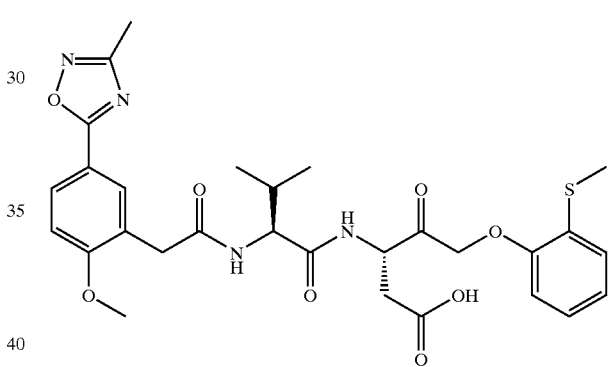
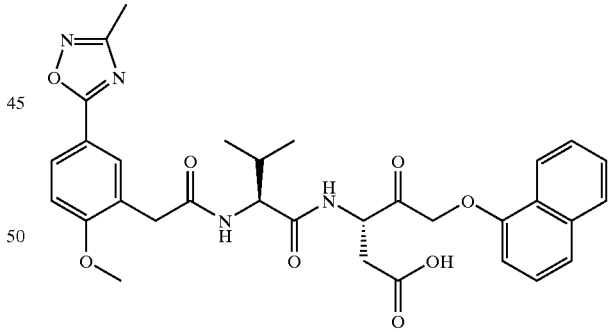
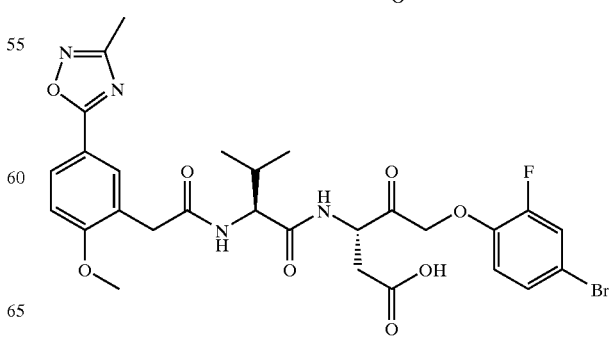

-continued
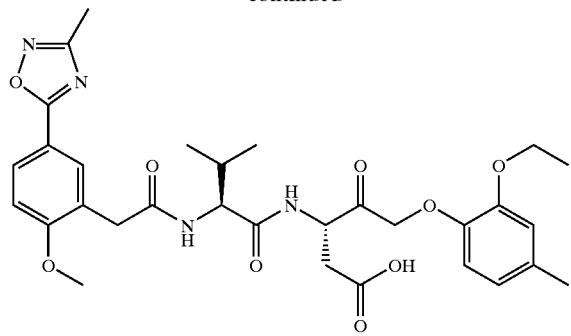
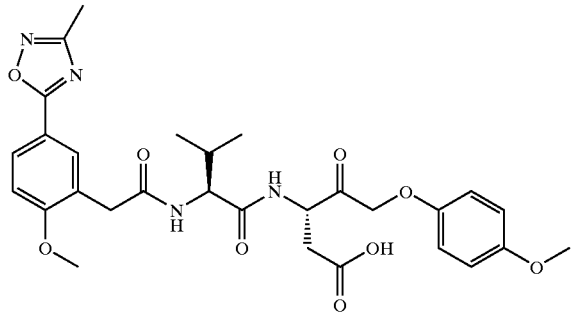
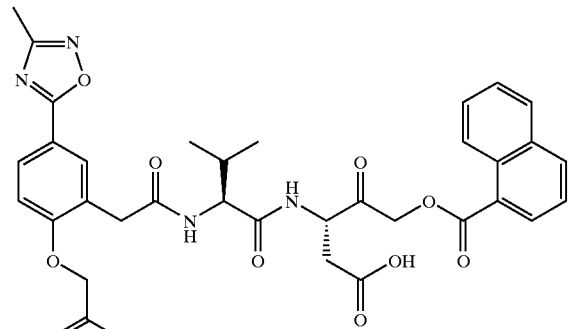
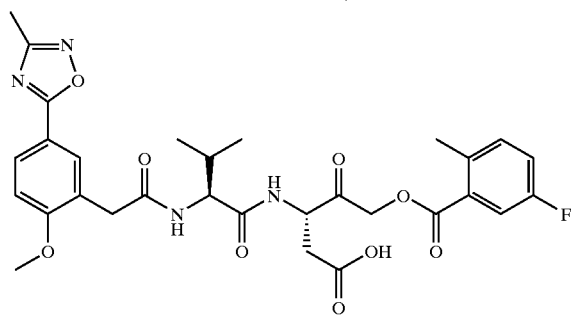
-continued
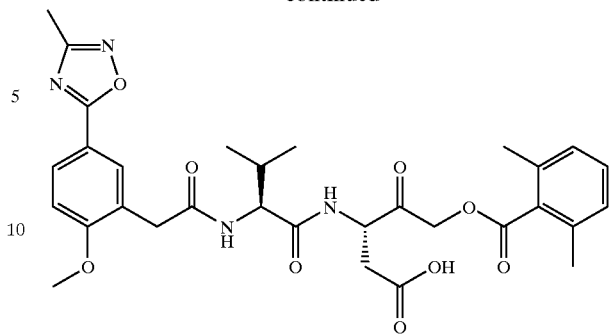
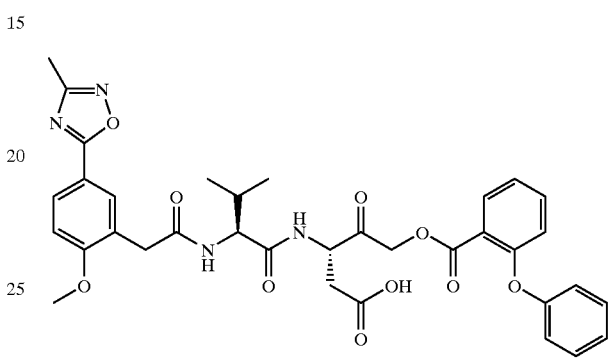
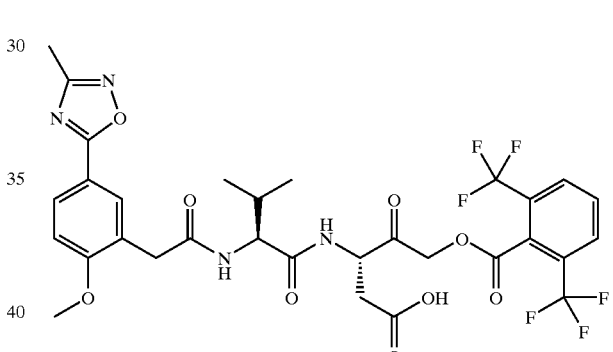
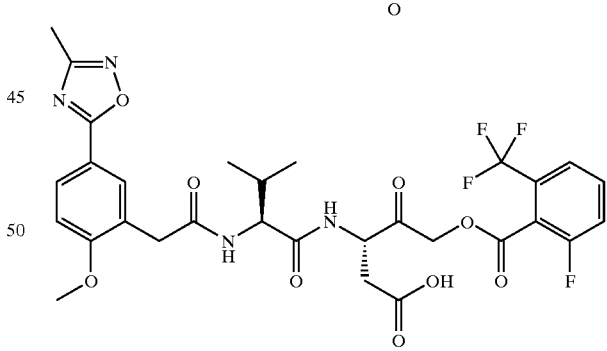
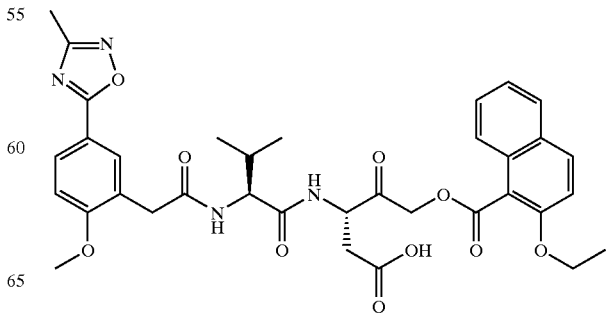
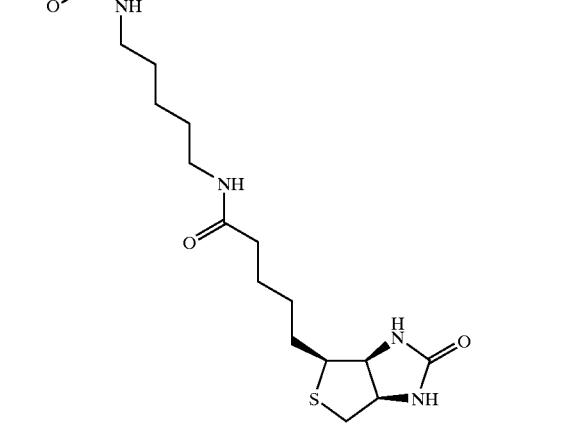

83
-continued
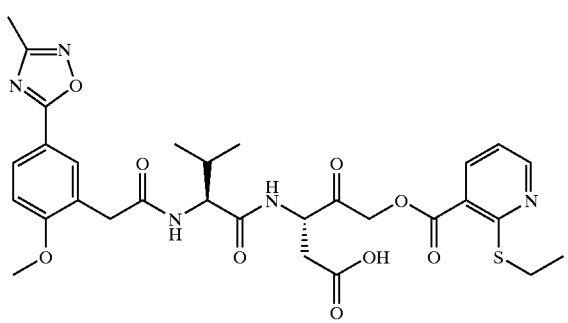
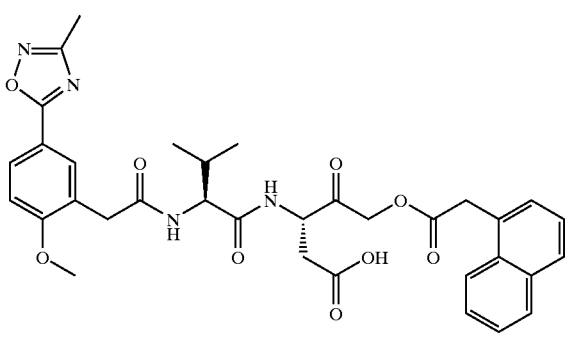
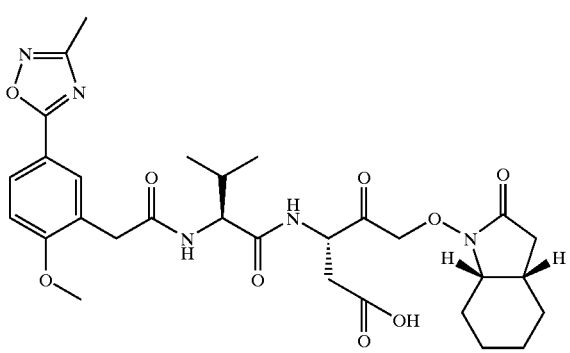
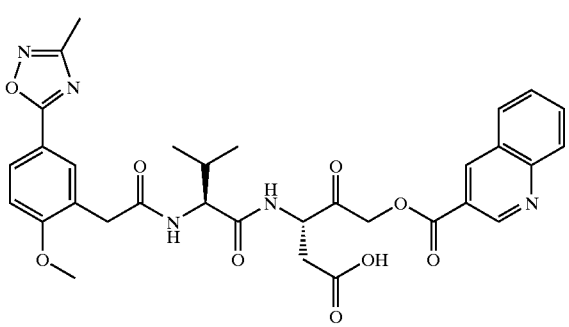
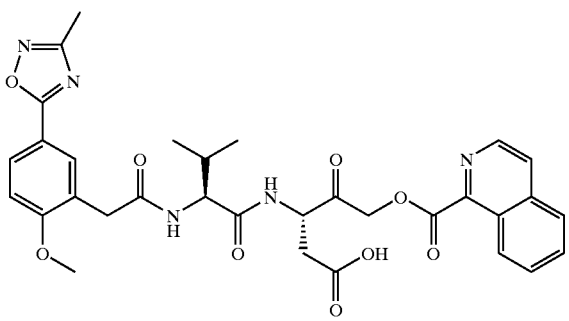
84
-continued
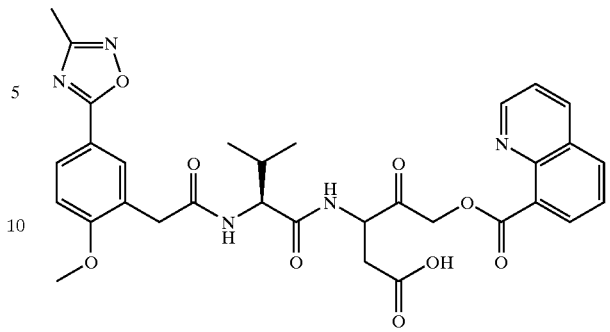
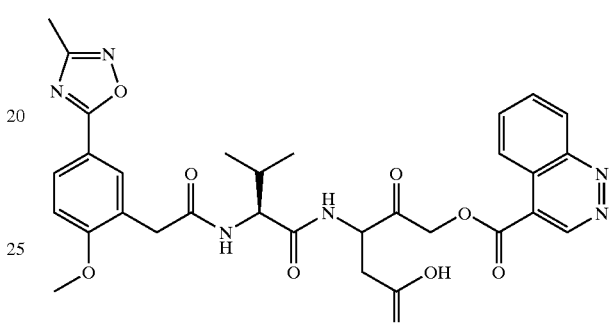
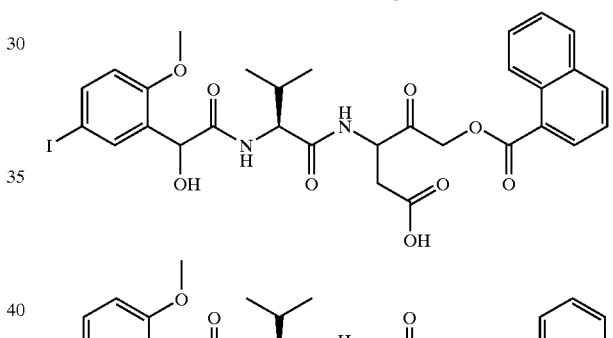
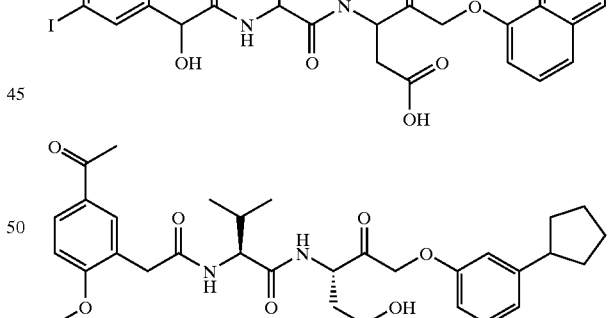
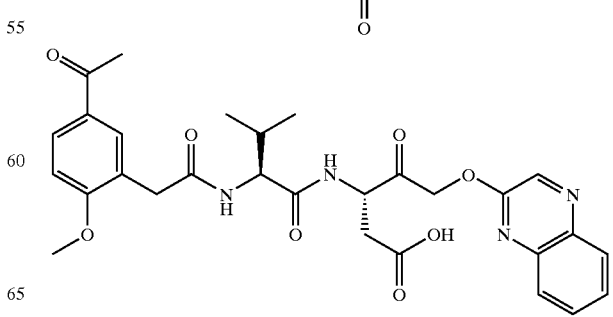

85
-continued
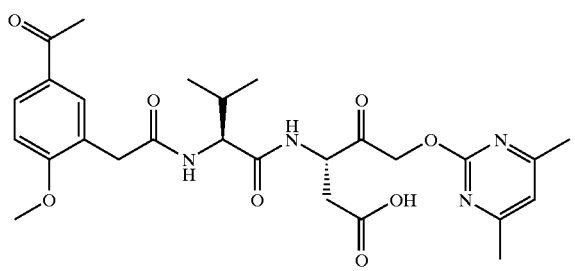
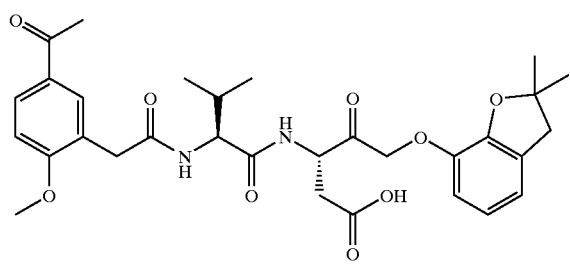
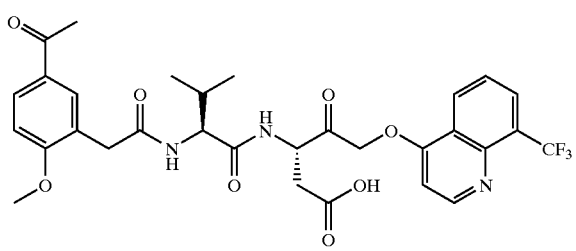
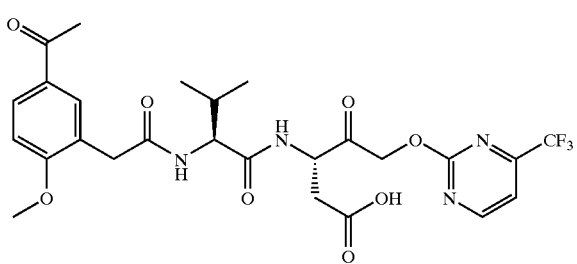
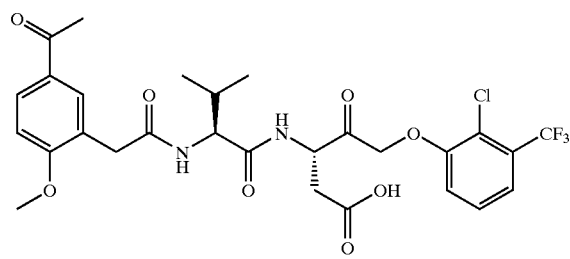
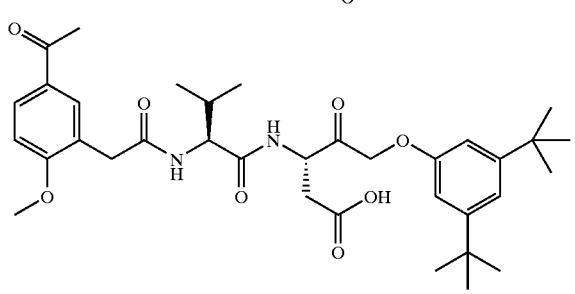
86
-continued
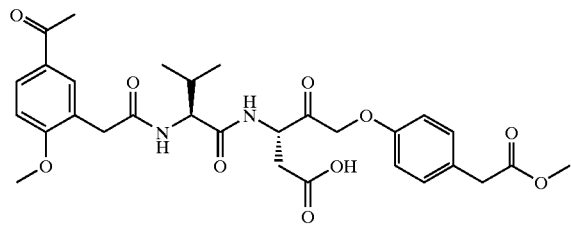
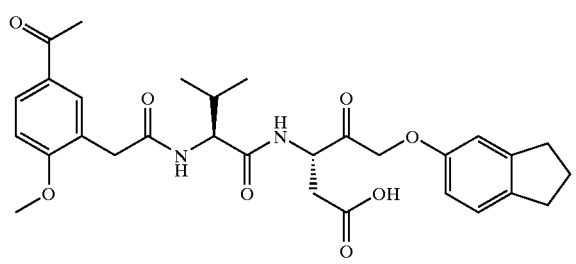
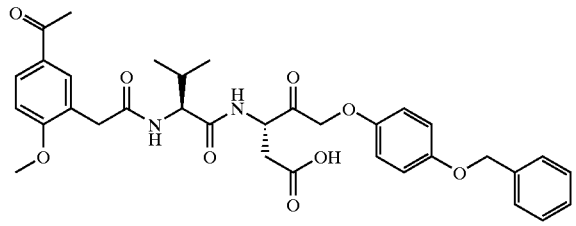
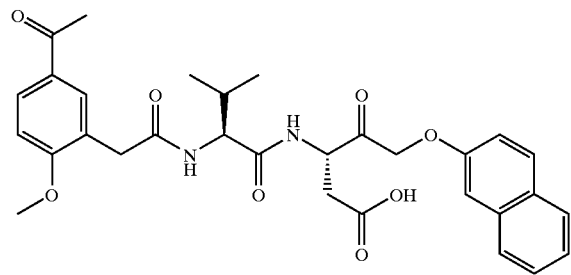
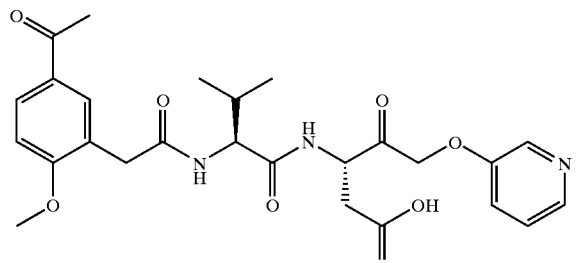
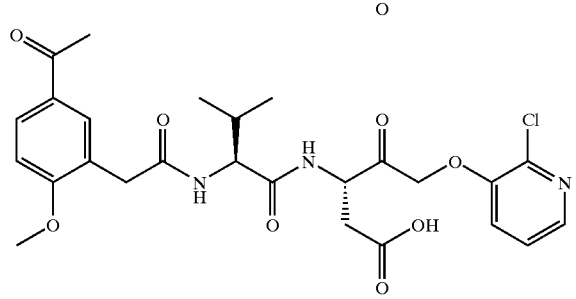

87
-continued
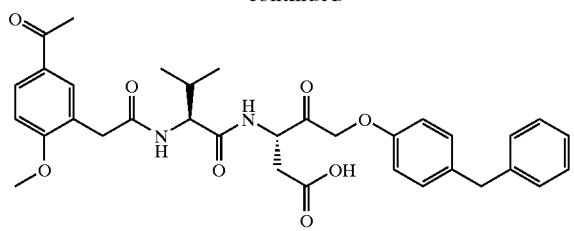
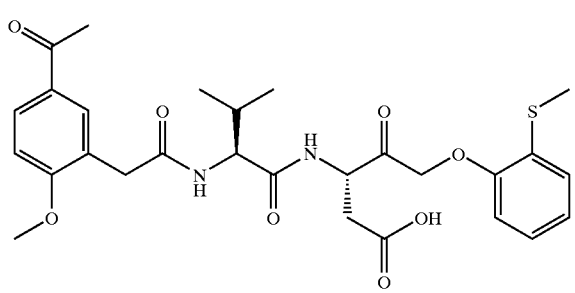
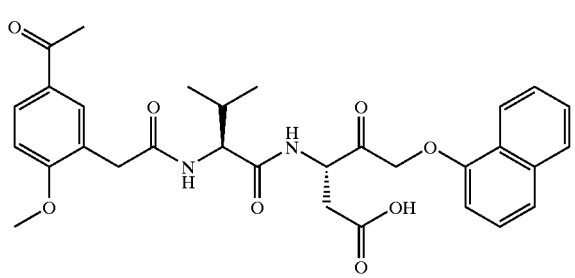
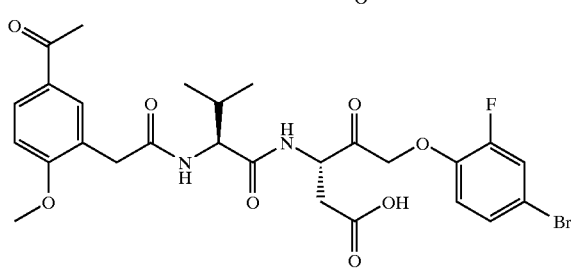
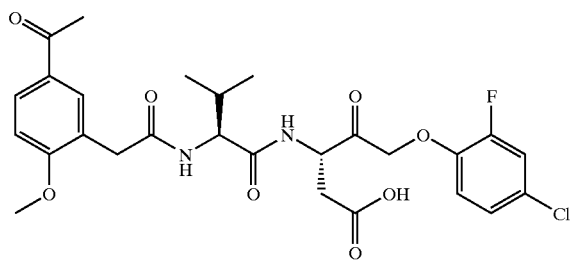
88
-continued
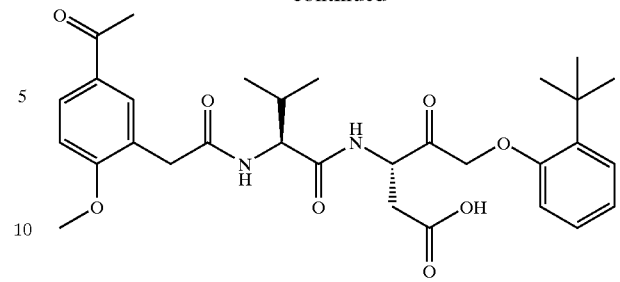
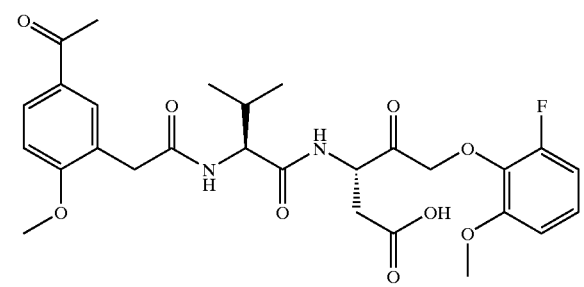
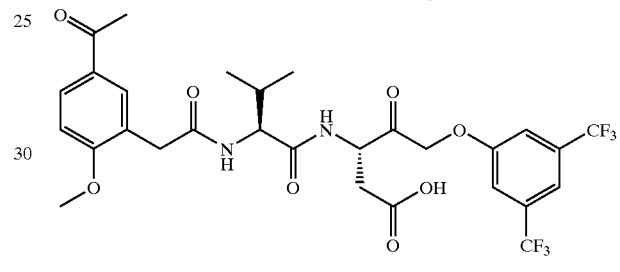
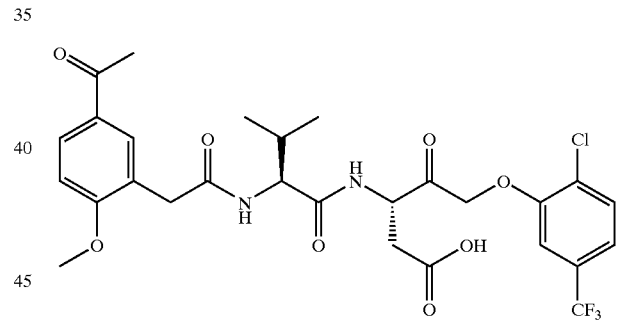
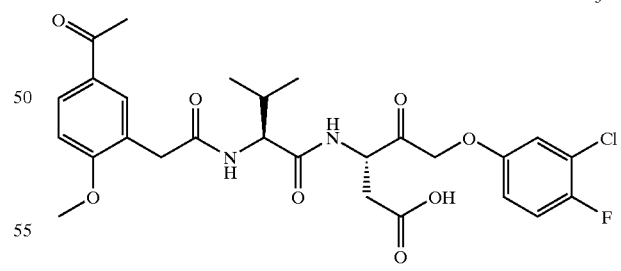
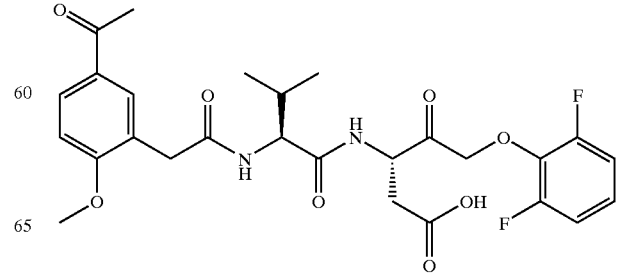

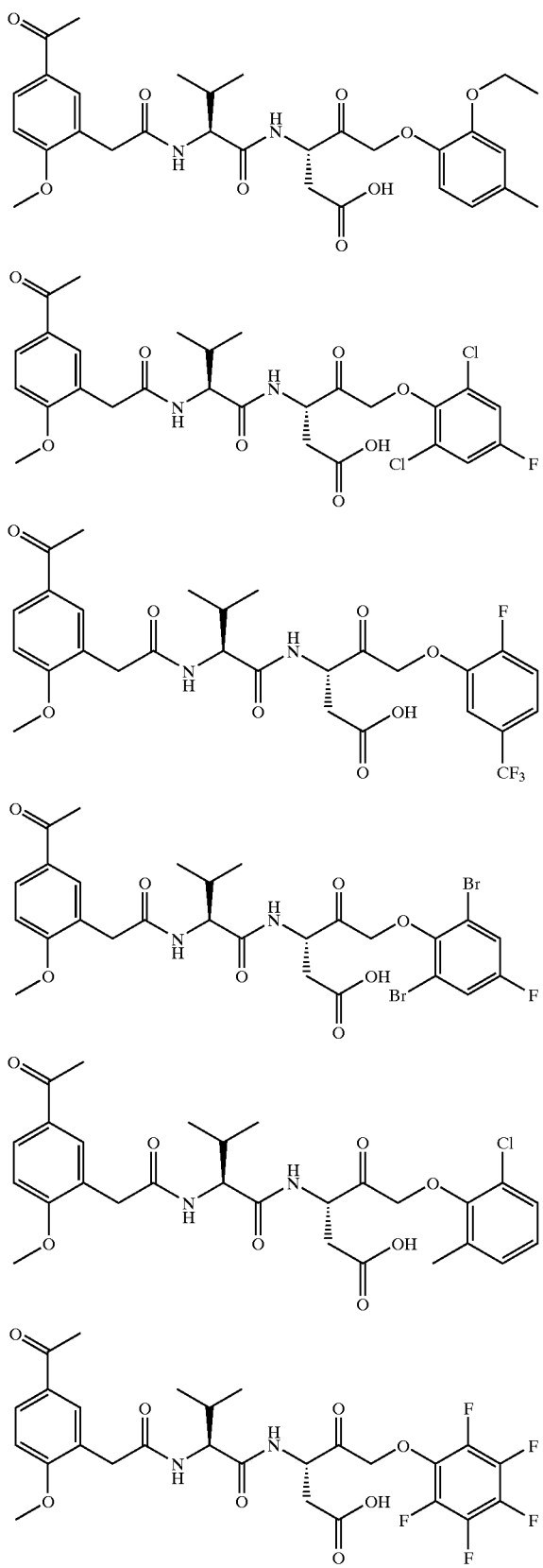

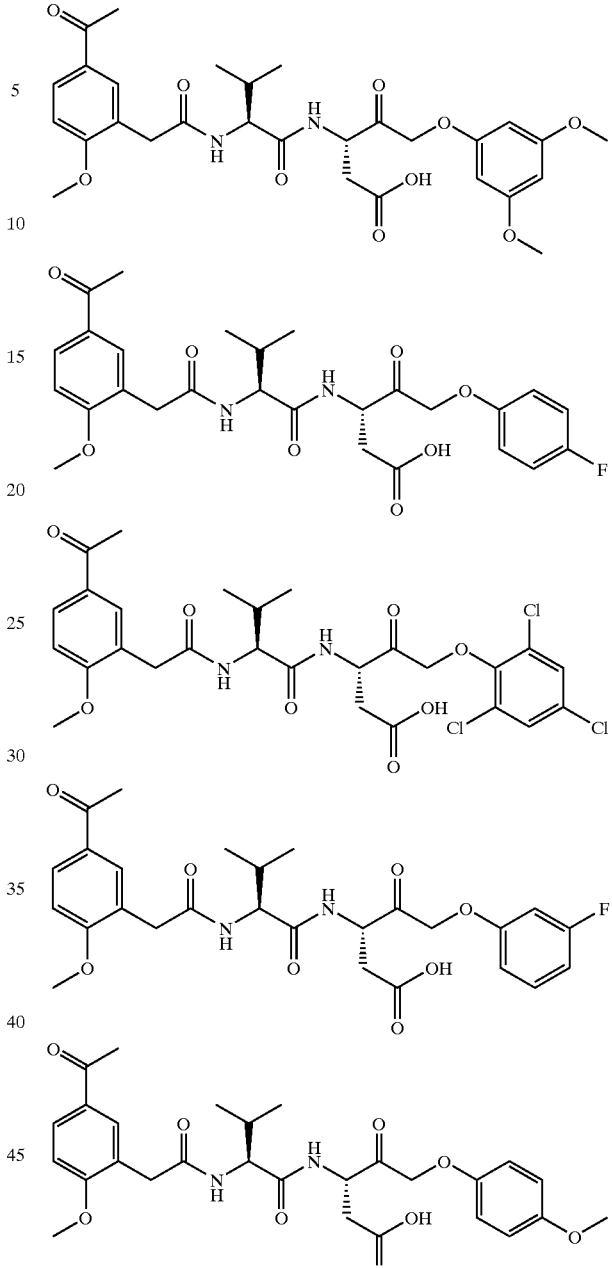

or a salt, hydrate, ester, enantiomer or mixture thereof.

21. A pharmaceutical composition comprising a compound in accordance with claim 1 in combination with a pharmaceutically acceptable carrier.

22. A method of treating or preventing a caspase-3 mediated disease or condition in a mammalian patient in need of such treatment, comprising administering to said patient a compound in accordance with claim 1 in an amount that is effective to treat or prevent said caspase-3 mediated disease.

\* \* \* \* \*